United States Patent
Hansen et al.

(10) Patent No.: US 12,187,699 B2
(45) Date of Patent: Jan. 7, 2025

(54) GSPT1 COMPOUNDS AND METHODS OF USE OF THE NOVEL COMPOUNDS

(71) Applicant: BRISTOL-MYERS SQUIBB COMPANY, Princeton, NJ (US)

(72) Inventors: Joshua Hansen, San Diego, CA (US); Mimi L. Quan, San Diego, CA (US)

(73) Assignee: BRISTOL-MYERS SQUIBB COMPANY, Princeton, NJ (US)

( * ) Notice: Subject to any disclaimer, the term of this patent is extended or adjusted under 35 U.S.C. 154(b) by 0 days.

(21) Appl. No.: 18/300,315

(22) Filed: Apr. 13, 2023

(65) Prior Publication Data

US 2023/0331693 A1    Oct. 19, 2023

Related U.S. Application Data

(60) Provisional application No. 63/331,193, filed on Apr. 14, 2022.

(51) Int. Cl.
| | |
|---|---|
| C07D 401/04 | (2006.01) |
| A61K 45/06 | (2006.01) |
| A61P 35/00 | (2006.01) |
| C07D 401/14 | (2006.01) |
| C07D 405/14 | (2006.01) |

(52) U.S. Cl.
CPC ............ *C07D 401/04* (2013.01); *A61K 45/06* (2013.01); *A61P 35/00* (2018.01); *C07D 401/14* (2013.01); *C07D 405/14* (2013.01)

(58) Field of Classification Search
CPC .. C07D 401/04; C07D 401/14; C07D 405/14; A61P 35/00; A61K 45/06
See application file for complete search history.

(56) References Cited

U.S. PATENT DOCUMENTS 10,648,983 B2 *  5/2020  Filvaroff ................. A61P 35/00

FOREIGN PATENT DOCUMENTS

| WO | 2010053732 A1 | 5/2010 |
|---|---|---|
| WO | 2021069705 A1 | 4/2021 |
| WO | WO-2022220625 A1 * | 10/2022 |

OTHER PUBLICATIONS

International Search Authority, International Search Report and Written Opinion, WIPO, 13 pages, Jun. 30, 2023, US.

* cited by examiner

*Primary Examiner* — Matthew P Coughlin
*Assistant Examiner* — Quincy A McKoy
(74) *Attorney, Agent, or Firm* — Joseph F. Reidy

(57) ABSTRACT

Provided herein are compounds having the formula I

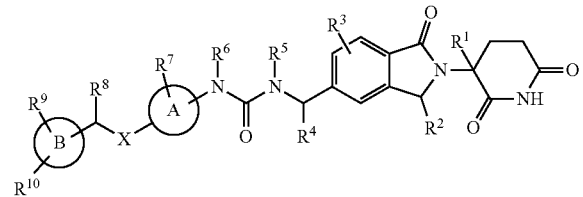

for treating, preventing or managing cancer. Also provided are pharmaceutical compositions comprising the compounds and methods of use of the compounds and compositions. In certain embodiments, the methods encompass treating, preventing or managing cancer, including solid tumors and blood borne tumors using the compounds provided herein.

2 Claims, No Drawings

GSPT1 COMPOUNDS AND METHODS OF USE OF THE NOVEL COMPOUNDS

CROSS-REFERENCE TO RELATED APPLICATIONS

This application claims the benefit under 35 U.S.C. § 119(e) of U.S. Provisional Application Ser. No. 63/331,193, filed Apr. 14, 2022; the disclosure of which is incorporated herein by reference.

FIELD OF THE INVENTION

Provided herein are compounds for treating, preventing or managing cancer. Also provided are pharmaceutical compositions comprising the compounds and methods of use of the compounds and compositions. In certain embodiments, the methods encompass treating, preventing or managing cancer, including solid tumors and blood borne tumors using the compounds provided herein.

BACKGROUND OF THE INVENTION

Pathobiology of Cancer

Cancer is characterized primarily by an increase in the number of abnormal cells derived from a given normal tissue, invasion of adjacent tissues by these abnormal cells, or lymphatic or blood-borne spread of malignant cells to regional lymph nodes and to distant sites (metastasis). Clinical data and molecular biologic studies indicate that cancer is a multistep process that begins with minor pre-neoplastic changes, which may under certain conditions progress to neoplasia. The neoplastic lesion may evolve clonally and develop an increasing capacity for invasion, growth, metastasis, and heterogeneity, especially under conditions in which the neoplastic cells escape the host's immune surveillance. Roitt, I., Brostoff, J and Kale, D., *Immunology*, 17.1-17.12 (3rd ed., Mosby, St. Louis, Mo., 1993).

There is an enormous variety of cancers which are described in detail in the medical literature. Examples include cancer of the lung, colon, rectum, prostate, breast, brain, and intestine. The incidence of cancer continues to climb as the general population ages, as new cancers develop, and as susceptible populations (e.g., people infected with AIDS or excessively exposed to sunlight) grow. A tremendous demand therefore exists for new methods and compositions that can be used to treat patients with cancer.

Many types of cancers are associated with new blood vessel formation, a process known as angiogenesis. Several of the mechanisms involved in tumor-induced angiogenesis have been elucidated. The most direct of these mechanisms is the secretion by the tumor cells of cytokines with angiogenic properties. Examples of these cytokines include acidic and basic fibroblastic growth factor (a,b-FGF), angiogenin, vascular endothelial growth factor (VEGF), and TNF-α. Alternatively, tumor cells can release angiogenic peptides through the production of proteases and the subsequent breakdown of the extracellular matrix where some cytokines are stored (e.g., b-FGF). Angiogenesis can also be induced indirectly through the recruitment of inflammatory cells (particularly macrophages) and their subsequent release of angiogenic cytokines (e.g., TNF-α, b-FGF).

Lymphoma refers to cancers that originate in the lymphatic system. Lymphoma is characterized by malignant neoplasms of lymphocytes-B lymphocytes and T lymphocytes (i.e., B-cells and T-cells). Lymphoma generally starts in lymph nodes or collections of lymphatic tissue in organs including, but not limited to, the stomach or intestines. Lymphoma may involve the marrow and the blood in some cases. Lymphoma may spread from one site to other parts of the body.

The treatment of various forms of lymphomas are described, for example, in U.S. Pat. No. 7,468,363, the entirety of which is incorporated herein by reference. Such lymphomas include, but are not limited to, Hodgkin's lymphoma, non-Hodgkin's lymphoma, cutaneous B-cell lymphoma, activated B-cell lymphoma, diffuse large B-cell lymphoma (DLBCL), mantle cell lymphoma (MCL), follicular center lymphoma, transformed lymphoma, lymphocytic lymphoma of intermediate differentiation, intermediate lymphocytic lymphoma (ILL), diffuse poorly differentiated lymphocytic lymphoma (PDL), centrocytic lymphoma, diffuse small-cleaved cell lymphoma (DSCCL), peripheral T-cell lymphomas (PTCL), cutaneous T-Cell lymphoma and mantle zone lymphoma and low grade follicular lymphoma. Non-Hodgkin's lymphoma (NHL) is the fifth most common cancer for both men and women in the United States, with an estimated 63,190 new cases and 18,660 deaths in 2007. Jemal A, et al., *CA Cancer J Clin* 2007; 57(1):43-66. The probability of developing NHL increases with age and the incidence of NHL in the elderly has been steadily increasing in the past decade, causing concern with the aging trend of the US population. Id. Clarke C A, et al., *Cancer* 2002; 94(7):2015-2023.

Diffuse large B-cell lymphoma (DLBCL) accounts for approximately one-third of non-Hodgkin's lymphomas. While some DLBCL patients are cured with traditional chemotherapy, the remainder die from the disease. Anticancer drugs cause rapid and persistent depletion of lymphocytes, possibly by direct apoptosis induction in mature T and B cells. See K. Stahnke. et al., *Blood* 2001, 98:3066-3073. Absolute lymphocyte count (ALC) has been shown to be a prognostic factor in follicular non-Hodgkin's lymphoma and recent results have suggested that ALC at diagnosis is an important prognostic factor in diffuse large B-cell lymphoma. See D. Kim et al., *Journal of Clinical Oncology*, 2007 ASCO Annual Meeting Proceedings Part I. Vol 25, No. 18S (June 20 Supplement), 2007: 8082.

Leukemia refers to malignant neoplasms of the blood-forming tissues. Various forms of leukemias are described, for example, in U.S. Pat. No. 7,393,862 and U.S. provisional patent application No. 60/380,842, filed May 17, 2002, the entireties of which are incorporated herein by reference. Although viruses reportedly cause several forms of leukemia in animals, causes of leukemia in humans are to a large extent unknown. *The Merck Manual*, 944-952 (17th ed. 1999). Transformation to malignancy typically occurs in a single cell through two or more steps with subsequent proliferation and clonal expansion. In some leukemias, specific chromosomal translocations have been identified with consistent leukemic cell morphology and special clinical features (e.g., translocations of 9 and 22 in chronic myelocytic leukemia, and of 15 and 17 in acute promyelocytic leukemia). Acute leukemias are predominantly undifferentiated cell populations and chronic leukemias more mature cell forms.

Acute leukemias are divided into lymphoblastic (ALL) and non-lymphoblastic (ANLL) types. *The Merck Manual*, 946-949 (17th ed. 1999). They may be further subdivided by their morphologic and cytochemical appearance according to the French-American-British (FAB) classification or according to their type and degree of differentiation. The use of specific B- and T-cell and myeloid-antigen monoclonal antibodies are most helpful for classification. ALL is predominantly a childhood disease which is established by laboratory findings and bone marrow examination. ANLL, also known as acute myelogenous leukemia or acute myeloblastic leukemia (AML), occurs at all ages and is the more common acute leukemia among adults; it is the form usually associated with irradiation as a causative agent.

Chronic leukemias are described as being lymphocytic (CLL) or myelocytic (CML). *The Merck Manual*, 949-952 ($17^{th}$ ed. 1999). CLL is characterized by the appearance of mature lymphocytes in blood, bone marrow, and lymphoid organs. The hallmark of CLL is sustained, absolute lymphocytosis (>5,000/L) and an increase of lymphocytes in the bone marrow. Most CLL patients also have clonal expansion of lymphocytes with B-cell characteristics. CLL is a disease of middle or old age. In CML, the characteristic feature is the predominance of granulocytic cells of all stages of differentiation in blood, bone marrow, liver, spleen, and other organs. In the symptomatic patient at diagnosis, the total white blood cell (WBC) count is usually about 200,000/μL, but may reach 1,000,000/μL. CML is relatively easy to diagnose because of the presence of the Philadelphia chromosome.

In addition to the acute and chronic categorization, neoplasms are also categorized based upon the cells giving rise to such disorder into precursor or peripheral. See e.g., U.S. patent publication no. 2008/0051379, the disclosure of which is incorporated herein by reference in its entirety. Precursor neoplasms include ALLs and lymphoblastic lymphomas and occur in lymphocytes before they have differentiated into either a T- or B-cell. Peripheral neoplasms are those that occur in lymphocytes that have differentiated into either T- or B-cells. Such peripheral neoplasms include, but are not limited to, B-cell CLL, B-cell prolymphocytic leukemia, lymphoplasmacytic lymphoma, mantle cell lymphoma, follicular lymphoma, extranodal marginal zone B-cell lymphoma of mucosa-associated lymphoid tissue, nodal marginal zone lymphoma, splenic marginal zone lymphoma, hairy cell leukemia, plasmacytoma, diffuse large B-cell lymphoma and Burkitt lymphoma. In over 95 percent of CLL cases, the clonal expansion is of a B cell lineage. See Cancer: Principles & Practice of Oncology (3rd Edition) (1989) (pp. 1843-1847). In less than 5 percent of CLL cases, the tumor cells have a T-cell phenotype. Notwithstanding these classifications, however, the pathological impairment of normal hematopoiesis is the hallmark of all leukemias.

Multiple myeloma (MM) is a cancer of plasma cells in the bone marrow. Normally, plasma cells produce antibodies and play a key role in immune function. However, uncontrolled growth of these cells leads to bone pain and fractures, anemia, infections, and other complications. Multiple myeloma is the second most common hematological malignancy, although the exact causes of multiple myeloma remain unknown. Multiple myeloma causes high levels of proteins in the blood, urine, and organs, including but not limited to M-protein and other immunoglobulins (antibodies), albumin, and beta-2-microglobulin. M-protein, short for monoclonal protein, also known as paraprotein, is a particularly abnormal protein produced by the myeloma plasma cells and can be found in the blood or urine of almost all patients with multiple myeloma.

Skeletal symptoms, including bone pain, are among the most clinically significant symptoms of multiple myeloma. Malignant plasma cells release osteoclast stimulating factors (including IL-1, IL-6 and TNF) which cause calcium to be leached from bones causing lytic lesions; hypercalcemia is another symptom. The osteoclast stimulating factors, also referred to as cytokines, may prevent apoptosis, or death of myeloma cells. Fifty percent of patients have radiologically detectable myeloma-related skeletal lesions at diagnosis. Other common clinical symptoms for multiple myeloma include polyneuropathy, anemia, hyperviscosity, infections, and renal insufficiency.

Solid tumors are abnormal masses of tissue that may, but usually do not contain cysts or liquid areas. Solid tumors may be benign (not cancer), or malignant (cancer). Different types of solid tumors are named for the type of cells that form them. Examples of types solid tumors include, but are not limited to malignant melanoma, adrenal carcinoma, breast carcinoma, renal cell cancer, carcinoma of the pancreas, non-small-cell lung carcinoma (NSCLC) and carcinoma of unknown primary. Drugs commonly administered to patients with various types or stages of solid tumors include, but are not limited to, celebrex, etoposide, cyclophosphamide, docetaxel, apecitabine, IFN, tamoxifen, IL-2, GM-CSF, or a combination thereof.

While patients who achieve a complete remission after initial therapy have a good chance for cure, less than 10% of those who do not respond or relapse achieve a cure or a response lasting longer than 3 years. See Cerny T, et al., *Ann Oncol* 2002; 13 Suppl 4:211-216.

Rituximab is known to deplete normal host B cells. See M. Aklilu et al., Annals of Oncology 15:1109-1114, 2004. The long-term immunologic effects of B cell depletion with rituximab and the characteristics of the reconstituting B cell pool in lymphoma patients are not well defined, despite the widespread usage of this therapy. See Jennifer H. Anolik et al., *Clinical Immunology*, vol. 122, issue 2, February 2007, pages 139-145.

The approach for patients with relapsed or refractory disease relies heavily on experimental treatments followed by stem cell transplantation, which may not be appropriate for patients with a poor performance status or advanced age. Therefore, a tremendous demand exists for new methods that can be used to treat patients with NHL.

The link between cancer an altered cellular metabolism has been well established. See Cairns, R. A., et al. *Nature Rev.*, 2011, 11:85-95. Understanding tumor cell metabolism and the associated genetic changes thereof may lead to the identification of improved methods of cancer treatment. Ibid. For example, tumor cell survival and proliferation via increased glucose metabolism has been linked to the PIK3 pathway, whereby mutations in tumor suppressor genes such as PTEN activate tumor cell metabolism. Id. AKT1 (a.k.a., PKB) stimulates glucose metabolism associated with tumor cell growth by various interactions with PFKFB3, ENTPD5, mTOR and TSC2 (a.k.a., tuberin). Ibid.

Transcription factors HIF1 and HIF2 are largely responsible for cellular response to low oxygen conditions often associated with tumors. Id. Once activated, HIF1 promotes tumor cell capacity to carry out glycolysis. Ibid. Thus, inhibition of HIF1 may slow or reverse tumor cell metabolism. Activation of HIF1 has been linked to PI3K, tumor suppressor proteins such as VHL, succinate dehydrogenase (SDH) and fumarate hydratase. Ibid. The oncogenic transcription factor MYC has also been linked to tumor cell metabolism, specifically glycolysis. Ibid. MYC also promotes cell proliferation by glutamine metabolic pathways. Ibid.

AMP-activated protein kinase (AMPK) functions as a metabolic check point which tumor cells must overcome in order to proliferate. Ibid. Several mutations have been identified which suppress AMPK signaling in tumor cells.

See Shackelford, D. B. & Shaw, R. J., *Nature Rev. Cancer*, 2009, 9: 563-575. STK11 has been identified as a tumor suppressor gene related to the role of AMPK. See Cairns, R. A., et al. *Nature Rev.*, 2011, 11:85-95.

The transcription factor p53, a tumor suppressor, also has an important role in the regulation of cellular metabolism. Ibid. The loss of p53 in tumor cells may be a significant contributor to changes in tumor cell metabolism to the glycolytic pathway. Ibid. The OCT1 transcription factor, another potential target for chemotherapeutics, may cooperate with p53 in regulating tumor cell metabolism. Ibid.

Pyruvate kinate M2 (PKM2) promotes changes in cellular metabolism which confer metabolic advantages to cancer cells by supporting cell proliferation. Ibid. For example, lung cancer cells which express PKM2 over PKM1 have been found to have such an advantage. Ibid. In the clinic, PKM2 has been identified as being overexpressed in a number of cancer types. Ibid. Thus PKM2 may be a useful biomarker for the early detection of tumors.

Mutations in isocitrate dehydrogenases IDH1 and IDH2 have been linked to tumorigenesis, specifically, in glioblastoma and acute myeloid leukemia. See Mardis, E. R. et al., *N. Engl. J. Med.*, 2009, 361: 1058-1066; Parsons, D. W. et al., *Science*, 2008, 321: 1807-1812.

The incidence of cancer continues to climb as the general population ages, as new cancers develop, and as susceptible populations (e.g., people infected with AIDS, the elderly or excessively exposed to sunlight) grow. A tremendous demand therefore exists for new methods, treatments and compositions that can be used to treat patients with cancer including but not limited to those with lymphoma, NHL, multiple myeloma, AML, leukemias, and solid tumors.

Accordingly, compounds that can control and/or inhibit unwanted angiogenesis or inhibit the production of certain cytokines, including TNF-α, may be useful in the treatment and prevention of various forms of cancer.

Methods of Treating Cancer

Current cancer therapy may involve surgery, chemotherapy, hormonal therapy and/or radiation treatment to eradicate neoplastic cells in a patient (see, for example, Stockdale, 1998, *Medicine*, vol. 3, Rubenstein and Federman, eds., Chapter 12, Section IV). Recently, cancer therapy could also involve biological therapy or immunotherapy. All of these approaches may pose significant drawbacks for the patient. Surgery, for example, may be contraindicated due to the health of a patient or may be unacceptable to the patient. Additionally, surgery may not completely remove neoplastic tissue. Radiation therapy is only effective when the neoplastic tissue exhibits a higher sensitivity to radiation than normal tissue. Radiation therapy can also often elicit serious side effects. Hormonal therapy is rarely given as a single agent. Although hormonal therapy can be effective, it is often used to prevent or delay recurrence of cancer after other treatments have removed the majority of cancer cells. Certain biological and other therapies are limited in number and may produce side effects such as rashes or swellings, flu-like symptoms, including fever, chills and fatigue, digestive tract problems or allergic reactions.

With respect to chemotherapy, there are a variety of chemotherapeutic agents available for treatment of cancer. A number of cancer chemotherapeutics act by inhibiting DNA synthesis, either directly or indirectly by inhibiting the biosynthesis of deoxyribonucleotide triphosphate precursors, to prevent DNA replication and concomitant cell division. Gilman et al., *Goodman and Gilman's: The Pharmacological Basis of Therapeutics*, Tenth Ed. (McGraw Hill, New York).

Despite availability of a variety of chemotherapeutic agents, chemotherapy has many drawbacks. Stockdale, *Medicine*, vol. 3, Rubenstein and Federman, eds., ch. 12, sect. 10, 1998. Almost all chemotherapeutic agents are toxic, and chemotherapy causes significant and often dangerous side effects including severe nausea, bone marrow depression, and immunosuppression. Additionally, even with administration of combinations of chemotherapeutic agents, many tumor cells are resistant or develop resistance to the chemotherapeutic agents. In fact, those cells resistant to the particular chemotherapeutic agents used in the treatment protocol often prove to be resistant to other drugs, even if those agents act by different mechanism from those of the drugs used in the specific treatment. This phenomenon is referred to as multidrug resistance. Because of the drug resistance, many cancers prove refractory to standard chemotherapeutic treatment protocols.

There exists a significant need for safe and effective compounds and methods for treating, preventing and managing cancer, including for cancers that are refractory to standard treatments, such as surgery, radiation therapy, chemotherapy and hormonal therapy, while reducing or avoiding the toxicities and/or side effects associated with the conventional therapies.

SUMMARY OF THE INVENTION

Provided herein are compounds, pharmaceutical compositions containing the compounds and methods of use thereof in treating cancer, including solid tumors and blood borne tumors.

1. In a first embodiment, the present invention comprises a compound having a Formula (I),

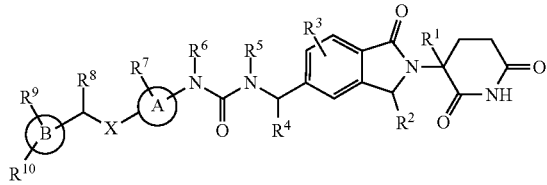

or a pharmaceutically acceptable salt, solvate, hydrate, co-crystal, clathrate, polymorph or tautomer thereof, a pharmaceutically acceptable salt of the polymorph or tautomer, a stereoisomer of any of the foregoing, or a mixture thereof, wherein:

A is independently selected from an unsubstituted or substituted 3 to 12 membered cycloalkyl, 4 to 12 membered heterocyclic, 5 to 12 membered aryl, or a 5 to 12 membered heteroaryl ring;

B is independently selected from an unsubstituted or substituted 3 to 12 membered cycloalkyl, 4 to 12 membered heterocyclic, 5 to 12 membered aryl or a 5 to 12 membered heteroaryl ring;

X is independently selected from O or —$NR^{11}$;

$R^1$ is independently selected from hydrogen, halogen, —$C_1$-$C_6$ alkyl or a 3 to 6 membered cycloalkyl;

$R^2$ is independently selected from hydrogen, halogen, —C(O), —$C_1$-$C_6$ alkyl, a 3 to 6 membered cycloalkyl, wherein the alkyl or cycloalkyl may be optionally substituted with —$R^{11}$, —N($R^{11}R^{11}$), —$NHR^{11}$ or —$OR^{11}$;

$R^3$ is independently selected from hydrogen, halogen, —$OR^{11}$, —N($R^{11}R^{11}$), —$NHR^{11}$, —$C_1$-$C_6$ alkyl, a 3 to 6 membered cycloalkyl, 4 to 12 membered heterocyclic, 5 to 12 membered aryl or a 5 to 12 membered heteroaryl ring, wherein the alkyl, cycloalkyl, heterocyclic and heteroaryl may be optionally substituted with —$R^{11}$, —$N(R^{11}R^{11})$, —$NHR^{11}$ or —$OR^{11}$;

$R^4$ is independently selected from hydrogen, halogen, —$C_1$-$C_6$ alkyl, a 3 to 6 membered cycloalkyl, 4 to 12 membered heterocyclic, 5 to 12 membered aryl or a 5 to 12 membered heteroaryl ring, wherein the alkyl, cycloalkyl, heterocyclic and heteroaryl may be optionally substituted with —$R^{11}$, —$NHR^{11}$ or —$OR^{11}$;

$R^5$ is independently selected from hydrogen, —$C_1$-$C_6$ alkyl, a 3 to 6 membered cycloalkyl, 4 to 12 membered heterocyclic, 5 to 12 membered aryl or a 5 to 12 membered heteroaryl ring, wherein the alkyl, cycloalkyl, heterocyclic and heteroaryl may be optionally substituted with —$R^{11}$, —$N(R^{11}R^{11})$, —$NHR^{11}$ or —$OR^{11}$;

$R^6$ is independently selected from hydrogen, —$C_1$-$C_6$ alkyl, a 3 to 6 membered cycloalkyl, 4 to 12 membered heterocyclic, 5 to 12 membered aryl or a 5 to 12 membered heteroaryl ring, wherein the alkyl, cycloalkyl, heterocyclic and heteroaryl may be optionally substituted with —$R^{11}$, —$N(R^{11}R^{11})$, —$NHR^{11}$ or —$OR^{11}$;

wherein two $R^5$ and $R^6$ substituents together with the carbon atoms they are attached to, may join to form a 5 or 6 membered ring that may be saturated, partially saturated, and may further optionally be substituted with 1 or 2 $R^{11}$ substituents;

$R^7$ is independently selected from hydrogen, halogen, —$OR^{11}$, —$C_1$-$C_6$ alkyl, —($C_1$-$C_6$ haloalkyl), —($C_1$-$C_6$ alkyl)-O—($C_1$-$C_6$ alkyl), —$NHR^{11}$, —$N(R^{11}R^{11})$, —CN, 3 to 12 membered cycloalkyl, 4 to 12 membered heterocyclic, 5 to 12 membered aryl or a 5 to 12 membered heteroaryl ring, —$C_2$-$C_6$ alkenyl, —O—($C_1$-$C_6$ haloalkyl)-O—($C_1$-$C_6$ alkyl), —C(=O)—($C_1$-$C_6$ alkyl), —C(=O)OH, —C(=O)—O—($C_1$-$C_6$ alkyl), —C(=O)$NH_2$, —C(=O)NH($R^{11}$), —C(=O)N($R^{11}R^{11}$), —S(O)$_2R^{11}$, —S(=O)$R^{11}$, —$SR^{11}$, —S(=O)$_2NH_2$, —S(=O)$_2$NH($C_1$-$C_6$ alkyl), or —S(=O)$_2$N($C_1$-$C_6$ alkyl)$_2$, wherein the alkyl, haloalkyl, cycloalkyl, heterocyclic, aryl, or heteroaryl may be optionally substituted with —$R^{11}$, —$N(R^{11}R^{11})$, —$NHR^{11}$ or —$OR^{11}$;

$R^8$ is independently selected from hydrogen, halogen or a —$C_1$-$C_6$ alkyl, optionally substituted with —$R^{11}$, —$N(R^{11}R^{11})$, —$NHR^{11}$ or —$OR^{11}$;

$R^9$ is independently selected from hydrogen, halogen, —$OR^{11}$, —$C_1$-$C_6$ alkyl, —($C_1$-$C_6$ haloalkyl), —($C_1$-$C_6$ alkyl)-O—($C_1$-$C_6$ alkyl), —$NHR^{11}$, —$N(R^{11}R^{11})$, —CN, 3 to 12 membered cycloalkyl, 4 to 12 membered heterocyclic, 5 to 12 membered aryl or a 5 to 12 membered heteroaryl ring, —$C_2$-$C_6$ alkenyl, —O—($C_1$-$C_6$ haloalkyl)-O—($C_1$-$C_6$ alkyl), —C(=O)—($C_1$-$C_6$ alkyl), —C(=O)OH, —C(=O)—O—($C_1$-$C_6$ alkyl), —C(=O)$NH_2$, —C(=O)NH($R^{11}$), —C(=O)N($R^{11}R^{11}$), —S(O)$_2R^{11}$, —S(=O)$R^{11}$, —$SR^{11}$, —S(=O)$_2NH_2$, —S(=O)$_2$NH($C_1$-$C_6$ alkyl), or —S(=O)$_2$N($C_1$-$C_6$ alkyl)$_2$, wherein the alkyl, haloalkyl, cycloalkyl, heterocyclic, aryl, or heteroaryl may be optionally substituted with —$R^{11}$, —$N(R^{11}R^{11})$, —$NHR^{11}$ or —$OR^{11}$;

$R^{10}$ is independently selected from hydrogen, halogen, —$OR^{11}$, —$C_1$-$C_6$ alkyl, —($C_1$-$C_6$ haloalkyl), —($C_1$-$C_6$ alkyl)-O—($C_1$-$C_6$ alkyl), —$NHR^{11}$, —$N(R^{11}R^{11})$, —CN, 3 to 12 membered cycloalkyl, 4 to 12 membered heterocyclic, 5 to 12 membered aryl or a 5 to 12 membered heteroaryl ring, —$C_2$-$C_6$ alkenyl, —O—($C_1$-$C_6$ haloalkyl)-O—($C_1$-$C_6$ alkyl), —C(=O)—($C_1$-$C_6$ alkyl), —C(=O)OH, —C(=O)—O—($C_1$-$C_6$ alkyl), —C(=O)$NH_2$, —C(=O)NH($R^{11}$), —C(=O)N($R^{11}R^{11}$), —S(O)$_2R^{11}$, —S(=O)$R^{11}$, —$SR^{11}$, —S(=O)$_2NH_2$, —S(=O)$_2$NH($C_1$-$C_6$ alkyl), or —S(=O)$_2$N($C_1$-$C_6$ alkyl)$_2$, wherein the alkyl, haloalkyl, cycloalkyl, heterocyclic, aryl, or heteroaryl may be optionally substituted with —$R^{11}$, —$N(R^{11}R^{11})$, —$NHR^{11}$ or —$OR^{11}$;

$R^{11}$ is independently selected from hydrogen, halogen, —$C_1$-$C_6$ alkyl, —$C_2$-$C_6$alkenyl, —$C_1$-$C_6$ haloalkyl, a 3 to 12 membered cycloalkyl, 4 to 12 membered heterocyclic, 5 to 12 membered aryl or a 5 to 12 membered heteroaryl ring; wherein the alkyl, alkenyl, haloalkyl, cycloalkyl, heterocyclic, aryl or heteroaryl ring in $R^{11}$ are each independently unsubstituted or substituted with 1, 2, or 3 $R^{12}$ substituents;

$R^{12}$ in each instance is independently selected from hydrogen, —$C_1$-$C_6$ alkyl, halogen, —OH, —O—($C_1$-$C_6$ alkyl)-, —$NH_2$, a 3 to 12 membered alkyl, 5 to 12 membered heterocyclic, 5 to 12 membered aryl or 5 to 12 membered heteroaryl ring; wherein the alkyl, alkenyl, haloalkyl, cycloalkyl, heterocyclic, aryl or heteroaryl ring in $R^{12}$ are each independently unsubstituted or substituted with $R^{13}$;

$R^{13}$ is independently hydrogen, halo, —$C_1$-$C_6$ alkyl, —$C_1$-$C_6$ haloalkyl, —$C_1$-$C_6$ alkoxyalkyl, oxo, hydroxyl or —$C_1$-$C_6$ alkoxy; and further wherein two $R^9$ and $R^{10}$ substituents on adjacent carbon atoms of the A or B group may join to form a 5 or 6 membered ring that may be saturated, partially saturated, or aromatic;

and may further optionally be substituted with 1 or 2 $R^{13}$ substituents and may include an oxo substituent if the ring is not an aromatic ring;

wherein the heterocyclic and heteroaryl cyclic ring in each A, B, $R^3$, $R^4$, $R^5$, $R^6$, $R^7$, $R^9$, $R^{10}$, $R^{11}$, $R^{12}$ and $R^{13}$ may include 1, 2 or 3 heteroatoms independently selected from O, N or S.

In one embodiment, the compound provided herein is a compound of Formula I.

In one embodiment, the compound provided herein is a pharmaceutically acceptable salt of the compound of Formula I.

In one embodiment, the compound provided herein is a solvate of the compound of Formula I.

In one embodiment, the compound provided herein is a hydrate of compound of Formula I.

In one embodiment, the compound provided herein is a clathrate of the compound of Formula I.

Also provided are pharmaceutical compositions formulated for administration by an appropriate route and means containing effective concentrations of one or more of the compounds provided herein, or an enantiomer or a mixture of enantiomers thereof, or a pharmaceutically acceptable salt, solvate, hydrate, co-crystal, clathrate, or polymorph thereof, and optionally comprising at least one pharmaceutical carrier.

In one embodiment, the pharmaceutical compositions deliver amounts effective for the treatment of cancer, including solid tumors and blood borne tumors.

In one embodiment, the pharmaceutical compositions deliver amounts effective for the prevention of cancer, including solid tumors and blood borne tumors.

In one embodiment, the pharmaceutical compositions deliver amounts effective for the amelioration of cancer, including solid tumors and blood borne tumors.

Also provided herein are combination therapies using one or more compounds or compositions provided herein, or an enantiomer or a mixture of enantiomers thereof, or an diastereomer or a mixture of diastereomers thereof, or a pharmaceutically acceptable salt, solvate, hydrate, co-crystal, clathrate, or polymorph thereof in combination with a therapy e.g., another pharmaceutical agent with activity against cancer or its symptoms. Examples of therapies within the scope of the methods include, but are not limited to, surgery, chemotherapy, radiation therapy, hormonal therapy, biological therapy, immunotherapy, and combinations thereof.

The compounds or compositions provided herein, or pharmaceutically acceptable derivatives thereof, may be administered simultaneously with, prior to, or after administration of one or more of the above therapies. Pharmaceutical compositions containing a compound provided herein and one or more of the above agents are also provided.

In certain embodiments, the compounds of the present invention may be included in an antibody drug conjugate. Antibody Drug Conjugates or ADCs are highly targeted biopharmaceutical drugs that combine monoclonal antibodies specific to surface antigens present on particular tumor cells with highly potent anti-cancer agents linked via a chemical linker.

In certain embodiments, provided herein are methods of treating, preventing or ameliorating cancer, including solid tumors and blood borne tumors, or one or more symptoms or causes thereof.

In certain embodiments, provided herein are methods of preventing cancer, including solid tumors and blood borne tumors, or one or more symptoms or causes thereof.

In certain embodiments, provided herein are methods of ameliorating cancer, including solid tumors and blood borne tumors, or one or more symptoms or causes thereof.

In certain embodiments, the blood borne tumor is leukemia. In certain embodiments, methods provided herein encompass methods of treating various forms of leukemias such as chronic lymphocytic leukemia, chronic myeloid leukemia, acute lymphocytic leukemia, acute myeloid leukemia and acute myeloblastic leukemia.

In certain embodiments, methods provided herein encompass methods of preventing various forms of leukemias such as chronic lymphocytic leukemia, chronic myeloid leukemia, acute lymphocytic leukemia, acute myeloid leukemia and acute myeloblastic leukemia.

In certain embodiments, methods provided herein encompass methods of managing various forms of leukemias such as chronic lymphocytic leukemia, chronic myeloid leukemia, acute lymphocytic leukemia, acute myeloid leukemia and acute myeloblastic leukemia.

The methods provided herein include treatment of leukemias that are relapsed, refractory or resistant.

The methods provided herein include prevention of leukemias that are relapsed, refractory or resistant.

The methods provided herein include management of leukemias that are relapsed, refractory or resistant.

In one embodiment, methods provided herein encompass methods of treating acute myeloid leukemia.

In one embodiment, methods provided herein encompass methods of preventing acute myeloid leukemia.

In one embodiment, methods provided herein encompass methods of managing acute myeloid leukemia.

In practicing the methods, effective amounts of the compounds or compositions containing therapeutically effective concentrations of the compounds are administered to an individual exhibiting the symptoms of the disease or disorder to be treated. The amounts are effective to ameliorate or eliminate one or more symptoms of the disease or disorder.

Further provided is a pharmaceutical pack or kit comprising one or more containers filled with one or more of the ingredients of the pharmaceutical compositions. Optionally associated with such container(s) can be a notice in the form prescribed by a governmental agency regulating the manufacture, use or sale of pharmaceuticals or biological products, which notice reflects approval by the agency of manufacture, use of sale for human administration. The pack or kit can be labeled with information regarding mode of administration, sequence of drug administration (e.g., separately, sequentially or concurrently), or the like.

These and other aspects of the subject matter described herein will become evident upon reference to the following detailed description.

DETAILED DESCRIPTION OF THE INVENTION

Provided herein are compounds of formula I.

Provided herein is an enantiomer of compounds of formula I.

Provided herein is a mixture of enantiomers of compounds of formula I.

Provided herein is a pharmaceutically acceptable salt of a compound of formula I.

Provided herein is a pharmaceutically acceptable solvate of a compound of formula I.

Provided herein is a pharmaceutically acceptable hydrate of a compound of formula I.

Provided herein is a pharmaceutically acceptable co-crystal of a compound of formula I.

Provided herein is a pharmaceutically acceptable clathrate of a compound of formula I.

Provided herein is a pharmaceutically acceptable polymorph of a compound of formula I.

Further provided are methods of treating cancer, including solid tumors blood borne tumors, and pharmaceutical compositions and dosage forms useful for such methods.

Further provided are methods of preventing cancer, including solid tumors blood borne tumors, and pharmaceutical compositions and dosage forms useful for such methods.

Further provided are methods of ameliorating cancer, including solid tumors blood borne tumors, and pharmaceutical compositions and dosage forms useful for such methods. The compounds, methods and compositions are described in detail in the sections below.

A. Definitions

Unless defined otherwise, all technical and scientific terms used herein have the same meaning as is commonly understood by one of ordinary skill in the art. All patents, applications, published applications and other publications are incorporated by reference in their entirety. In the event that there are a plurality of definitions for a term herein, those in this section prevail unless stated otherwise.

DEFINITIONS ABBREVIATIONS

The Following Abbreviations May be Used Herein
AcOH acetic acid
aq or aq. Aqueous
BOC or Boc tert-butyloxy carbonyl cpme cyclopentyl methyl ether
DCE 1,2-dichloroethane
DABCO 1,4-diazabicyclo[2.2.2]octane
DCM Dichloromethane
DMA N,N-Dimethylacetamide
DMAP 4-dimethylaminopyridine
DME 1,2-dimethoxyethane
DMF N,N-dimethylformamide
DMSO dimethyl sulfoxide
Dppf, DPPF or dppf 1,1'-bis(diphenylphosphino)ferrocene
eq or eq. or equiv. Equivalent
ESI or ES electrospray ionization
Et Ethyl
$Et_2O$ diethyl ether
EtOAc ethyl acetate
g Grams
h Hour
HPLC high pressure liquid chromatography
iPr Isopropyl
$iPr_2NEt$ or DIPEA N-ethyl diisopropylamine (Hunig's base)
KHMDS potassium hexamethyldisilazide
KOAc potassium acetate
Lawesson's reagent 2,4-bis(4-methoxyphenyl)-2,4-dithioxo-1,3,2,4-dithiadiphosphetane, 2,4-Bis-(4-methoxyphenyl)-1,3-dithia-2,4-diphosphetane 2,4-disulfide
LC MS, LCMS, LC-MS or liquid chromatography mass spectroscopy
LC/MS
LG Leaving group (e.g., halogen, mesylate, triflate)
LHMDS or LiHMDS lithium hexamethyldisilazide
m/z mass divided by charge
Me Methyl
MeCN Acetonitrile
MeOH Methanol
Met Metal species for cross-coupling (e.g., MgX, ZnX, $SnR_3$, $SiR_3$, $B(OR)_2$)
mg Milligrams
min Minutes
mL Milliliters
MS mass spectra
NaHMDS sodium hexamethyldisilazide
NBS N-bromosuccinimide
n-BuLi n-butyllithium
NCS N-chlorosuccinimide
NMR nuclear magnetic resonance
$Pd_2(dba)_3$ tris(dibenzylideneacetone)dipalladium(0)
$Pd(dppf)Cl_2 \cdot DCM$ [1,1'-Bis(diphenylphosphino)ferrocene]dichloropalladium(II), complex with dichloromethane
$Pd(PPh_3)_4$ Tetrakis(triphenylphosphine)palladium(0)
Ph Phenyl
PR or PG or Prot. group protecting group
rbf round-bottom flask
RP-HPLC reverse phase high pressure liquid chromatography
RT or rt room temperature
sat. or satd. saturated
SFC supercritical fluid chromatography
SPhos Pd G3 or SPhos G3 (2-Dicyclohexylphosphino-2',6'-dimethoxybiphenyl) [2-(2'-amino-1,1'-biphenyl)] palladium(II) methanesulfonate
TBAF tetra-n-butylammonium fluoride
TBTU N,N,N',N'-Tetramethyl-(9-(benzotriazol-1-yl)uronium tetrafluoroborate
t-BuOH tert-butanol
TEA or $Et_3N$ Triethylamine
TFA trifluoroacetic acid
THF Tetrahydrofuran
UV Ultraviolet The use of the terms "a," "an," "the," and similar referents in the context of describing the invention (especially in the context of the claims) are to be construed to cover both the singular and the plural, unless otherwise indicated. Recitation of ranges of values herein merely are intended to serve as a shorthand method of referring individually to each separate value falling within the range, unless otherwise indicated herein, and each separate value is incorporated into the specification as if it were individually recited herein. The use of any and all examples, or exemplary language (e.g., "such as") provided herein, is intended to better illustrate the invention and is not a limitation on the scope of the invention unless otherwise claimed. No language in the specification should be construed as indicating any non-claimed element as essential to the practice of the invention.

"Alkyl" refers to a straight or branched hydrocarbon chain group consisting solely of carbon and hydrogen atoms, containing no unsaturation, having from one to ten, one to eight, one to six or one to four carbon atoms, and which is attached to the rest of the molecule by a single bond, e.g., methyl, ethyl, n-propyl, 1-methylethyl (iso-propyl), n-butyl, n-pentyl, 1,1-dimethylethyl (t-butyl), and the like.

"Alkylene" and "alkylene chain" refer to a straight or branched divalent hydrocarbon chain consisting solely of carbon and hydrogen, containing no unsaturation and having from one to eight carbon atoms, e.g., methylene, ethylene, propylene, n-butylene and the like. The alkylene chain may be attached to the rest of the molecule through any two carbons within the chain.

"Alkenylene" or "alkenylene chain" refers to a straight or branched chain unsaturated divalent radical consisting solely of carbon and hydrogen atoms, having from two to eight carbon atoms, wherein the unsaturation is present only as double bonds and wherein the double bond can exist between any two carbon atoms in the chain, e.g., ethenylene, prop-1-enylene, but-2-enylene and the like. The alkenylene chain may be attached to the rest of the molecule through any two carbons within the chain.

"Alkoxy" refers to the group having the formula —OR wherein R is alkyl or haloalkyl. An "optionally substituted alkoxy" refers to the group having the formula —OR wherein R is an optionally substituted alkyl as defined herein.

"Amino" refers to a radical having the formula —NR'R' wherein R' and R' are each independently hydrogen, alkyl or haloalkyl. An "optionally substituted amino" refers to a radical having the formula—NR'R' wherein one or both of R' and R' are optionally substituted alkyl as defined herein.

"Aryl" refers to a group of carbocylic ring system, including monocyclic, bicyclic, tricyclic, tetracyclic $C_6$-$C_{18}$ ring systems, wherein at least one of the rings is aromatic. The aryl may be fully aromatic, examples of which are phenyl, naphthyl, anthracenyl, acenaphthylenyl, azulenyl, fluorenyl, indenyl and pyrenyl. The aryl may also contain an aromatic ring in combination with a non-aromatic ring, examples of which are acenaphene, indene, and fluorene.

"Cycloalkyl" refers to a stable monovalent monocyclic or bicyclic hydrocarbon group consisting solely of carbon and hydrogen atoms, having from three to ten carbon atoms which is saturated, e.g., cyclopropyl, cyclobutyl, cyclopentyl, cyclohexyl, decalinyl, norbornane, norbornene, adamantyl, bicyclo[2.2.2]octane and the like.

"Halo, "halogen" or "halide" refers to F, Cl, Br or I.

"Haloalkyl" refers to an alkyl group, in certain embodiments, $C_{1-6}$alkyl group in which one or more of the hydrogen atoms are replaced by halogen. Such groups include, but are not limited to, chloromethyl, trifluoromethyl 1-chloro-2-fluoroethyl, 2,2-difluoroethyl, 2-fluoropropyl, 2-fluoropropan-2-yl, 2,2,2-trifluoroethyl, 1,1-difluoroethyl, 1,3-difluoro-2-methylpropyl, 2,2-difluorocyclopropyl, (trifluoromethyl)cyclopropyl, 4,4-difluorocyclohexyl and 2,2,2-trifluoro-1,1-dimethylethyl.

"Heterocycle" or "Heterocyclyl" refers to a stable 3- to 15-membered non-aromatic ring radical which consists of carbon atoms and from one to five heteroatoms selected from a group consisting of nitrogen, oxygen and sulfur. In one embodiment, the heterocyclic ring system radical may be a monocyclic, bicyclic or tricyclic ring or tetracyclic ring system, which may include fused or bridged ring systems; and the nitrogen or sulfur atoms in the heterocyclic ring system radical may be optionally oxidized; the nitrogen atom may be optionally quaternized; and the heterocyclyl radical may be partially or fully saturated. The heterocyclic ring system may be attached to the main structure at any heteroatom or carbon atom which results in the creation of a stable compound. Exemplary heterocylic radicals include, morpholinyl, piperidinyl, piperazinyl, pyranyl, pyrrolidinyl, oxetanyl, azetidinyl, quinuclidinyl, octahydroquinolizinyl, decahydroquinolizinyl, azabicyclo[3.2.1]octanyl, azabicyclo[2.2.2]octanyl, isoindolinyl, indolinyl and others.

"Heteroaryl" refers to a heterocyclyl group as defined above which is aromatic. The heteroaryl groups include, but are not limited to monocyclyl, bicyclyl and tricyclyl groups, and may be attached to the main structure at any heteroatom or carbon atom which results in the creation of a stable compound. Examples of such heteroaryl groups include, but are not limited to: furanyl, imidazolyl, oxazolyl, isoxazolyl, pyrimidinyl, pyridinyl, pyridazinyl, thiazolyl, thienyl, benzimidazolyl, imidazo[4,5-b]pyridinyl, imidazo[1,2-a]pyridinyl, imidazo[1,2-b]pyridazinyl, imidazo[1,2-a]pyrazinyl and others.

"$EC_{50}$" refers to an amount, concentration or dosage of a particular test compound that achieves a 50% potency or effect of a maximal response, such as cell growth or proliferation measured via any of the in vitro or cell-based assay described herein.

"$IC_{50}$" refers to an amount, concentration or dosage of a particular test compound that achieves a 50% inhibition of a maximal response, such as cell growth or proliferation, measured via any of the in vitro or cell-based assay described herein.

Pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethyl-benzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates, fumarates and organic sulfonates.

As used herein and unless otherwise indicated, the term "hydrate" means a compound provided herein or a salt thereof, that further includes a stoichiometric or non-stoichiometeric amount of water bound by non-covalent intermolecular forces.

As used herein and unless otherwise indicated, the term "solvate" means a solvate formed from the association of one or more solvent molecules to a compound provided herein. The term "solvate" includes hydrates (e.g., monohydrate, dihydrate, trihydrate, tetrahydrate and the like).

Unless stated otherwise specifically described in the specification, it is understood that the substitution can occur on any atom of the alkyl, alkenyl, alkynyl, cycloalkyl, heterocyclyl, aryl or heteroaryl group.

Where the number of any given substituent is not specified (e.g., haloalkyl), there may be one or more substituents present. For example, "haloalkyl" may include one or more of the same or different halogens.

When the groups described herein, with the exception of alkyl group, are said to be "substituted," they may be substituted with any appropriate substituent or substituents. Illustrative examples of substituents are those found in the exemplary compounds and embodiments disclosed herein, as well as halogen (chloro, iodo, bromo, or fluoro); alkyl; hydroxyl; alkoxy; alkoxyalkyl; amino; alkylamino; carboxy; nitro; cyano; thiol; thioether; imine; imide; amidine; guanidine; enamine; aminocarbonyl; acylamino; phosphonate; phosphine; thiocarbonyl; sulfinyl; sulfone; sulfonamide; ketone; aldehyde; ester; urea; urethane; oxime; hydroxyl amine; alkoxyamine; aryloxyamine, aralkoxyamine; N-oxide; hydrazine; hydrazide; hydrazone; azide; isocyanate; isothiocyanate; cyanate; thiocyanate; oxygen (=O); $B(OH)_2$, O(alkyl)aminocarbonyl; cycloalkyl, which may be monocyclic or fused or non-fused polycyclic (e.g., cyclopropyl, cyclobutyl, cyclopentyl, or cyclohexyl), or a heterocyclyl, which may be monocyclic or fused or non-fused polycyclic (e.g., pyrrolidyl, piperidyl, piperazinyl, morpholinyl, or thiazinyl); monocyclic or fused or non-fused polycyclic aryl or heteroaryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridinyl, quinolinyl, isoquinolinyl, acridinyl, pyrazinyl, pyridazinyl, pyrimidinyl, benzimidazolyl, benzothiophenyl, or benzofuranyl) aryloxy; aralkyloxy; heterocyclyloxy; and heterocyclyl alkoxy. When the alkyl groups described herein are said to be "substituted," they may be substituted with any substituent or substituents as those found in the exemplary compounds and embodiments disclosed herein, as well as halogen (chloro, iodo, bromo, or fluoro); alkyl; hydroxyl; alkoxy; alkoxyalkyl; amino; alkylamino; carboxy; nitro; cyano; thiol; thioether; imine; imide; amidine; guanidine; enamine; aminocarbonyl; acylamino; phosphonate; phosphine; thiocarbonyl; sulfinyl; sulfone; sulfonamide; ketone; aldehyde; ester; urea; urethane; oxime; hydroxyl amine; alkoxyamine; aryloxyamine, aralkoxyamine; N-oxide; hydrazine; hydrazide; hydrazone; azide; isocyanate; isothiocyanate; cyanate; thiocyanate; $B(OH)_2$, or O(alkyl)aminocarbonyl.

Unless specifically stated otherwise, where a compound may assume alternative tautomeric, regioisomeric and/or stereoisomeric forms, all alternative isomers are intended to be encompassed within the scope of the claimed subject matter. For example, where a compound is described as having one of two tautomeric forms, it is intended that both tautomers be encompassed herein.

Thus, the compounds provided herein may be enantiomerically pure, or be stereoisomeric or diastereomeric mixtures.

It is to be understood that the compounds provided herein may contain chiral centers. Such chiral centers may be of either the (R) or (S) configuration, or may be a mixture thereof. It is to be understood that the chiral centers of the compounds provided herein may undergo epimerization in vivo. As such, one of skill in the art will recognize that administration of a compound in its (R) form is equivalent, for compounds that undergo epimerization in vivo, to administration of the compound in its (S) form.

Optically active (+) and (−), (R)- and (S)-, or (D)- and (L)-isomers may be prepared using chiral synthons or chiral reagents, or resolved using conventional techniques, such as chromatography on a chiral stationary phase.

In the description herein, if there is any discrepancy between a chemical name and chemical structure, the structure controls.

As used herein and unless otherwise indicated, the terms "treat," "treating" and "treatment" refer to alleviating or reducing the severity of a symptom associated with the disease or condition being treated.

The term "prevention" includes the inhibition of a symptom of the particular disease or disorder. In some embodiments, patients with familial history of cancer, including solid tumors and blood borne tumors, are candidates for preventive regimens. Generally, the term "preventing" refers to administration of the drug prior to the onset of symptoms, particularly to patients at risk of cancer, including solid tumors and blood borne tumors.

As used herein and unless otherwise indicated, the term "managing" encompasses preventing the recurrence of the particular disease or disorder in a patient who had suffered from it, lengthening the time a patient who had suffered from the disease or disorder remains in remission, reducing mortality rates of the patients, and/or maintaining a reduction in severity or avoidance of a symptom associated with the disease or condition being managed.

As used herein, "subject" is an animal, typically a mammal, including a human, such as a human patient.

As used herein, the term "tumor," refers to all neoplastic cell growth and proliferation, whether malignant or benign, and all pre-cancerous and cancerous cells and tissues. "Neoplastic," as used herein, refers to any form of dysregulated or unregulated cell growth, whether malignant or benign, resulting in abnormal tissue growth. Thus, "neoplastic cells" include malignant and benign cells having dysregulated or unregulated cell growth.

As used herein, "hematologic malignancy" refers to cancer of the body's blood-forming and immune system—the bone marrow and lymphatic tissue. Such cancers include leukemias, lymphomas (Non-Hodgkin's Lymphoma), Hodgkin's disease (also called Hodgkin's Lymphoma) and myeloma.

The term "leukemia" refers to malignant neoplasms of the blood-forming tissues. The leukemia includes, but is not limited to, chronic lymphocytic leukemia, chronic myelocytic leukemia, acute lymphoblastic leukemia, acute myeloid leukemia, and acute myeloblastic leukemia. The leukemia can be relapsed, refractory or resistant to conventional therapy.

As used herein, "promyelocytic leukemia" or "acute promyelocytic leukemia" refers to a malignancy of the bone marrow in which there is a deficiency of mature blood cells in the myeloid line of cells and an excess of immature cells called promyelocytes. It is usually marked by an exchange of regions of chromosomes 15 and 17.

As used herein, "acute lymphocytic leukemia (ALL)", also known as "acute lymphoblastic leukemia" refers to a malignant disease caused by the abnormal growth and development of early nongranular white blood cells, or lymphocytes.

As used herein, "T-cell leukemia" refers to a disease in which certain cells of the lymphoid system called T lymphocytes or T cells are malignant. T cells are white blood cells that normally can attack virus-infected cells, foreign cells, and cancer cells and produce substances that regulate the immune response.

The term "relapsed" refers to a situation where patients who have had a remission of leukemia after therapy have a return of leukemia cells in the marrow and a decrease in normal blood cells.

The term "refractory or resistant" refers to a circumstance where patients, even after intensive treatment, have residual leukemia cells in their marrow.

As used herein, and unless otherwise specified, the terms "therapeutically effective amount" and "effective amount" of a compound refer to an amount sufficient to provide a therapeutic benefit in the treatment, prevention and/or management of a disease, to delay or minimize one or more symptoms associated with the disease or disorder to be treated. The terms "therapeutically effective amount" and "effective amount" can encompass an amount that improves overall therapy, reduces or avoids symptoms or causes of disease or disorder, or enhances the therapeutic efficacy of another therapeutic agent.

The terms "co-administration" and "in combination with" include the administration of two therapeutic agents (for example, a compound provided herein and another anti-cancer agent) either simultaneously, concurrently or sequentially with no specific time limits. In one embodiment, both agents are present in the cell or in the patient's body at the same time or exert their biological or therapeutic effect at the same time. In one embodiment, the two therapeutic agents are in the same composition or unit dosage form. In another embodiment, the two therapeutic agents are in separate compositions or unit dosage forms.

The term "the supportive care agent" refers to any substance that treats, prevents or manages an adverse effect from treatment with the compound of Formula I.

The term "biological therapy" refers to administration of biological therapeutics such as cord blood, stem cells, growth factors and the like.

The term "about," as used herein, unless otherwise indicated, refers to a value that is no more than 10% above or below the value being modified by the term. For example, the term "about 10 mg/m$^2$" means a range of from 9 mg/m$^2$ to 11 mg/m$^2$.

"Anti-cancer agents" refers to anti-metabolites (e.g., 5-fluoro-uracil, methotrexate, fludarabine), antimicrotubule agents (e.g., vinca alkaloids such as vincristine, vinblastine; taxanes such as paclitaxel, docetaxel), alkylating agents (e.g., cyclophosphamide, melphalan, carmustine, nitrosoureas such as bischloroethylnitrosurea and hydroxyurea), platinum agents (e.g. cisplatin, carboplatin, oxaliplatin, JM-216 or satraplatin, CI-973), anthracyclines (e.g., doxorubicin, daunorubicin), antitumor antibiotics (e.g., mitomycin, idarubicin, adriamycin, daunomycin), topoisomerase inhibitors (e.g., etoposide, camptothecins), anti-angiogenesis agents (e.g. Sutent® and Bevacizumab) or any other cytotoxic agents, (estramustine phosphate, prednimustine), hormones or hormone agonists, antagonists, partial agonists or partial antagonists, kinase inhibitors, and radiation treatment.

As used herein, the abbreviations for any protective groups, amino acids and other compounds, are, unless indicated otherwise, in accord with their common usage, recognized abbreviations, or the IUPAC-IUB Commission on Biochemical Nomenclature (see, *Biochem.* 1972, 11:942-944).

B. Compounds

Embodiments

The embodiments listed below are presented in numbered form for convenience and for ease and clarity of reference in referring back to multiple embodiments.
1. In a first embodiment, the present invention comprises a compound having a Formula (I),

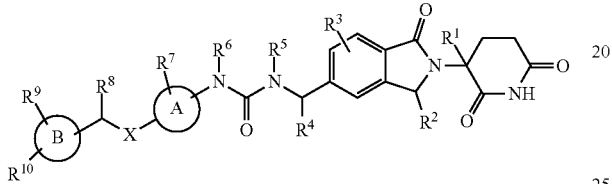

or a pharmaceutically acceptable salt, solvate, hydrate, co-crystal, clathrate, polymorph or tautomer thereof, a pharmaceutically acceptable salt of the polymorph or tautomer, a stereoisomer of any of the foregoing, or a mixture thereof, wherein:
A is independently selected from an unsubstituted or substituted 3 to 12 membered cycloalkyl, 4 to 12 membered heterocyclic, 5 to 12 membered aryl, or a 5 to 12 membered heteroaryl ring;
B is independently selected from an unsubstituted or substituted 3 to 12 membered cycloalkyl, 4 to 12 membered heterocyclic, 5 to 12 membered aryl or a 5 to 12 membered heteroaryl ring;
X is independently selected from O or —$NR^{11}$;
$R^1$ is independently selected from hydrogen, halogen, —$C_1$-$C_6$ alkyl or a 3 to 6 membered cycloalkyl;
$R^2$ is independently selected from hydrogen, halogen, —C(O), —$C_1$-$C_6$ alkyl, a 3 to 6 membered cycloalkyl, wherein the alkyl or cycloalkyl may be optionally substituted with —$R^{11}$, —$N(R^{11}R^{11})$, —$NHR^{11}$ or —$OR^{11}$;
$R^3$ is independently selected from hydrogen, halogen, —$OR^{11}$, —$N(R^{11}R^{11})$, —$NHR^{11}$, —$C_1$-$C_6$ alkyl, a 3 to 6 membered cycloalkyl, 4 to 12 membered heterocyclic, 5 to 12 membered aryl or a 5 to 12 membered heteroaryl ring, wherein the alkyl, cycloalkyl, heterocyclic and heteroaryl may be optionally substituted with —$R^{11}$, —$N(R^{11}R^{11})$, —$NHR^{11}$ or —$OR^{11}$;
$R^4$ is independently selected from hydrogen, halogen, —$C_1$-$C_6$ alkyl, a 3 to 6 membered cycloalkyl, 4 to 12 membered heterocyclic, 5 to 12 membered aryl or a 5 to 12 membered heteroaryl ring, wherein the alkyl, cycloalkyl, heterocyclic and heteroaryl may be optionally substituted with —$R^{11}$, —$NHR^{11}$ or —$OR^{11}$;
$R^5$ is independently selected from hydrogen, —$C_1$-$C_6$ alkyl, a 3 to 6 membered cycloalkyl, 4 to 12 membered heterocyclic, 5 to 12 membered aryl or a 5 to 12 membered heteroaryl ring, wherein the alkyl, cycloalkyl, heterocyclic and heteroaryl may be optionally substituted with —$R^{11}$, —$N(R^{11}R^{11})$, —$NHR^1$ or —$OR^{11}$;

$R^6$ is independently selected from hydrogen, —$C_1$-$C_6$ alkyl, a 3 to 6 membered cycloalkyl, 4 to 12 membered heterocyclic, 5 to 12 membered aryl or a 5 to 12 membered heteroaryl ring, wherein the alkyl, cycloalkyl, heterocyclic and heteroaryl may be optionally substituted with —$R^{11}$, —$N(R^{11}R^{11})$, —$NHR^{11}$ or —$OR^{11}$;
wherein two $R^5$ and $R^6$ substituents together with the carbon atoms they are attached to, may join to form a 5 or 6 membered ring that may be saturated, partially saturated,
and may further optionally be substituted with 1 or 2 $R^{11}$ substituents;
$R^7$ is independently selected from hydrogen, halogen, —$OR^{11}$, —$C_1$-$C_6$ alkyl, —($C_1$-$C_6$ haloalkyl), —($C_1$-$C_6$ alkyl)-O—($C_1$-$C_6$ alkyl), —$NHR^{11}$, —$N(R^{11}R^{11})$, —CN, 3 to 12 membered cycloalkyl, 4 to 12 membered heterocyclic, 5 to 12 membered aryl or a 5 to 12 membered heteroaryl ring, —$C_2$-$C_6$ alkenyl, —O—($C_1$-$C_6$ haloalkyl)-O—($C_1$-$C_6$ alkyl), —C(═O)—($C_1$-$C_6$ alkyl), —C(═O)OH, —C(═O)—O—($C_1$-$C_6$ alkyl), —C(═O)$NH_2$, —C(═O)NH($R^{11}$), —C(═O)N($R^{11}R^{11}$), —S(O)$_2R^{11}$, —S(═O)$R^{11}$, —$SR^{11}$, —S(═O)$_2NH_2$, —S(═O)$_2$NH($C_1$-$C_6$ alkyl), or —S(═O)$_2$N($C_1$-$C_6$ alkyl)$_2$,
wherein the alkyl, haloalkyl, cycloalkyl, heterocyclic, aryl, or heteroaryl may be optionally substituted with —$R^{11}$, —$N(R^{11}R^{11})$, —$NHR^{11}$ or —$OR^{11}$;
$R^8$ is independently selected from hydrogen, halogen or a —$C_1$-$C_6$ alkyl, optionally substituted with —$R^{11}$, —$N(R^{11}R^{11})$, —$NHR^{11}$ or —$OR^{11}$;
$R^9$ is independently selected from hydrogen, halogen, —$OR^{11}$, —$C_1$-$C_6$ alkyl, —($C_1$-$C_6$ haloalkyl), —($C_1$-$C_6$ alkyl)-O—($C_1$-$C_6$ alkyl), —$NHR^{11}$, —$N(R^{11}R^{11})$, —CN, 3 to 12 membered cycloalkyl, 4 to 12 membered heterocyclic, 5 to 12 membered aryl or a 5 to 12 membered heteroaryl ring, —$C_2$-$C_6$ alkenyl, —O—($C_1$-$C_6$ haloalkyl)-O—($C_1$-$C_6$ alkyl), —C(═O)—($C_1$-$C_6$ alkyl), —C(═O)OH, —C(═O)—O—($C_1$-$C_6$ alkyl), —C(═O)$NH_2$, —C(═O)NH($R^{11}$), —C(═O)N($R^{11}R^{11}$), —S(O)$_2R^{11}$, —S(═O)$R^{11}$, —$SR^{11}$, —S(═O)$_2NH_2$, —S(═O)$_2$NH($C_1$-$C_6$ alkyl), or —S(═O)$_2$N($C_1$-$C_6$ alkyl)$_2$,
wherein the alkyl, haloalkyl, cycloalkyl, heterocyclic, aryl, or heteroaryl may be optionally substituted with —$R^{11}$, —$N(R^{11}R^{11})$, —$NHR^{11}$ or —$OR^{11}$;
$R^{10}$ is independently selected from hydrogen, halogen, —$OR^{11}$, —$C_1$-$C_6$ alkyl, —($C_1$-$C_6$ haloalkyl), —($C_1$-$C_6$ alkyl)-O—($C_1$-$C_6$ alkyl), —$NHR^{11}$, —$N(R^{11}R^{11})$, —CN, 3 to 12 membered cycloalkyl, 4 to 12 membered heterocyclic, 5 to 12 membered aryl or a 5 to 12 membered heteroaryl ring, —$C_2$-$C_6$ alkenyl, —O—($C_1$-$C_6$ haloalkyl)-O—($C_1$-$C_6$ alkyl), —C(═O)—($C_1$-$C_6$ alkyl), —C(═O)OH, —C(═O)—O—($C_1$-$C_6$ alkyl), —C(═O)$NH_2$, —C(═O)NH($R^{11}$), —C(═O)N($R^{11}R^{11}$), —S(O)$_2R^{11}$, —S(═O)$R^{11}$, —$SR^{11}$, —S(═O)$_2NH_2$, —S(═O)$_2$NH($C_1$-$C_6$ alkyl), or —S(═O)$_2$N($C_1$-$C_6$ alkyl)$_2$,
wherein the alkyl, haloalkyl, cycloalkyl, heterocyclic, aryl, or heteroaryl may be optionally substituted with —$R^{11}$, —$N(R^{11}R^{11})$, —$NHR^{11}$ or —$OR^{11}$;
$R^{11}$ is independently selected from hydrogen, halogen, —$C_1$-$C_6$ alkyl, —$C_2$-$C_6$alkenyl, —$C_1$-$C_6$ haloalkyl, a 3 to 12 membered cycloalkyl, 4 to 12 membered heterocyclic, 5 to 12 membered aryl or a 5 to 12 membered heteroaryl ring; wherein the alkyl, alkenyl, haloalkyl, cycloalkyl, heterocyclic, aryl or heteroaryl ring in $R^{11}$ are each independently unsubstituted or substituted with 1, 2, or 3 $R^{12}$ substituents;

$R^{12}$ in each instance is independently selected from hydrogen, —$C_1$-$C_6$ alkyl, halogen, —OH, —O—($C_1$-$C_6$ alkyl)-, —$NH_2$, a 3 to 12 membered alkyl, 5 to 12 membered heterocyclic, 5 to 12 membered aryl or 5 to 12 membered heteroaryl ring; wherein the alkyl, alkenyl, haloalkyl, cycloalkyl, heterocyclic, aryl or heteroaryl ring in $R^{12}$ are each independently unsubstituted or substituted with $R^{13}$;

$R^{13}$ is independently hydrogen, halo, —$C_1$-$C_6$ alkyl, —$C_1$-$C_6$ haloalkyl, —$C_1$-$C_6$ alkoxyalkyl, oxo, hydroxyl or —$C_1$-$C_6$ alkoxy; and further wherein two $R^9$ and $R^{10}$ substituents on adjacent carbon atoms of the A or B group may join to form a 5 or 6 membered ring that may be saturated, partially saturated, or aromatic;

and may further optionally be substituted with 1 or 2 $R^{13}$ substituents and may include an oxo substituent if the ring is not an aromatic ring;

wherein the heterocyclic and heteroaryl cyclic ring in each A, B, $R^3$, $R^4$, $R^5$, $R^6$, $R^7$, $R^9$, $R^{10}$, $R^{11}$, $R^{12}$ and $R^{13}$ may include 1, 2 or 3 heteroatoms independently selected from O, N or S.

2. The compound of embodiment 1 having the Formula I or a pharmaceutically acceptable salt, solvate, hydrate, co-crystal, clathrate, polymorph or tautomer thereof, a pharmaceutically acceptable salt of the polymorph or tautomer, a stereoisomer of any of the foregoing, or a mixture thereof, wherein X is O.

3. The compound of embodiment 1 having the Formula I or a pharmaceutically acceptable salt, solvate, hydrate, co-crystal, clathrate, polymorph or tautomer thereof, a pharmaceutically acceptable salt of the polymorph or tautomer, a stereoisomer of any of the foregoing, or a mixture thereof, wherein X is —$NR^{11}$.

4. The compound of any one of embodiments 1-3, having the Formula I or a pharmaceutically acceptable salt, solvate, hydrate, co-crystal, clathrate, polymorph or tautomer thereof, a pharmaceutically acceptable salt of the polymorph or tautomer, a stereoisomer of any of the foregoing, or a mixture thereof, wherein A is substituted with 1 or 2 $R^7$ substituents.

5. The compound of any one of embodiments 1-4, or a pharmaceutically acceptable salt, solvate, hydrate, co-crystal, clathrate, polymorph or tautomer thereof, a pharmaceutically acceptable salt of the polymorph or tautomer, a stereoisomer of any of the foregoing, or a mixture thereof, wherein $R^7$ is selected from hydrogen, halogen or —$C_1$-$C_6$ alkyl.

6. The compound of any one of embodiments 1-5, or a pharmaceutically acceptable salt, solvate, hydrate, co-crystal, clathrate, polymorph or tautomer thereof, a pharmaceutically acceptable salt of the polymorph or tautomer, a stereoisomer of any of the foregoing, or a mixture thereof, wherein $R^7$ is independently selected from hydrogen, F, Cl, or methyl.

7. The compound of any one of embodiments 1-6, or a pharmaceutically acceptable salt, solvate, hydrate, co-crystal, clathrate, polymorph or tautomer thereof, a pharmaceutically acceptable salt of the polymorph or tautomer, a stereoisomer of any of the foregoing, or a mixture thereof, wherein $R^7$ is hydrogen.

8. The compound of any one of embodiments 1-6, or a pharmaceutically acceptable salt, solvate, hydrate, co-crystal, clathrate, polymorph or tautomer thereof, a pharmaceutically acceptable salt of the polymorph or tautomer, a stereoisomer of any of the foregoing, or a mixture thereof, wherein $R^7$ is F.

9. The compound of any one of embodiments 1-6, or a pharmaceutically acceptable salt, solvate, hydrate, co-crystal, clathrate, polymorph or tautomer thereof, a pharmaceutically acceptable salt of the polymorph or tautomer, a stereoisomer of any of the foregoing, or a mixture thereof, wherein $R^7$ is Cl.

10. The compound of any one of embodiments 1-6, or a pharmaceutically acceptable salt, solvate, hydrate, co-crystal, clathrate, polymorph or tautomer thereof, a pharmaceutically acceptable salt of the polymorph or tautomer, a stereoisomer of any of the foregoing, or a mixture thereof, wherein $R^7$ is methyl.

11. The compound of any one of embodiments 1-10, or a pharmaceutically acceptable salt, solvate, hydrate, co-crystal, clathrate, polymorph or tautomer thereof, a pharmaceutically acceptable salt of the polymorph or tautomer, a stereoisomer of any of the foregoing, or a mixture thereof, wherein A is phenyl,

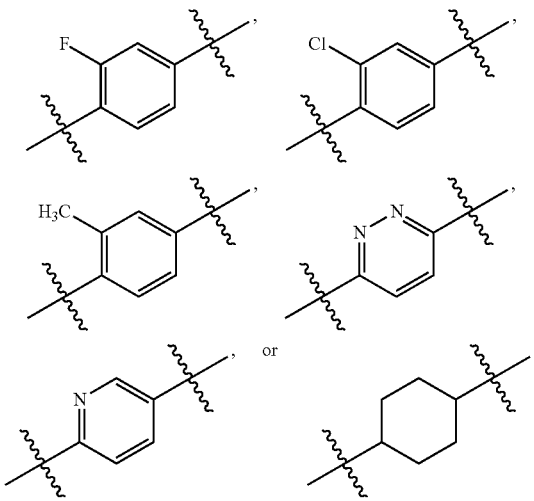

12. The compound of any one of embodiments 1-11 or 9, or a pharmaceutically acceptable salt, solvate, hydrate, co-crystal, clathrate, polymorph or tautomer thereof, a pharmaceutically acceptable salt of the polymorph or tautomer, a stereoisomer of any of the foregoing, or a mixture thereof, wherein A is phenyl.

13. The compound of any one of embodiments 1-11, or a pharmaceutically acceptable salt, solvate, hydrate, co-crystal, clathrate, polymorph or tautomer thereof, a pharmaceutically acceptable salt of the polymorph or tautomer, a stereoisomer of any of the foregoing, or a mixture thereof, wherein A is

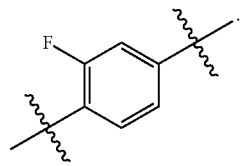 [SMILES: *c1ccc(*)c(F)c1]

14. The compound of any one of embodiments 1-11, or a pharmaceutically acceptable salt, solvate, hydrate, co-crystal, clathrate, polymorph or tautomer thereof, a pharmaceutically acceptable salt of the polymorph or tautomer, a stereoisomer of any of the foregoing, or a mixture thereof, wherein A is

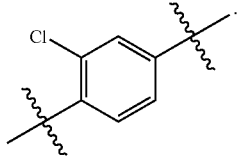

15. The compound of any one of embodiments 1-11, or a pharmaceutically acceptable salt, solvate, hydrate, co-crystal, clathrate, polymorph or tautomer thereof, a pharmaceutically acceptable salt of the polymorph or tautomer, a stereoisomer of any of the foregoing, or a mixture thereof, wherein A is

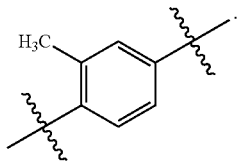 [SMILES: *c1ccc(*)c(C)c1]

16. The compound of any one of embodiments 1-11, or a pharmaceutically acceptable salt, solvate, hydrate, co-crystal, clathrate, polymorph or tautomer thereof, a pharmaceutically acceptable salt of the polymorph or tautomer, a stereoisomer of any of the foregoing, or a mixture thereof, wherein A is

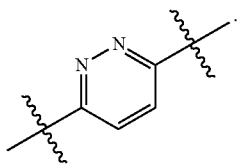 [SMILES: *c1ccc(*)nn1]

17. The compound of any one of embodiments 1-11, or a pharmaceutically acceptable salt, solvate, hydrate, co-crystal, clathrate, polymorph or tautomer thereof, a pharmaceutically acceptable salt of the polymorph or tautomer, a stereoisomer of any of the foregoing, or a mixture thereof, wherein A is

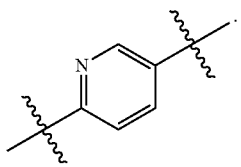 [SMILES: *c1ccc(*)nc1]

18. The compound of any one of embodiments 1-11, or a pharmaceutically acceptable salt, solvate, hydrate, co-crystal, clathrate, polymorph or tautomer thereof, a pharmaceutically acceptable salt of the polymorph or tautomer, a stereoisomer of any of the foregoing, or a mixture thereof, wherein A is

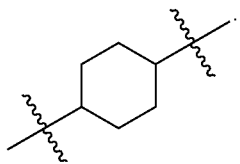 [SMILES: *C1CCC(*)CC1]

19. The compound of any one of embodiments 1-18 or a pharmaceutically acceptable salt, solvate, hydrate, co-crystal, clathrate, polymorph or tautomer thereof, a pharmaceutically acceptable salt of the polymorph or tautomer, a stereoisomer of any of the foregoing, or a mixture thereof, wherein B is independently selected from a substituted or unsubstituted phenyl,

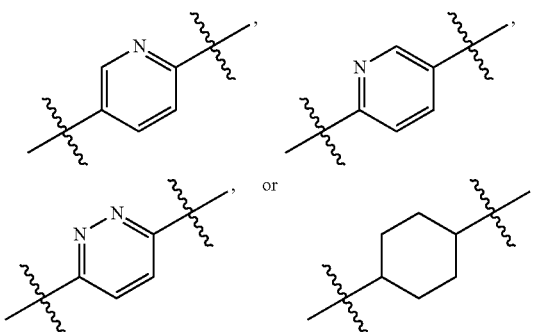

20. The compound of any one of embodiments 1-19 having the Formula I or a pharmaceutically acceptable salt, solvate, hydrate, co-crystal, clathrate, polymorph or tautomer thereof, a pharmaceutically acceptable salt of the polymorph or tautomer, a stereoisomer of any of the foregoing, or a mixture thereof, wherein B is substituted with one or more $R^9$ substituents.

21. The compound of any one of embodiments 1-20, or a pharmaceutically acceptable salt, solvate, hydrate, co-crystal, clathrate, polymorph or tautomer thereof, a pharmaceutically acceptable salt of the polymorph or tautomer, a stereoisomer of any of the foregoing, or a mixture thereof, wherein $R^9$ is selected from hydrogen, halogen, —$OR^{11}$, —$C_1$-$C_6$ alkyl, —($C_1$-$C_6$ haloalkyl), —($C_1$-$C_6$ alkyl)-$NH_2$, —($C_1$-$C_6$ alkyl)-OH, —CN, or 3 to 12 membered cycloalkyl.

22. The compound of any one of embodiments 1-21 or a pharmaceutically acceptable salt, solvate, hydrate, co-crystal, clathrate, polymorph or tautomer thereof, a pharmaceutically acceptable salt of the polymorph or tautomer, a stereoisomer of any of the foregoing, or a mixture thereof, wherein $R^9$ is selected from H, —OH, Cl, F, —$CH_3$, —$CH_2CH_3$, —$(CH_2)_2CH_3$, —CH$(CH_3)_2$, —$(CH_2)$OH, —$CH_2NH_2$, —CN, —$OCH_3$, —$OCH(CH_3)_2$, —$OCHF_2$,

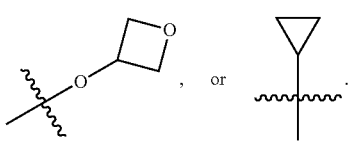

23. The compound of any one of embodiments 1-21 or a pharmaceutically acceptable salt, solvate, hydrate, co-crystal, clathrate, polymorph or tautomer thereof, a pharmaceutically acceptable salt of the polymorph or tautomer, a stereoisomer of any of the foregoing, or a mixture thereof, wherein $R^9$ is H.

24. The compound of any one of embodiments 1-21 or a pharmaceutically acceptable salt, solvate, hydrate, co-crystal, clathrate, polymorph or tautomer thereof, a pharmaceutically acceptable salt of the polymorph or tautomer, a stereoisomer of any of the foregoing, or a mixture thereof, wherein $R^9$ is —OH.

25. The compound of any one of embodiments 1-21 or a pharmaceutically acceptable salt, solvate, hydrate, co-crystal, clathrate, polymorph or tautomer thereof, a pharmaceutically acceptable salt of the polymorph or tautomer, a stereoisomer of any of the foregoing, or a mixture thereof, wherein $R^9$ is Cl.

26. The compound of any one of embodiments 1-21 or a pharmaceutically acceptable salt, solvate, hydrate, co-crystal, clathrate, polymorph or tautomer thereof, a pharmaceutically acceptable salt of the polymorph or tautomer, a stereoisomer of any of the foregoing, or a mixture thereof, wherein $R^9$ is F.

27. The compound of any one of embodiments 1-21 or a pharmaceutically acceptable salt, solvate, hydrate, co-crystal, clathrate, polymorph or tautomer thereof, a pharmaceutically acceptable salt of the polymorph or tautomer, a stereoisomer of any of the foregoing, or a mixture thereof, wherein $R^9$ is —$CH_3$.

28. The compound of any one of embodiments 1-21 or a pharmaceutically acceptable salt, solvate, hydrate, co-crystal, clathrate, polymorph or tautomer thereof, a pharmaceutically acceptable salt of the polymorph or tautomer, a stereoisomer of any of the foregoing, or a mixture thereof, wherein $R^9$ is —$CH_2CH_3$.

29. The compound of any one of embodiments 1-21 or a pharmaceutically acceptable salt, solvate, hydrate, co-crystal, clathrate, polymorph or tautomer thereof, a pharmaceutically acceptable salt of the polymorph or tautomer, a stereoisomer of any of the foregoing, or a mixture thereof, wherein $R^9$ is —$(CH_2)_2CH_3$.

30. The compound of any one of embodiments 1-21 or a pharmaceutically acceptable salt, solvate, hydrate, co-crystal, clathrate, polymorph or tautomer thereof, a pharmaceutically acceptable salt of the polymorph or tautomer, a stereoisomer of any of the foregoing, or a mixture thereof, wherein $R^9$ is —$CH(CH_3)_2$.

31. The compound of any one of embodiments 1-21 or a pharmaceutically acceptable salt, solvate, hydrate, co-crystal, clathrate, polymorph or tautomer thereof, a pharmaceutically acceptable salt of the polymorph or tautomer, a stereoisomer of any of the foregoing, or a mixture thereof, wherein $R^9$ is —$(CH_2)OH$.

32. The compound of any one of embodiments 1-21 or a pharmaceutically acceptable salt, solvate, hydrate, co-crystal, clathrate, polymorph or tautomer thereof, a pharmaceutically acceptable salt of the polymorph or tautomer, a stereoisomer of any of the foregoing, or a mixture thereof, wherein $R^9$ is —$CH_2NH_2$.

33. The compound of any one of embodiments 1-21 or a pharmaceutically acceptable salt, solvate, hydrate, co-crystal, clathrate, polymorph or tautomer thereof, a pharmaceutically acceptable salt of the polymorph or tautomer, a stereoisomer of any of the foregoing, or a mixture thereof, wherein $R^9$ is —CN.

34. The compound of any one of embodiments 1-21 or a pharmaceutically acceptable salt, solvate, hydrate, co-crystal, clathrate, polymorph or tautomer thereof, a pharmaceutically acceptable salt of the polymorph or tautomer, a stereoisomer of any of the foregoing, or a mixture thereof, wherein $R^9$ is —$OCH_3$.

35. The compound of any one of embodiments 1-21 or a pharmaceutically acceptable salt, solvate, hydrate, co-crystal, clathrate, polymorph or tautomer thereof, a pharmaceutically acceptable salt of the polymorph or tautomer, a stereoisomer of any of the foregoing, or a mixture thereof, wherein $R^9$ is —$OCH(CH_3)_2$.

36. The compound of any one of embodiments 1-21 or a pharmaceutically acceptable salt, solvate, hydrate, co-crystal, clathrate, polymorph or tautomer thereof, a pharmaceutically acceptable salt of the polymorph or tautomer, a stereoisomer of any of the foregoing, or a mixture thereof, wherein $R^9$ is —$OCHF_2$.

37. The compound of any one of embodiments 1-21 or a pharmaceutically acceptable salt, solvate, hydrate, co-crystal, clathrate, polymorph or tautomer thereof, a pharmaceutically acceptable salt of the polymorph or tautomer, a stereoisomer of any of the foregoing, or a mixture thereof, wherein $R^9$ is 38. The compound of any one of embodiments 1-21 or a pharmaceutically acceptable salt, solvate, hydrate, co-crystal, clathrate, polymorph or tautomer thereof, a pharmaceutically acceptable salt of the polymorph or tautomer, a stereoisomer of any of the foregoing, or a mixture thereof, wherein $R^9$ is 39. The compound of any one of embodiments 1-38 having the Formula I or a pharmaceutically acceptable salt, solvate, hydrate, co-crystal, clathrate, polymorph or tautomer thereof, a pharmaceutically acceptable salt of the polymorph or tautomer, a stereoisomer of any of the foregoing, or a mixture thereof, wherein B is substituted with one or more $R^{10}$ substituents.

40. The compound any one of embodiments 1-39 or a pharmaceutically acceptable salt, solvate, hydrate, co-crystal, clathrate, polymorph or tautomer thereof, a pharmaceutically acceptable salt of the polymorph or tautomer, a stereoisomer of any of the foregoing, or a mixture thereof, wherein $R^{10}$ is selected from hydrogen, halogen, —CN, —$OR^{11}$, —($C_1$-$C_6$ alkyl), —$NH_2$, —$CH_2NH_2$, —$CH_2OH$, —OH, 3 to 12 membered cycloalkyl or a 4 to 12 membered heterocyclic.

41. The compound any one of embodiments 1-40 or a pharmaceutically acceptable salt, solvate, hydrate, co-crystal, clathrate, polymorph or tautomer thereof, a pharmaceutically acceptable salt of the polymorph or tautomer, a stereoisomer of any of the foregoing, or a mixture thereof, wherein $R^{10}$ is hydrogen.
42. The compound any one of embodiments 1-40 or a pharmaceutically acceptable salt, solvate, hydrate, co-crystal, clathrate, polymorph or tautomer thereof, a pharmaceutically acceptable salt of the polymorph or tautomer, a stereoisomer of any of the foregoing, or a mixture thereof, wherein $R^{10}$ is halogen.
43. The compound any one of embodiments 1-40 or a pharmaceutically acceptable salt, solvate, hydrate, co-crystal, clathrate, polymorph or tautomer thereof, a pharmaceutically acceptable salt of the polymorph or tautomer, a stereoisomer of any of the foregoing, or a mixture thereof, wherein $R^{10}$ is —CN.
44. The compound any one of embodiments 1-40 or a pharmaceutically acceptable salt, solvate, hydrate, co-crystal, clathrate, polymorph or tautomer thereof, a pharmaceutically acceptable salt of the polymorph or tautomer, a stereoisomer of any of the foregoing, or a mixture thereof, wherein $R^{11}$ is —$OR^{11}$.
45. The compound any one of embodiments 1-40 or a pharmaceutically acceptable salt, solvate, hydrate, co-crystal, clathrate, polymorph or tautomer thereof, a pharmaceutically acceptable salt of the polymorph or tautomer, a stereoisomer of any of the foregoing, or a mixture thereof, wherein $R^{10}$ is —($C_1$-$C_6$ alkyl).
46. The compound any one of embodiments 1-40 or a pharmaceutically acceptable salt, solvate, hydrate, co-crystal, clathrate, polymorph or tautomer thereof, a pharmaceutically acceptable salt of the polymorph or tautomer, a stereoisomer of any of the foregoing, or a mixture thereof, wherein $R^{10}$ is —$NH_2$.
47. The compound any one of embodiments 1-40 or a pharmaceutically acceptable salt, solvate, hydrate, co-crystal, clathrate, polymorph or tautomer thereof, a pharmaceutically acceptable salt of the polymorph or tautomer, a stereoisomer of any of the foregoing, or a mixture thereof, wherein $R^{10}$ is —$CH_2NH_2$.
48. The compound any one of embodiments 1-40 or a pharmaceutically acceptable salt, solvate, hydrate, co-crystal, clathrate, polymorph or tautomer thereof, a pharmaceutically acceptable salt of the polymorph or tautomer, a stereoisomer of any of the foregoing, or a mixture thereof, wherein $R^{10}$ is —$CH_2OH$.
49. The compound any one of embodiments 1-40 or a pharmaceutically acceptable salt, solvate, hydrate, co-crystal, clathrate, polymorph or tautomer thereof, a pharmaceutically acceptable salt of the polymorph or tautomer, a stereoisomer of any of the foregoing, or a mixture thereof, wherein $R^{10}$ is —OH.
50. The compound any one of embodiments 1-40 or a pharmaceutically acceptable salt, solvate, hydrate, co-crystal, clathrate, polymorph or tautomer thereof, a pharmaceutically acceptable salt of the polymorph or tautomer, a stereoisomer of any of the foregoing, or a mixture thereof, wherein $R^{10}$ is 3 to 12 membered cycloalkyl.
51. The compound any one of embodiments 1-40 or a pharmaceutically acceptable salt, solvate, hydrate, co-crystal, clathrate, polymorph or tautomer thereof, a pharmaceutically acceptable salt of the polymorph or tautomer, a stereoisomer of any of the foregoing, or a mixture thereof, wherein $R^{10}$ is a 4 to 12 membered heterocyclic.
52. The compound any one of embodiments 1-51 or a pharmaceutically acceptable salt, solvate, hydrate, co-crystal, clathrate, polymorph or tautomer thereof, a pharmaceutically acceptable salt of the polymorph or tautomer, a stereoisomer of any of the foregoing, or a mixture thereof, wherein B is selected from

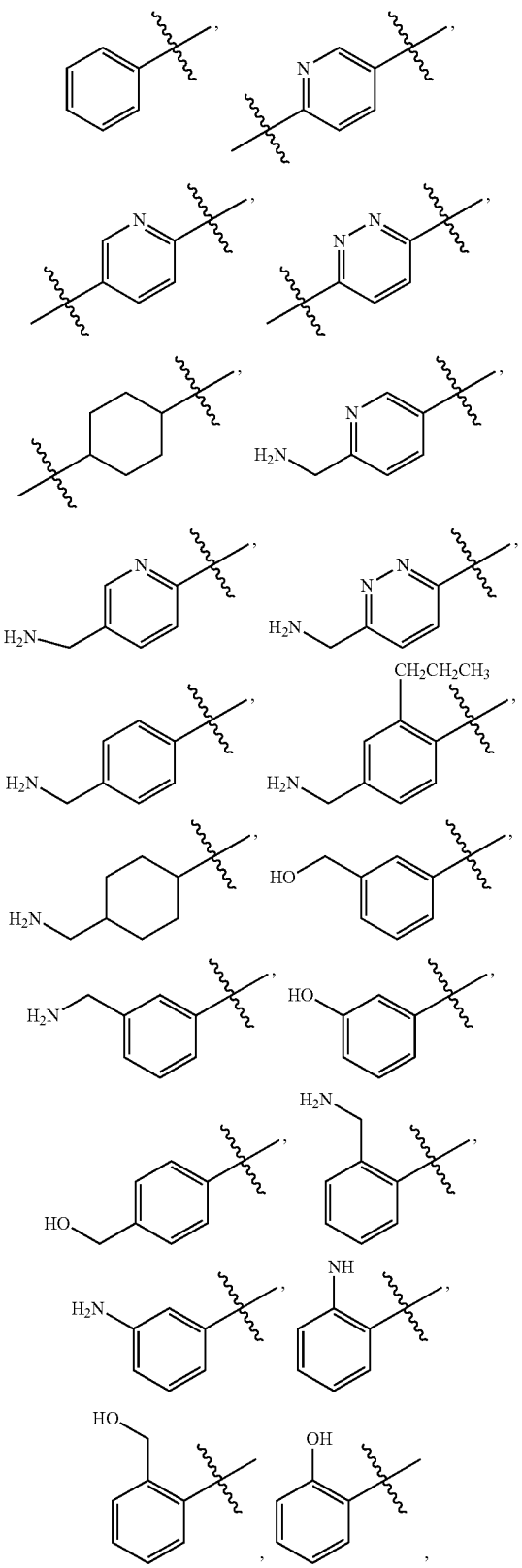

-continued

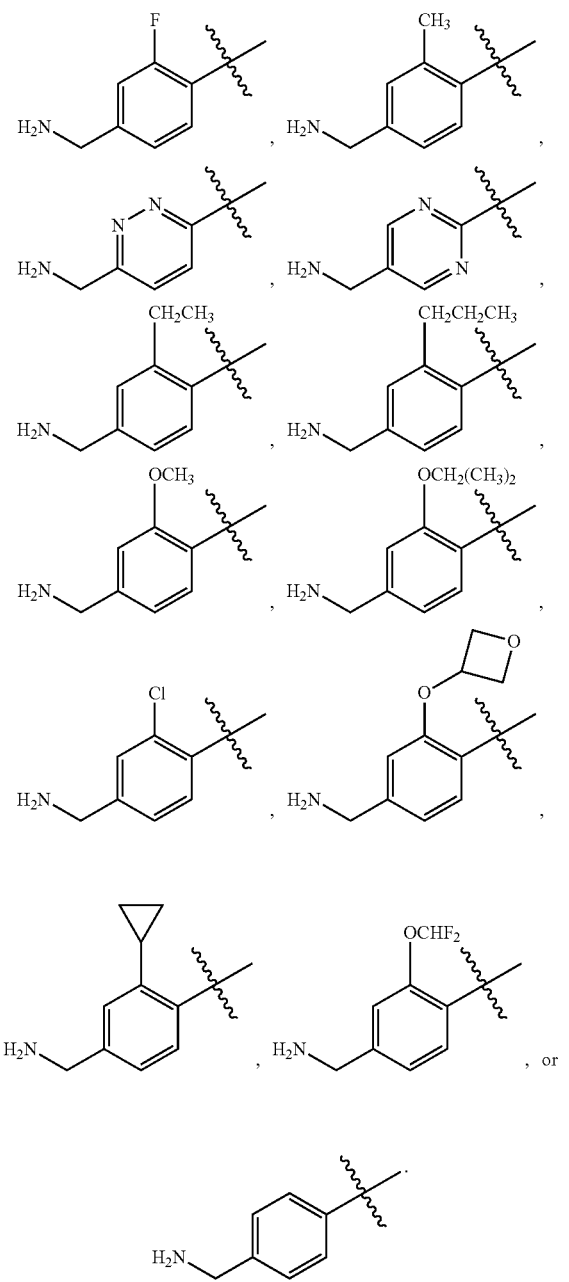

53. The compound any one of embodiments 1-52 or a pharmaceutically acceptable salt, solvate, hydrate, co-crystal, clathrate, polymorph or tautomer thereof, a pharmaceutically acceptable salt of the polymorph or tautomer, a stereoisomer of any of the foregoing, or a mixture thereof, wherein B is

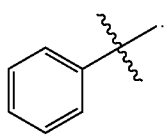 [SMILES: *c1ccccc1]

54. The compound of any of embodiments 1-52 or a pharmaceutically acceptable salt, solvate, hydrate, co-crystal, clathrate, polymorph or tautomer thereof, a pharmaceutically acceptable salt of the polymorph or tautomer, a stereoisomer of any of the foregoing, or a mixture thereof, wherein B is

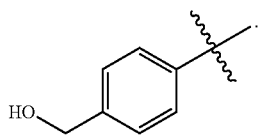

55. The compound of any of embodiments 1-52 or a pharmaceutically acceptable salt, solvate, hydrate, co-crystal, clathrate, polymorph or tautomer thereof, a pharmaceutically acceptable salt of the polymorph or tautomer, a stereoisomer of any of the foregoing, or a mixture thereof, wherein B is

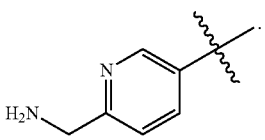

56. The compound of any of embodiments 1-52 or a pharmaceutically acceptable salt, solvate, hydrate, co-crystal, clathrate, polymorph or tautomer thereof, a pharmaceutically acceptable salt of the polymorph or tautomer, a stereoisomer of any of the foregoing, or a mixture thereof, wherein B is

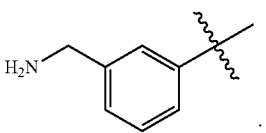 [SMILES: *c1cccc(CN)c1]

57. The compound of any of embodiments 1-52 or a pharmaceutically acceptable salt, solvate, hydrate, co-crystal, clathrate, polymorph or tautomer thereof, a pharmaceutically acceptable salt of the polymorph or tautomer, a stereoisomer of any of the foregoing, or a mixture thereof, wherein B is

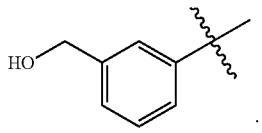 [SMILES: *c1cccc(CO)c1]

58. The compound of any of embodiments 1-52 or a pharmaceutically acceptable salt, solvate, hydrate, co-crystal, clathrate, polymorph or tautomer thereof, a pharmaceutically acceptable salt of the polymorph or tautomer, a stereoisomer of any of the foregoing, or a mixture thereof, wherein B is

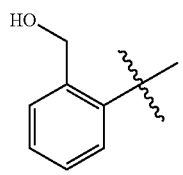

59. The compound of any of embodiments 1-52 or a pharmaceutically acceptable salt, solvate, hydrate, co-crystal, clathrate, polymorph or tautomer thereof, a pharmaceutically acceptable salt of the polymorph or tautomer, a stereoisomer of any of the foregoing, or a mixture thereof, wherein B is

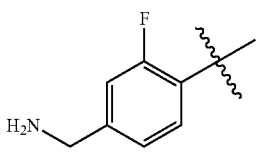

60. The compound of any of embodiments 1-52 or a pharmaceutically acceptable salt, solvate, hydrate, co-crystal, clathrate, polymorph or tautomer thereof, a pharmaceutically acceptable salt of the polymorph or tautomer, a stereoisomer of any of the foregoing, or a mixture thereof, wherein B is

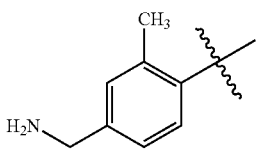

61. The compound of any of embodiments 1-52 or a pharmaceutically acceptable salt, solvate, hydrate, co-crystal, clathrate, polymorph or tautomer thereof, a pharmaceutically acceptable salt of the polymorph or tautomer, a stereoisomer of any of the foregoing, or a mixture thereof, wherein B is

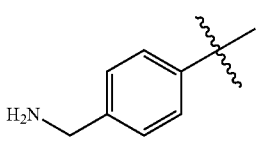

62. The compound of any of embodiments 1-61 or a pharmaceutically acceptable salt, solvate, hydrate, co-crystal, clathrate, polymorph or tautomer thereof, a pharmaceutically acceptable salt of the polymorph or tautomer, a stereoisomer of any of the foregoing, or a mixture thereof, wherein $R^1$ is selected from hydrogen or $—C_1-C_6$ alkyl.
63. The compound of any of embodiments 1-62 or a pharmaceutically acceptable salt, solvate, hydrate, co-crystal, clathrate, polymorph or tautomer thereof, a pharmaceutically acceptable salt of the polymorph or tautomer, a stereoisomer of any of the foregoing, or a mixture thereof, wherein $R^1$ is hydrogen.
64. The compound of any of embodiments 1-61 or a pharmaceutically acceptable salt, solvate, hydrate, co-crystal, clathrate, polymorph or tautomer thereof, a pharmaceutically acceptable salt of the polymorph or tautomer, a stereoisomer of any of the foregoing, or a mixture thereof, wherein $R^1$ is $—C_1-C_6$ alkyl.
65. The compound any of embodiments 1-62, or 64, or a pharmaceutically acceptable salt, solvate, hydrate, co-crystal, clathrate, polymorph or tautomer thereof, a pharmaceutically acceptable salt of the polymorph or tautomer, a stereoisomer of any of the foregoing, or a mixture thereof, wherein $R^1$ is methyl.
66. The compound of any of embodiments 1-65 or a pharmaceutically acceptable salt, solvate, hydrate, co-crystal, clathrate, polymorph or tautomer thereof, a pharmaceutically acceptable salt of the polymorph or tautomer, a stereoisomer of any of the foregoing, or a mixture thereof, wherein $R^2$, $R^3$ and $R^4$ are hydrogen.
67. The compound of any of embodiments 1-66 or a pharmaceutically acceptable salt, solvate, hydrate, co-crystal, clathrate, polymorph or tautomer thereof, a pharmaceutically acceptable salt of the polymorph or tautomer, a stereoisomer of any of the foregoing, or a mixture thereof, wherein $R^6$ is selected from hydrogen or $—C_1-C_6$ alkyl.
68. The compound of any of embodiments 1-66 or a pharmaceutically acceptable salt, solvate, hydrate, co-crystal, clathrate, polymorph or tautomer thereof, a pharmaceutically acceptable salt of the polymorph or tautomer, a stereoisomer of any of the foregoing, or a mixture thereof, wherein $R^6$ is hydrogen.
69. The compound of any of embodiments 1-67 or a pharmaceutically acceptable salt, solvate, hydrate, co-crystal, clathrate, polymorph or tautomer thereof, a pharmaceutically acceptable salt of the polymorph or tautomer, a stereoisomer of any of the foregoing, or a mixture thereof, wherein $R^6$ is $—C_1-C_6$ alkyl.
70. The compound any of embodiments 1-67, or 69, or a pharmaceutically acceptable salt, solvate, hydrate, co-crystal, clathrate, polymorph or tautomer thereof, a pharmaceutically acceptable salt of the polymorph or tautomer, a stereoisomer of any of the foregoing, or a mixture thereof, wherein $R^6$ is methyl.
71. The compound any of embodiments 1-70, or a pharmaceutically acceptable salt, solvate, hydrate, co-crystal, clathrate, polymorph or tautomer thereof, a pharmaceutically acceptable salt of the polymorph or tautomer, a stereoisomer of any of the foregoing, or a mixture thereof, wherein $R^8$ is methyl.
72. The compound any of embodiments 1-70, or a pharmaceutically acceptable salt, solvate, hydrate, co-crystal, clathrate, polymorph or tautomer thereof, a pharmaceutically acceptable salt of the polymorph or tautomer, a stereoisomer of any of the foregoing, or a mixture thereof, wherein $R^8$ is hydrogen.
73. In another embodiment, the present invention comprises a compound having a Formula II:

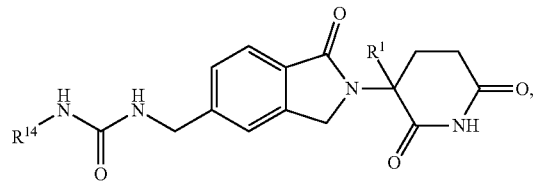

or a pharmaceutically acceptable salt, solvate, hydrate, co-crystal, clathrate, polymorph or tautomer thereof, a pharmaceutically acceptable salt of the polymorph or tautomer, a stereoisomer of any of the foregoing, or a mixture thereof, wherein:
$R^1$ is independently selected from hydrogen or methyl;
$R^{14}$ is independently selected from
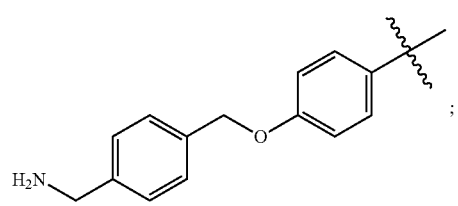;
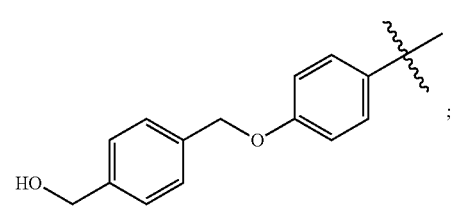;
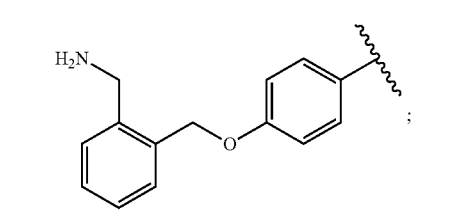;
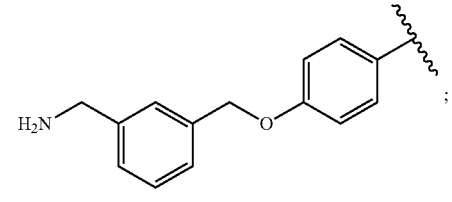;
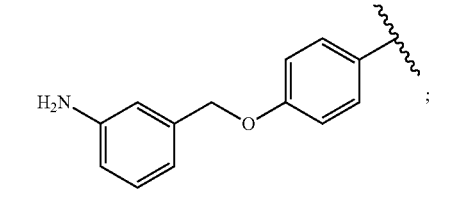;
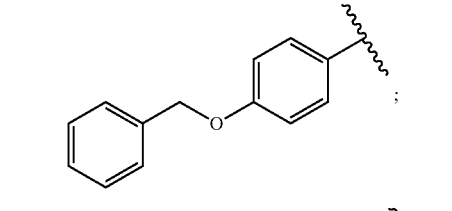;
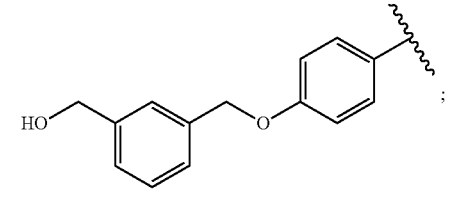;
-continued
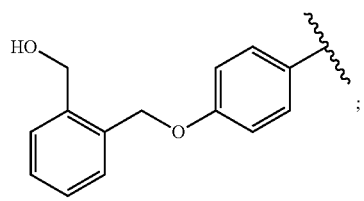;
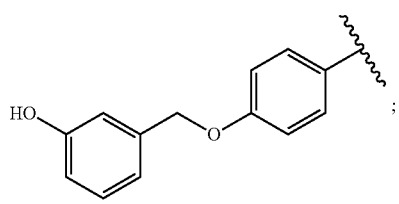;
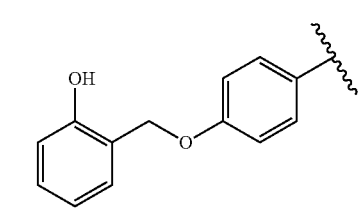;
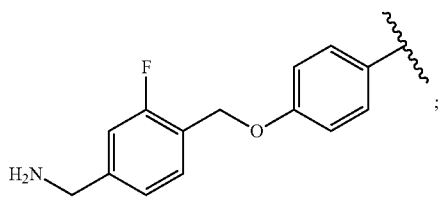;
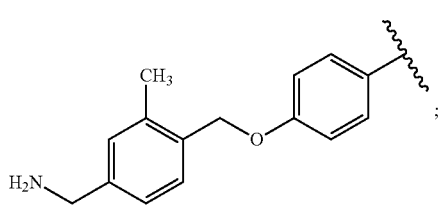;
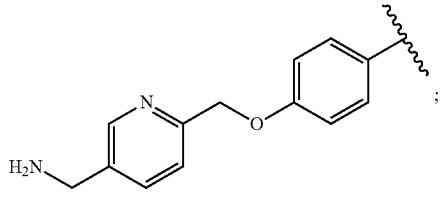;
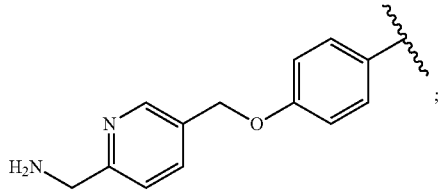;
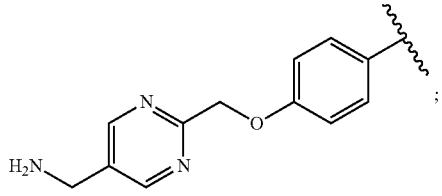;

-continued
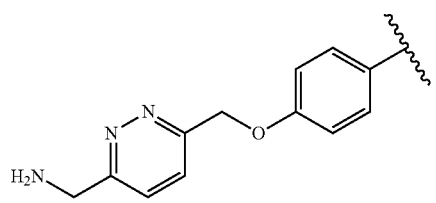
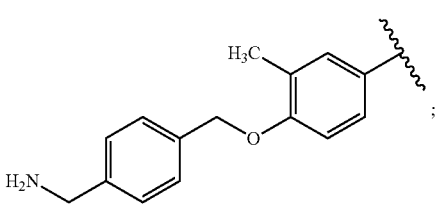
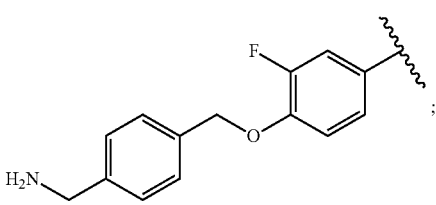
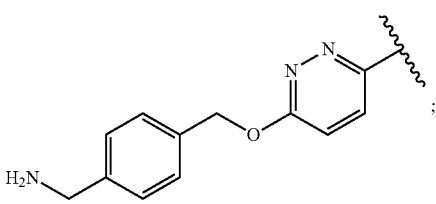
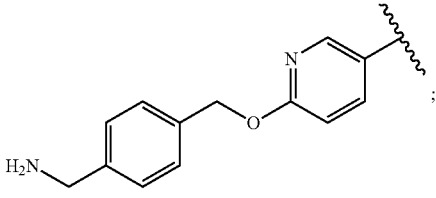
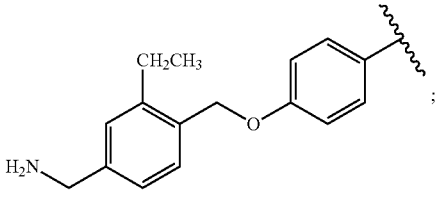
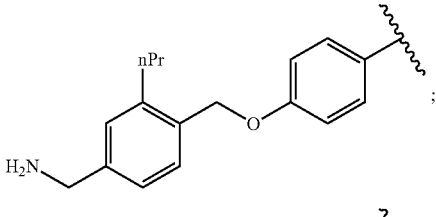
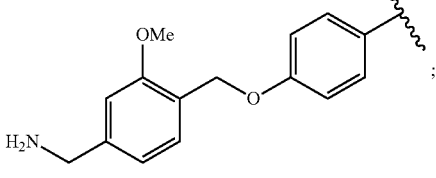
-continued
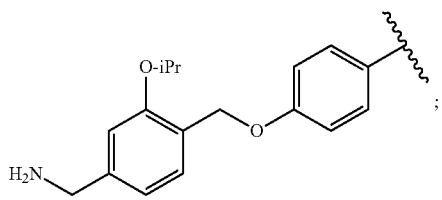
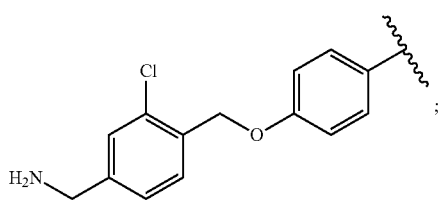
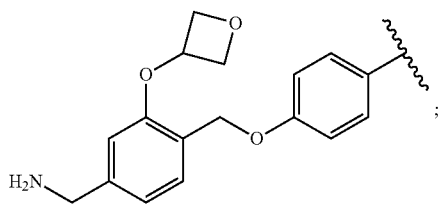
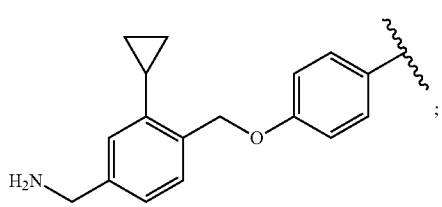
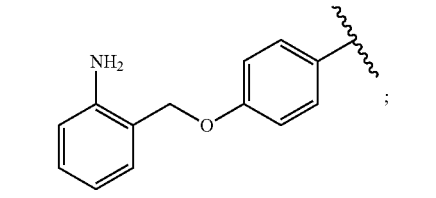
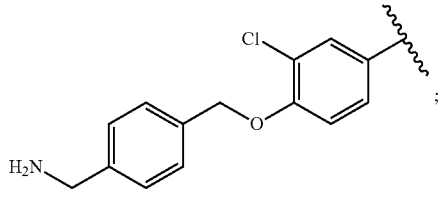
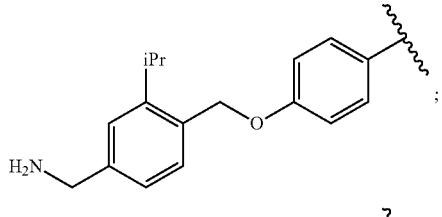
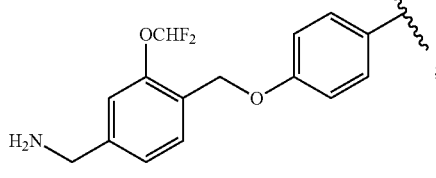

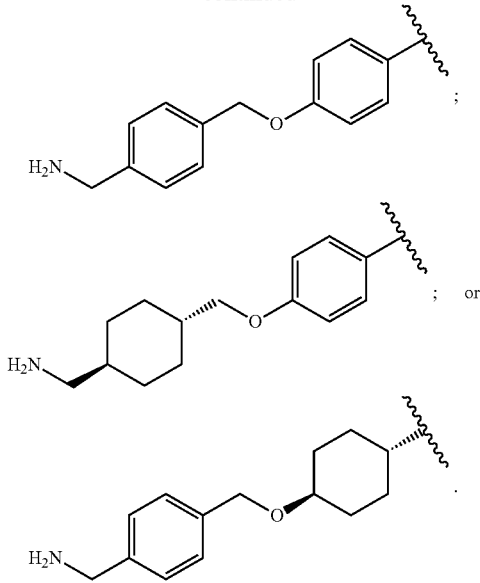

74. The compound of Embodiment 1, wherein the compound is selected from 1-((2-(2,6-dioxopiperidin-3-yl)-1-oxoisoindolin-5-yl)methyl)-3-(4-((4-(hydroxymethyl)benzyl)oxy)phenyl)urea, 1-[4-[[4-(aminomethyl)phenyl]methoxy]phenyl]-3-[[2-(2,6-dioxo-3-piperidyl)-1-oxo-isoindolin-5-yl]methyl]urea, 1-(4-((2-(aminomethyl)benzyl)oxy)phenyl)-3-((2-(2,6-dioxopiperidin-3-yl)-1-oxoisoindolin-5-yl)methyl)urea, 1-(4-((3-(aminomethyl)benzyl)oxy)phenyl)-3-((2-(2,6-dioxopiperidin-3-yl)-1-oxoisoindolin-5-yl)methyl)urea, 1-(4-((3-aminobenzyl)oxy)phenyl)-3-((2-(2,6-dioxopiperidin-3-yl)-1-oxoisoindolin-5-yl)methyl)urea, 1-[4-(benzyloxy)phenyl]-3-{[2-(2,6-dioxopiperidin-3-yl)-1-oxo-2,3-dihydro-1H-isoindol-5-yl]methyl}urea, 1-((2-(2,6-dioxopiperidin-3-yl)-1-oxoisoindolin-5-yl)methyl)-3-(4-((3-(hydroxymethyl)benzyl)oxy)phenyl)urea, 1-((2-(2,6-dioxopiperidin-3-yl)-1-oxoisoindolin-5-yl)methyl)-3-(4-((2-(hydroxymethyl)benzyl)oxy)phenyl)urea, 1-((2-(2,6-dioxopiperidin-3-yl)-1-oxoisoindolin-5-yl)methyl)-3-(4-((2-hydroxybenzyl)oxy)phenyl)urea, 1-((2-(2,6-dioxopiperidin-3-yl)-1-oxoisoindolin-5-yl)methyl)-3-(4-((2-hydroxybenzyl)oxy)phenyl)urea, 1-(4-{[4-(aminomethyl)-2-fluorophenyl]methoxy}phenyl)-3-{[2-(2,6-dioxopiperidin-3-yl)-1-oxo-2,3-dihydro-1H-isoindol-5-yl]methyl}urea, 1-(4-{[4-(aminomethyl)-2-methylphenyl]methoxy}phenyl)-3-{[2-(2,6-dioxopiperidin-3-yl)-1-oxo-2,3-dihydro-1H-isoindol-5-yl]methyl}urea, 1-(4-{[5-(aminomethyl)pyridin-2-yl]methoxy}phenyl)-3-{[2-(2,6-dioxopiperidin-3-yl)-1-oxo-2,3-dihydro-1H-isoindol-5-yl]methyl}urea, 1-(4-{[6-(aminomethyl)pyridin-3-yl]methoxy}phenyl)-3-{[2-(2,6-dioxopiperidin-3-yl)-1-oxo-2,3-dihydro-1H-isoindol-5-yl]methyl}urea, 1-(4-{[5-(aminomethyl)pyrimidin-2-yl]methoxy}phenyl)-3-{[2-(2,6-dioxopiperidin-3-yl)-1-oxo-2,3-dihydro-1H-isoindol-5-yl]methyl}urea, 1-(4-{[6-(aminomethyl)pyridazin-3-yl]methoxy}phenyl)-3-{[2-(2,6-dioxopiperidin-3-yl)-1-oxo-2,3-dihydro-1H-isoindol-5-yl]methyl}urea, 1-(4-{[4-(aminomethyl)phenyl]methoxy}-3-methylphenyl)-3-{[2-(2,6-dioxopiperidin-3-yl)-1-oxo-2,3-dihydro-1H-isoindol-5-yl]methyl}urea, 1-(4-{[4-(aminomethyl)phenyl]methoxy}-3-fluorophenyl)-3-{[2-(2,6-dioxopiperidin-3-yl)-1-oxo-2,3-dihydro-1H-isoindol-5-yl]methyl}urea, 1-(6-{[4-(aminomethyl)phenyl]methoxy}pyridazin-3-yl)-3-{[2-(2,6-dioxopiperidin-3-yl)-1-oxo-2,3-dihydro-1H-isoindol-5-yl]methyl}urea, 1-(6-{[4-(aminomethyl)phenyl]methoxy}pyridin-3-yl)-3-{[2-(2,6-dioxopiperidin-3-yl)-1-oxo-2,3-dihydro-1H-isoindol-5-yl]methyl}urea, 1-(4-{[4-(aminomethyl)-2-ethylphenyl]methoxy}phenyl)-3-{[2-(2,6-dioxopiperidin-3-yl)-1-oxo-2,3-dihydro-1H-isoindol-5-yl]methyl}urea, 1-(4-{[4-(aminomethyl)-2-n-propylphenyl]methoxy}phenyl)-3-{[2-(2,6-dioxopiperidin-3-yl)-1-oxo-2,3-dihydro-1H-isoindol-5-yl]methyl}urea, 1-(4-{[4-(aminomethyl)-2-methoxyphenyl]methoxy}phenyl)-3-{[2-(2,6-dioxopiperidin-3-yl)-1-oxo-2,3-dihydro-1H-isoindol-5-yl]methyl}urea, 1-(4-{[4-(aminomethyl)-2-(propan-2-yloxy)phenyl]methoxy}phenyl)-3-{[2-(2,6-dioxopiperidin-3-yl)-1-oxo-2,3-dihydro-1H-isoindol-5-yl]methyl}urea, 1-(4-{[4-(aminomethyl)-2-chlorophenyl]methoxy}phenyl)-3-{[2-(2,6-dioxopiperidin-3-yl)-1-oxo-2,3-dihydro-1H-isoindol-5-yl]methyl}urea, 1-(4-{[4-(aminomethyl)-2-(oxetan-3-yloxy)phenyl]methoxy}phenyl)-3-{[2-(2,6-dioxopiperidin-3-yl)-1-oxo-2,3-dihydro-1H-isoindol-5-yl]methyl}urea, 1-(4-{[4-(aminomethyl)-2-cyclopropylphenyl]methoxy}phenyl)-3-{[2-(2,6-dioxopiperidin-3-yl)-1-oxo-2,3-dihydro-1H-isoindol-5-yl]methyl}urea, 1-(4-((2-aminobenzyl)oxy)phenyl)-3-((2-(2,6-dioxopiperidin-3-yl)-1-oxoisoindolin-5-yl)methyl)urea, 1-(4-((4-(aminomethyl)benzyl)oxy)-3-chlorophenyl)-3-((2-(2,6-dioxopiperidin-3-yl)-1-oxoisoindolin-5-yl)methyl)urea, 1-(4-{[4-(aminomethyl)-2-i-propylphenyl]methoxy}phenyl)-3-{[2-(2,6-dioxopiperidin-3-yl)-1-oxo-2,3-dihydro-1H-isoindol-5-yl]methyl}urea, 1-(4-{[4-(aminomethyl)-2-diflouromethoxyphenyl]methoxy}phenyl)-3-{[2-(2,6-dioxopiperidin-3-yl)-1-oxo-2,3-dihydro-1H-isoindol-5-yl]methyl}urea, 1-(4-{[4-(aminomethyl)phenyl]methoxy}phenyl)-3-({2-[(3S)-3-methyl-2,6-dioxopiperidin-3-yl]-1-oxo-2,3-dihydro-1H-isoindol-5-yl}methyl)urea, 1-(4-{[4-(aminomethyl)phenyl]methoxy}phenyl)-3-({2-[(3R)-3-methyl-2,6-dioxopiperidin-3-yl]-1-oxo-2,3-dihydro-1H-isoindol-5-yl}methyl)urea, 3-{[2-(2,6-dioxopiperidin-3-yl)-1-oxo-2,3-dihydro-1H-isoindol-5-yl]methyl}-1-(4-{[(1r,4r)-4-(aminomethyl)cyclohexyl]methoxy}phenyl)urea, or 3-{[2-(2,6-dioxopiperidin-3-yl)-1-oxo-2,3-dihydro-1H-isoindol-5-yl]methyl}-1-[(1r,4r)-4-{[4-(aminomethyl)phenyl]methoxy}cyclohexyl]urea, or a pharmaceutically acceptable salt, solvate, hydrate, co-crystal, clathrate, polymorph or tautomer thereof, a pharmaceutically acceptable salt of the polymorph or tautomer, a stereoisomer of any of the foregoing, or a mixture thereof.

75. In another aspect, the present invention comprises a compound having the structure

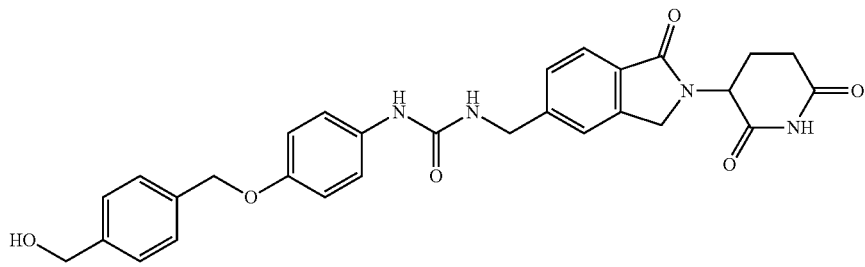 [SMILES: O=C1CCC(N2Cc3cc(CNC(=O)Nc4ccc(OCc5ccc(CO)cc5)cc4)ccc3C2=O)C(=O)N1]

or a pharmaceutically acceptable salt, solvate, hydrate, co-crystal, clathrate, polymorph or tautomer thereof, a pharmaceutically acceptable salt of the polymorph or tautomer, a stereoisomer of any of the foregoing, or a mixture thereof.

76. In another aspect, the present invention comprises a compound having the structure

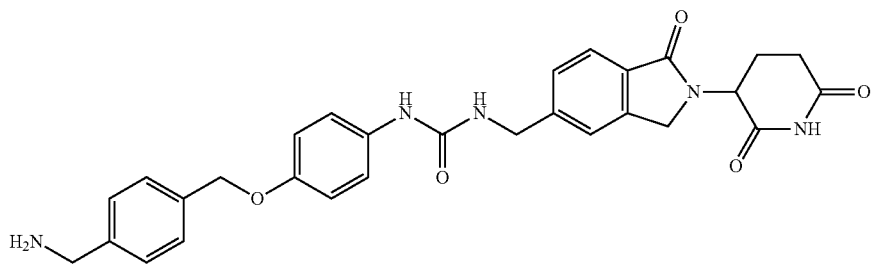

or a pharmaceutically acceptable salt, solvate, hydrate, co-crystal, clathrate, polymorph or tautomer thereof, a pharmaceutically acceptable salt of the polymorph or tautomer, a stereoisomer of any of the foregoing, or a mixture thereof.

77. In another aspect, the present invention comprises a compound having the structure

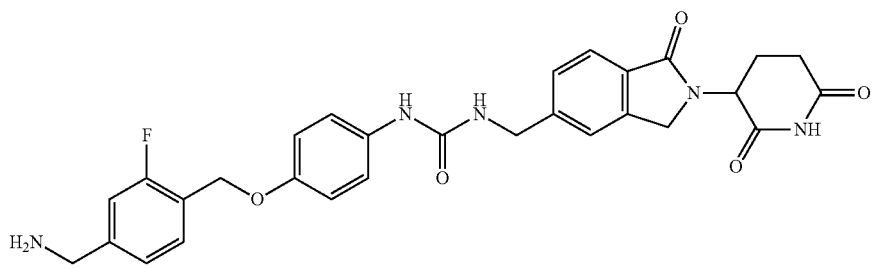 [SMILES: NCc1ccc(COc2ccc(NC(=O)NCc3ccc4c(c3)CN(C3CCC(=O)NC3=O)C4=O)cc2)c(F)c1]

or a pharmaceutically acceptable salt, solvate, hydrate, co-crystal, clathrate, polymorph or tautomer thereof, a pharmaceutically acceptable salt of the polymorph or tautomer, a stereoisomer of any of the foregoing, or a mixture thereof.

78. In another aspect, the present invention comprises a compound having the structure

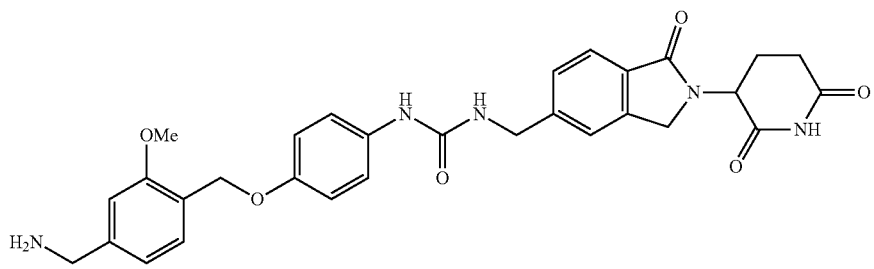

or a pharmaceutically acceptable salt, solvate, hydrate, co-crystal, clathrate, polymorph or tautomer thereof, a pharmaceutically acceptable salt of the polymorph or tautomer, a stereoisomer of any of the foregoing, or a mixture thereof.

79. In another aspect, the present invention comprises a compound having the structure

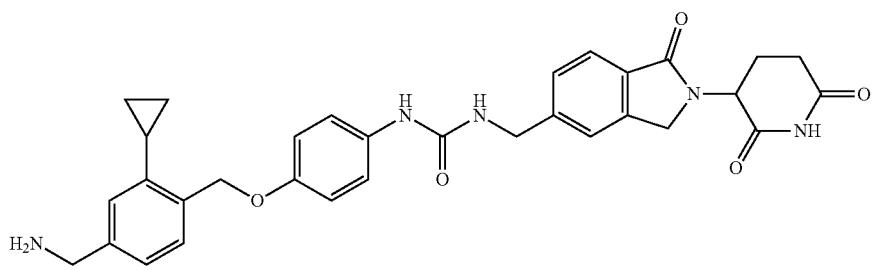 [SMILES: NCc1ccc(COc2ccc(NC(=O)NCc3ccc4c(c3)CN(C3CCC(=O)NC3=O)C4=O)cc2)c(C2CC2)c1]

or a pharmaceutically acceptable salt, solvate, hydrate, co-crystal, clathrate, polymorph or tautomer thereof, a pharmaceutically acceptable salt of the polymorph or tautomer, a stereoisomer of any of the foregoing, or a mixture thereof.

80. In another aspect, the present invention comprises a compound having the structure

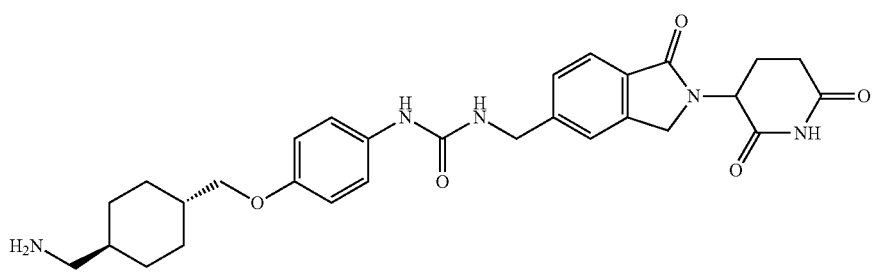 [SMILES: NC[C@H]1CC[C@H](COc2ccc(NC(=O)NCc3ccc4c(c3)CN(C3CCC(=O)NC3=O)C4=O)cc2)CC1]

or a pharmaceutically acceptable salt, solvate, hydrate, co-crystal, clathrate, polymorph or tautomer thereof, a pharmaceutically acceptable salt of the polymorph or tautomer, a stereoisomer of any of the foregoing, or a mixture thereof.

81. In another aspect, the present invention comprises a compound having the structure

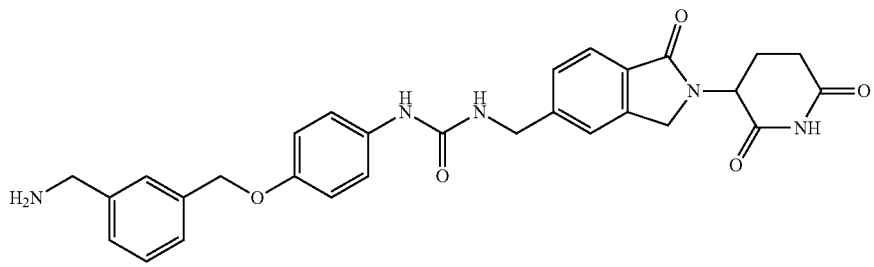 [SMILES: NCc1cccc(COc2ccc(NC(=O)NCc3ccc4c(c3)CN(C3CCC(=O)NC3=O)C4=O)cc2)c1]

or a pharmaceutically acceptable salt, solvate, hydrate, co-crystal, clathrate, polymorph or tautomer thereof, a pharmaceutically acceptable salt of the polymorph or tautomer, a stereoisomer of any of the foregoing, or a mixture thereof.

82. In another aspect, the present invention comprises a compound having the structure

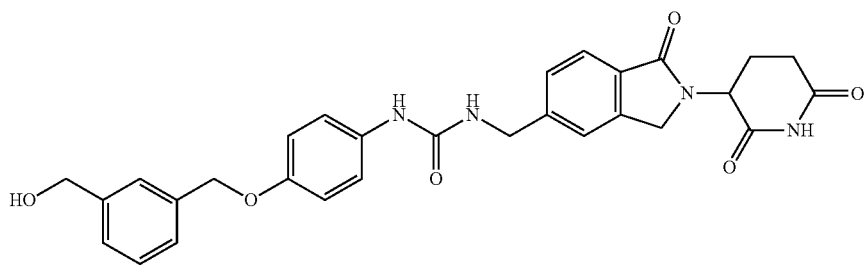 [SMILES: O=C1CCC(N2Cc3cc(CNC(=O)Nc4ccc(OCc5cccc(CO)c5)cc4)ccc3C2=O)C(=O)N1]

or a pharmaceutically acceptable salt, solvate, hydrate, co-crystal, clathrate, polymorph or tautomer thereof, a pharmaceutically acceptable salt of the polymorph or tautomer, a stereoisomer of any of the foregoing, or a mixture thereof.

83. In another aspect, the present invention comprises a compound having the structure

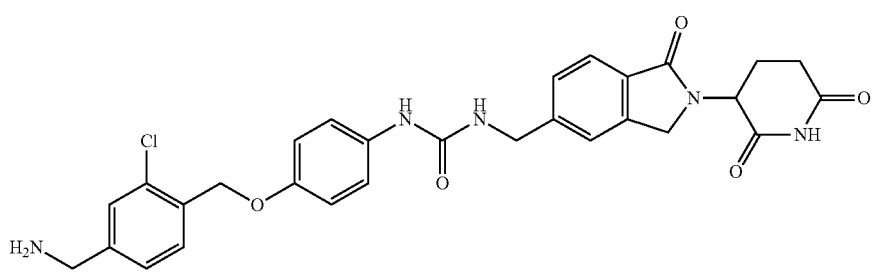

or a pharmaceutically acceptable salt, solvate, hydrate, co-crystal, clathrate, polymorph or tautomer thereof, a pharmaceutically acceptable salt of the polymorph or tautomer, a stereoisomer of any of the foregoing, or a mixture thereof.

84. In another aspect, the present invention comprises a compound having the structure

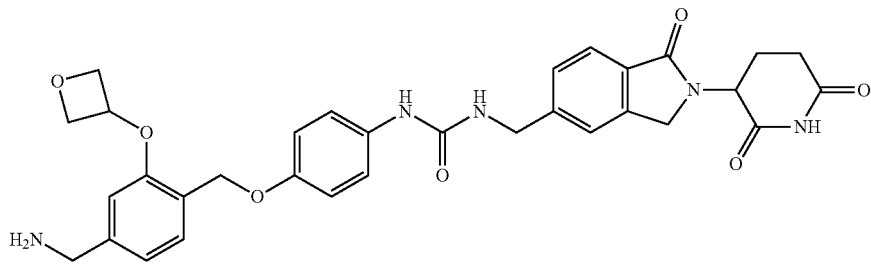 [SMILES: NCc1ccc(COc2ccc(NC(=O)NCc3ccc4c(c3)CN(C3CCC(=O)NC3=O)C4=O)cc2)c(OC2COC2)c1]

or a pharmaceutically acceptable salt, solvate, hydrate, co-crystal, clathrate, polymorph or tautomer thereof, a pharmaceutically acceptable salt of the polymorph or tautomer, a stereoisomer of any of the foregoing, or a mixture thereof.

85. In another aspect, the present invention comprises a compound of any one of embodiments 1-84 for use as a medicament.
86. A compound of any one of embodiments 1-85 for use in a method of treating cancer, comprising administering to a mammal having cancer a therapeutically effective amount of the compound.
87. The compound for use according to embodiment 86, wherein the cancer is leukemia.
88. The compound for use according to embodiment 87, wherein the leukemia is chronic lymphocytic leukemia, chronic myelocytic leukemia, acute lymphoblastic leukemia or acute myeloid leukemia.
89. The compound for use according to embodiment 88, wherein the leukemia is an acute myeloid leukemia.
90. The compound for use of any one of embodiments 1-89, wherein the leukemia is relapsed, refractory or resistant to conventional therapy.
91. The compound for use according to any one of embodiments 86-89, wherein the method further comprises administering a therapeutically effective amount of another second active agent or a support care therapy.
92. The compound for use according to embodiment 91, wherein the other second active agent is a therapeutic antibody that specifically binds to a cancer antigen, hematopoietic growth factor, cytokine, anti-cancer agent, antibiotic, cox-2 inhibitor, immunomodulatory agent, immunosuppressive agent, corticosteroid or a pharmacologically active mutant or derivative thereof.

In one embodiment, the compound provided herein is a compound of Table 1.

In another embodiment, compounds in which X=NR[11] comprise the following compounds

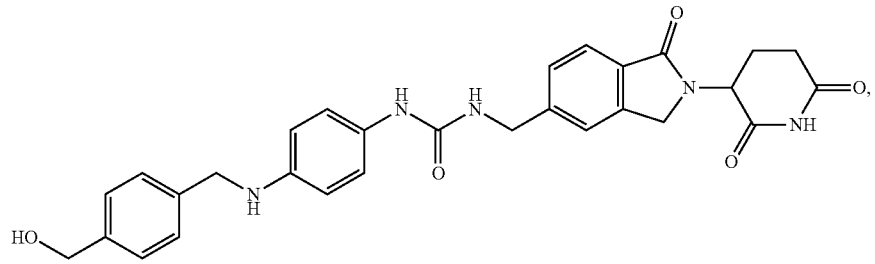

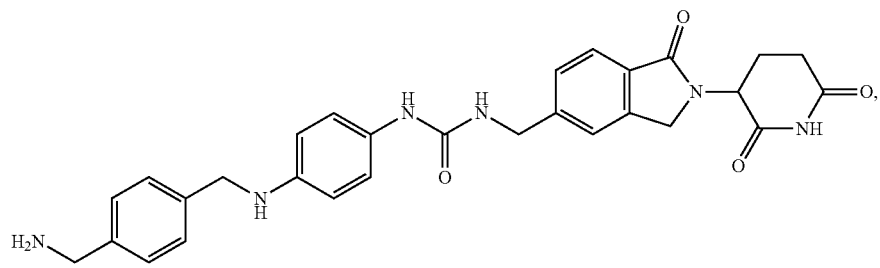

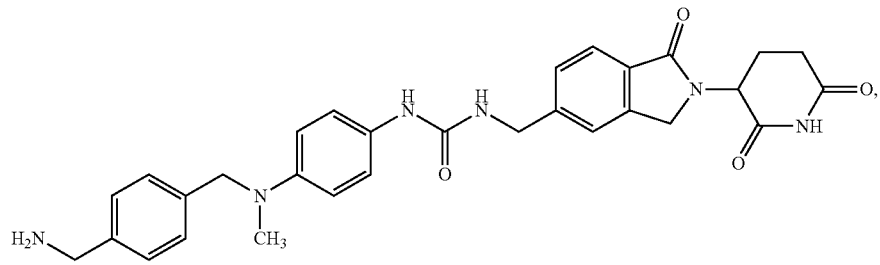

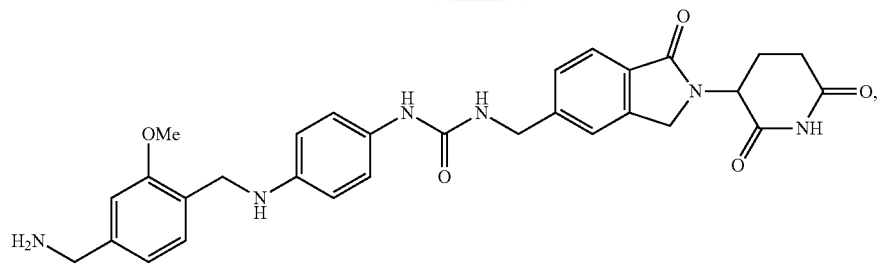
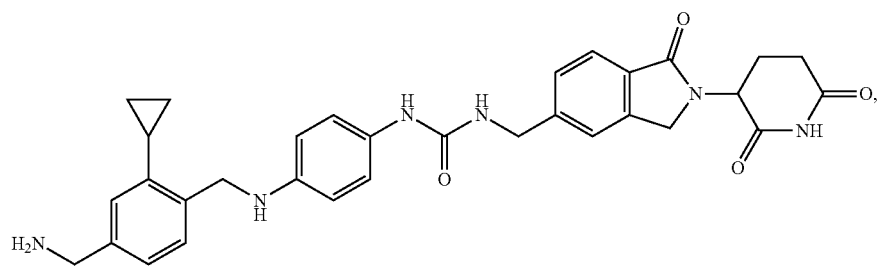
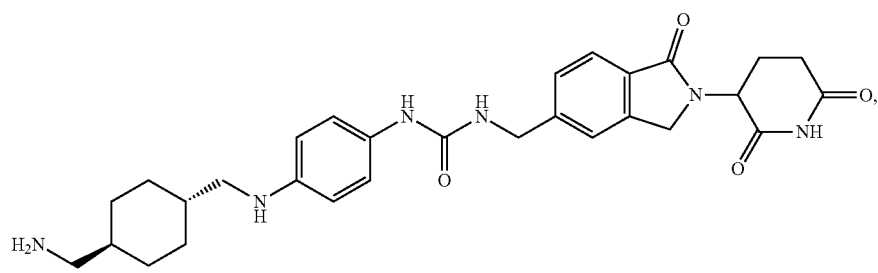
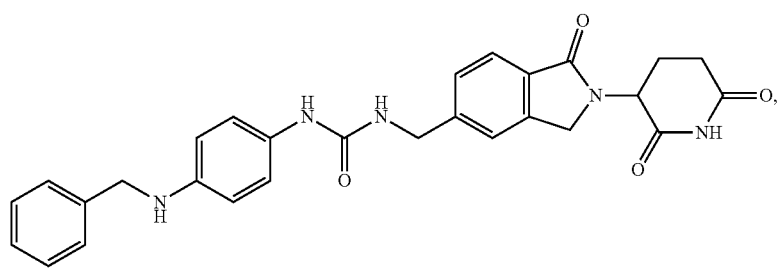
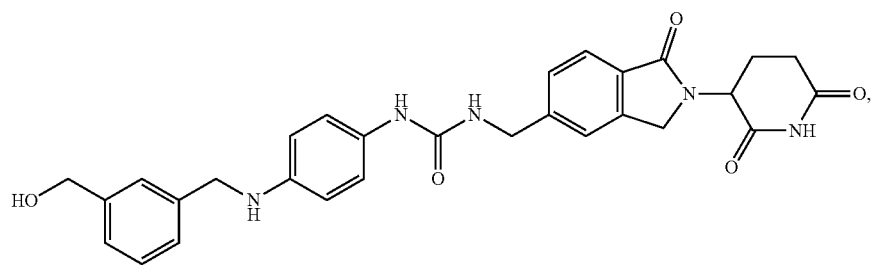
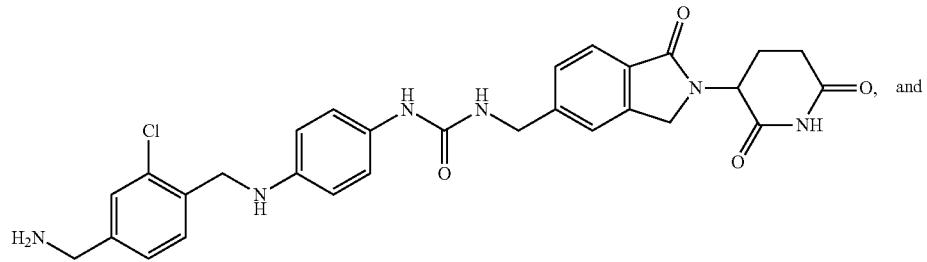

-continued

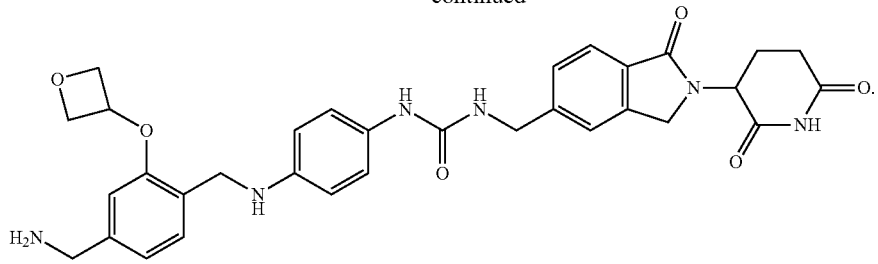

The compounds wherein X=NH may be synthesized using similar routes as described herein to one of ordinary skill in the art.

Also provided herein are isotopically enriched analogs of the compounds provided herein. Isotopic enrichment (for example, deuteration) of pharmaceuticals to improve pharmacokinetics ("PK"), pharmacodynamics ("PD"), and toxicity profiles, has been demonstrated previously with some classes of drugs. See, for example, Lijinsky et. al., *Food Cosmet. Toxicol.*, 20: 393 (1982); Lijinsky et. al., *J. Nat. Cancer Inst.*, 69: 1127 (1982); Mangold et. al., *Mutation Res.* 308: 33 (1994); Gordon et. al., *Drug Metab. Dispos.*, 15: 589 (1987); Zello et. al., *Metabolism*, 43: 487 (1994); Gately et. al., *J. Nucl. Med.*, 27: 388 (1986); Wade D, *Chem. Biol. Interact.* 117: 191 (1999).

Without being limited by any particular theory, isotopic enrichment of a drug can be used, for example, to (1) reduce or eliminate unwanted metabolites, (2) increase the half-life of the parent drug, (3) decrease the number of doses needed to achieve a desired effect, (4) decrease the amount of a dose necessary to achieve a desired effect, (5) increase the formation of active metabolites, if any are formed, and/or (6) decrease the production of deleterious metabolites in specific tissues and/or create a more effective drug and/or a safer drug for combination therapy, whether the combination therapy is intentional or not.

Replacement of an atom for one of its isotopes often will result in a change in the reaction rate of a chemical reaction. This phenomenon is known as the Kinetic Isotope Effect ("KIE"). For example, if a C—H bond is broken during a rate-determining step in a chemical reaction (i.e. the step with the highest transition state energy), substitution of a deuterium for that hydrogen will cause a decrease in the reaction rate and the process will slow down. This phenomenon is known as the Deuterium Kinetic Isotope Effect ("DKIE"). (See, e.g., Foster et al., Adv. Drug Res., vol. 14, pp. 1-36 (1985); Kushner et al., Can. J. Physiol. Pharmacol., vol. 77, pp. 79-88 (1999)).

The magnitude of the DKIE can be expressed as the ratio between the rates of a given reaction in which a C—H bond is broken, and the same reaction where deuterium is substituted for hydrogen. The DKIE can range from about 1 (no isotope effect) to very large numbers, such as 50 or more, meaning that the reaction can be fifty, or more, times slower when deuterium is substituted for hydrogen. Without being limited by a particular theory, high DKIE values may be due in part to a phenomenon known as tunneling, which is a consequence of the uncertainty principle. Tunneling is ascribed to the small mass of a hydrogen atom, and occurs because transition states involving a proton can sometimes form in the absence of the required activation energy. Because deuterium has more mass than hydrogen, it statistically has a much lower probability of undergoing this phenomenon.

Tritium ("T") is a radioactive isotope of hydrogen, used in research, fusion reactors, neutron generators and radiopharmaceuticals. Tritium is a hydrogen atom that has 2 neutrons in the nucleus and has an atomic weight close to 3. It occurs naturally in the environment in very low concentrations, most commonly found as $T_2O$. Tritium decays slowly (half-life=12.3 years) and emits a low energy beta particle that cannot penetrate the outer layer of human skin. Internal exposure is the main hazard associated with this isotope, yet it must be ingested in large amounts to pose a significant health risk. As compared with deuterium, a lesser amount of tritium must be consumed before it reaches a hazardous level. Substitution of tritium ("T") for hydrogen results in yet a stronger bond than deuterium and gives numerically larger isotope effects.

Similarly, substitution of isotopes for other elements, including, but not limited to, $^{13}C$ or $^{14}C$ for carbon, $^{33}S$, $^{34}S$, or $^{36}S$ for sulfur, $^{15}N$ for nitrogen, and $^{17}O$ or $^{18}O$ for oxygen, will provide a similar kinetic isotope effects.

The animal body expresses a variety of enzymes for the purpose of eliminating foreign substances, such as therapeutic agents, from its circulation system. Examples of such enzymes include the cytochrome P450 enzymes ("CYPs"), esterases, proteases, reductases, dehydrogenases, and monoamine oxidases, to react with and convert these foreign substances to more polar intermediates or metabolites for renal excretion. Some of the most common metabolic reactions of pharmaceutical compounds involve the oxidation of a carbon-hydrogen (C—H) bond to either a carbon-oxygen (C—O) or carbon-carbon (C—C) pi-bond. The resultant metabolites may be stable or unstable under physiological conditions, and can have substantially different pharmacokinetic, pharmacodynamic, and acute and long-term toxicity profiles relative to the parent compounds. For many drugs, such oxidations are rapid. As a result, these drugs often require the administration of multiple or high daily doses.

Isotopic enrichment at certain positions of a compound provided herein may produce a detectable KIE that affects the pharmacokinetic, pharmacologic, and/or toxicological profiles of a compound provided herein in comparison with a similar compound having a natural isotopic composition. In one embodiment, the deuterium enrichment is performed on the site of CH bond cleavage during metabolism.

C. Methods of Treatment and Prevention

In one embodiment, provided herein is a method of treating and preventing cancer, which comprises administering to a patient a compound provided herein, e.g., the compound of Formula I, or an enantiomer or a mixture of enantiomers thereof, or a pharmaceutically acceptable salt, solvate, hydrate, co-crystal, clathrate, or polymorph thereof.

In another embodiment, provided herein is method of managing cancer, which comprises administering to a patient a compound provided herein, e.g., the compound of Formula I, or an enantiomer or a mixture of enantiomers thereof, or a pharmaceutically acceptable salt, solvate, hydrate, co-crystal, clathrate, or polymorph thereof.

Also provided herein are methods of treating patients who have been previously treated for cancer but are non-responsive to standard therapies, as well as those who have not previously been treated. The invention also encompasses methods of treating patients regardless of patient's age, although some diseases or disorders are more common in certain age groups. The invention further encompasses methods of treating patients who have undergone surgery in an attempt to treat the disease or condition at issue, as well as those who have not. Because patients with cancer have heterogeneous clinical manifestations and varying clinical outcomes, the treatment given to a patient may vary, depending on his/her prognosis. The skilled clinician will be able to readily determine without undue experimentation specific secondary agents, types of surgery, and types of non-drug based standard therapy that can be effectively used to treat an individual patient with cancer.

As used herein, the term "cancer" includes, but is not limited to, solid tumors and blood borne tumors. The term "cancer" refers to disease of skin tissues, organs, blood, and vessels, including, but not limited to, cancers of the bladder, bone, blood, brain, breast, cervix, chest, colon, endometrium, esophagus, eye, head, kidney, liver, lymph nodes, lung, mouth, neck, ovaries, pancreas, prostate, rectum, stomach, testis, throat, and uterus. Specific cancers include, but are not limited to, advanced malignancy, amyloidosis, neuroblastoma, meningioma, hemangiopericytoma, multiple brain metastases, glioblastoma multiforms, glioblastoma, brain stem glioma, poor prognosis malignant brain tumor, malignant glioma, recurrent malignant glioma, anaplastic astrocytoma, anaplastic oligodendroglioma, neuroendocrine tumor, rectal adenocarcinoma, Dukes C & D colorectal cancer, unresectable colorectal carcinoma, metastatic hepatocellular carcinoma, Kaposi's sarcoma, karotype acute myeloblastic leukemia, Hodgkin's lymphoma, non-Hodgkin's lymphoma, cutaneous T-Cell lymphoma, cutaneous B-Cell lymphoma, diffuse large B-Cell lymphoma, low grade follicular lymphoma, malignant melanoma, malignant mesothelioma, malignant pleural effusion mesothelioma syndrome, peritoneal carcinoma, papillary serous carcinoma, gynecologic sarcoma, soft tissue sarcoma, scleroderma, cutaneous vasculitis, Langerhans cell histiocytosis, leiomyosarcoma, fibrodysplasia ossificans progressive, hormone refractory prostate cancer, resected high-risk soft tissue sarcoma, unresectable hepatocellular carcinoma, Waldenstrom's macroglobulinemia, smoldering myeloma, indolent myeloma, fallopian tube cancer, androgen independent prostate cancer, androgen dependent stage IV non-metastatic prostate cancer, hormone-insensitive prostate cancer, chemotherapy-insensitive prostate cancer, urachal cancer, papillary thyroid carcinoma, follicular thyroid carcinoma, medullary thyroid carcinoma, and leiomyoma In certain embodiments, the cancer is a solid tumor. In certain embodiments, the solid tumor is metastatic. In certain embodiments, the solid tumor is drug-resistant. In certain embodiments, the solid tumor is hepatocellular carcinoma, prostate cancer, ovarian cancer, or glioblastoma.

In certain embodiments, the cancer is a blood borne tumor. In certain embodiments, the blood borne tumor is metastatic. In certain embodiments, the blood borne tumor is drug resistant. In certain embodiments, the cancer is leukemia.

In one embodiment, methods provided herein encompass treating, preventing or managing various types of leukemias such as chronic lymphocytic leukemia (CLL), chronic myelocytic leukemia (CML), acute lymphoblastic leukemia (ALL), acute myeloid leukemia (AML), and acute myeloblastic leukemia (AML) by administering a therapeutically effective amount of a compound of formula I or an enantiomer or a mixture of enantiomers thereof, or a pharmaceutically acceptable salt, solvate, hydrate, co-crystal, clathrate, or polymorph thereof.

In some embodiments, the methods provided herein encompass treating, preventing or managing acute leukemia in a subject. In some embodiments, the acute leukemia is acute myeloid leukemia (AML), which includes, but is not limited to, undifferentiated AML (M0), myeloblastic leukemia (M1), myeloblastic leukemia (M2), promyelocytic leukemia (M3 or M3 variant [M3V]), myelomonocytic leukemia (M4 or M4 variant with eosinophilia [M4E]), monocytic leukemia (M5), erythroleukemia (M6), and megakaryoblastic leukemia (M7). In one embodiment, the acute myeloid leukemia is undifferentiated AML (M0). In one embodiment, the acute myeloid leukemia is myeloblastic leukemia (M1). In one embodiment, the acute myeloid leukemia is myeloblastic leukemia (M2). In one embodiment, the acute myeloid leukemia is promyelocytic leukemia (M3 or M3 variant [M3V]). In one embodiment, the acute myeloid leukemia is myelomonocytic leukemia (M4 or M4 variant with eosinophilia [M4E]). In one embodiment, the acute myeloid leukemia is monocytic leukemia (M5). In one embodiment, the acute myeloid leukemia is erythroleukemia (M6). In one embodiment, the acute myeloid leukemia is megakaryoblastic leukemia (M7). Thus, the methods of treating, preventing or managing acute myeloid leukemia in a subject comprise the step of administering to the subject an amount of a compound provided herein or an enantiomer or a mixture of enantiomers thereof, or a pharmaceutically acceptable salt, solvate, hydrate, co-crystal, clathrate, or polymorph thereof effective to treat, prevent or manage acute myeloid leukemia alone or in combination. In some embodiments, the methods comprise the step of administering to the subject a compound provided herein or an enantiomer or a mixture of enantiomers thereof, or a pharmaceutically acceptable salt, solvate, hydrate, co-crystal, clathrate, or polymorph thereof in combination with a second active agent in amounts effective to treat, prevent or manage acute myeloid leukemia.

In some embodiments, the methods provided herein encompass treating, preventing or managing acute lymphocytic leukemia (ALL) in a subject. In some embodiments, acute lymphocytic leukemia includes leukemia that originates in the blast cells of the bone marrow (B-cells), thymus (T-cells), and lymph nodes. The acute lymphocytic leukemia can be categorized according to the French-American-British (FAB) Morphological Classification Scheme as L1—Mature-appearing lymphoblasts (T-cells or pre-B-cells), L2—Immature and pleomorphic (variously shaped) lymphoblasts (T-cells or pre-B-cells), and L3—Lymphoblasts (B-cells; Burkitt's cells). In one embodiment, the acute lymphocytic leukemia originates in the blast cells of the bone marrow (B-cells). In one embodiment, the acute lymphocytic leukemia originates in the thymus (T-cells). In one embodiment, the acute lymphocytic leukemia originates in the lymph nodes. In one embodiment, the acute lymphocytic leukemia is L1 type characterized by mature-appearing lymphoblasts (T-cells or pre-B-cells). In one embodiment, the acute lymphocytic leukemia is L2 type characterized by immature and pleomorphic (variously shaped) lymphoblasts (T-cells or pre-B-cells). In one embodiment, the acute lymphocytic leukemia is L3 type characterized by lymphoblasts (B-cells; Burkitt's cells). In certain embodiments, the acute lymphocytic leukemia is T-cell leukemia. In one embodiment, the T-cell leukemia is peripheral T-cell leukemia. In another embodiment, the T-cell leukemia is T-cell lymphoblastic leukemia. In another embodiment, the T-cell leukemia is cutaneous T-cell leukemia. In another embodiment, the T-cell leukemia is adult T-cell leukemia. Thus, the methods of treating, preventing or managing acute lymphocytic leukemia in a subject comprise the step of administering to the subject an amount of a compound provided herein or an enantiomer or a mixture of enantiomers thereof, or a pharmaceutically acceptable salt, solvate, hydrate, co-crystal, clathrate, or polymorph thereof effective to treat, prevent or manage acute lymphocytic leukemia alone or in combination with a second active agent. In some embodiments, the methods comprise the step of administering to the subject a compound provided herein or an enantiomer or a mixture of enantiomers thereof, or a pharmaceutically acceptable salt, solvate, hydrate, co-crystal, clathrate, or polymorph thereof in combination with a second active agent in amounts effective to treat, prevent or manage acute lymphocytic leukemia.

In some embodiments, the methods provided herein encompass treating, preventing or managing chronic myelogenous leukemia (CML) in a subject. The methods comprise the step of administering to the subject an amount of a compound provided herein or an enantiomer or a mixture of enantiomers thereof, or a pharmaceutically acceptable salt, solvate, hydrate, co-crystal, clathrate, or polymorph thereof effective to treat, prevent or manage chronic myelogenous leukemia. In some embodiments, the methods comprise the step of administering to the subject a compound provided herein or an enantiomer or a mixture of enantiomers thereof, or a pharmaceutically acceptable salt, solvate, hydrate, co-crystal, clathrate, or polymorph thereof in combination with a second active agent in amounts effective to treat, prevent or manage chronic myelogenous leukemia.

In some embodiments, the methods provided herein encompass treating, preventing or managing chronic lymphocytic leukemia (CLL) in a subject. The methods comprise the step of administering to the subject an amount of a compound provided herein or an enantiomer or a mixture of enantiomers thereof, or a pharmaceutically acceptable salt, solvate, hydrate, co-crystal, clathrate, or polymorph thereof effective to treat, prevent or manage chronic lymphocytic leukemia. In some embodiments, the methods comprise the step of administering to the subject a compound provided herein or an enantiomer or a mixture of enantiomers thereof, or a pharmaceutically acceptable salt, solvate, hydrate, co-crystal, clathrate, or polymorph thereof in combination with a second active agent in amounts effective to treat, prevent or manage chronic lymphocytic leukemia.

In certain embodiments, provided herein are methods of treating, preventing, and/or managing disease in patients with impaired renal function. In certain embodiments, provided herein are method of treating, preventing, and/or managing cancer in patients with impaired renal function. In certain embodiments, provided herein are methods of providing appropriate dose adjustments for patients with impaired renal function due to, but not limited to, disease, aging, or other patient factors.

In certain embodiments, provided herein are methods of treating, preventing, and/or managing lymphoma, including non-Hodgkin's lymphoma. In some embodiments, provided herein are methods for the treatment or management of non-Hodgkin's lymphoma (NHL), including but not limited to, diffuse large B-cell lymphoma (DLBCL), using prognostic factors.

In certain embodiments, provided herein are methods of treating, preventing, and/or managing multiple myeloma, including relapsed/refractory multiple myeloma in patients with impaired renal function or a symptom thereof, comprising administering a therapeutically effective amount of the compound of Formula I, or an enantiomer or a mixture of enantiomers thereof, or a pharmaceutically acceptable salt, solvate, hydrate, stereoisomer, tautomer or racemic mixtures thereof to a patient having relapsed/refractory multiple myeloma with impaired renal function.

In certain embodiments, a therapeutically or prophylactically effective amount of the compound is from about 0.005 to about 1,000 mg per day, from about 0.01 to about 500 mg per day, from about 0.01 to about 250 mg per day, from about 0.01 to about 100 mg per day, from about 0.1 to about 100 mg per day, from about 0.5 to about 100 mg per day, from about 1 to about 100 mg per day, from about 0.01 to about 50 mg per day, from about 0.1 to about 50 mg per day, from about 0.5 to about 50 mg per day, from about 1 to about 50 mg per day, from about 0.02 to about 25 mg per day, from about 0.05 to about 10 mg per day, from about 0.05 to about 5 mg per day, from about 0.1 to about 5 mg per day, or from about 0.5 to about 5 mg per day.

In certain embodiments, the therapeutically or prophylactically effective amount is about 0.1, about 0.2, about 0.5, about 1, about 2, about 3, about 4, about 5, about 6, about 7, about 8, about 9, about 10, about 15, about 20, about 25, about 30, about 40, about 45, about 50, about 60, about 70, about 80, about 90, about 100, or about 150 mg per day. In some such embodiments, the therapeutically or prophylactically effective amount is about 2, about 3, about 4, about 5, about 6 or about 7 mg per day.

In one embodiment, the recommended daily dose range of the compound of Formula I, or an enantiomer or a mixture of enantiomers thereof, or a pharmaceutically acceptable salt, solvate, hydrate, co-crystal, clathrate, or polymorph thereof, for the conditions described herein lie within the range of from about 0.5 mg to about 50 mg per day, preferably given as a single once-a-day dose, or in divided doses throughout a day. In some embodiments, the dosage ranges from about 1 mg to about 50 mg per day. In other embodiments, the dosage ranges from about 0.5 to about 5 mg per day. Specific doses per day include 0.1, 0.2, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 mg per day.

In a specific embodiment, the recommended starting dosage may be 0.5, 1, 2, 3, 4, 5, 10, 15, 20, 25 or 50 mg per day. In another embodiment, the recommended starting dosage may be 0.5, 1, 2, 3, 4, or 5 mg per day. The dose may be escalated to 15, 20, 25, 30, 35, 40, 45 and 50 mg/day. In a specific embodiment, the compound can be administered in an amount of about 25 mg/day to patients with leukemia, including AML. In a particular embodiment, the compound can be administered in an amount of about 10 mg/day to patients with leukemia, including AML. In a particular embodiment, the compound can be administered in an amount of about 5 mg/day to patients with leukemia, including AML. In a particular embodiment, the compound can be administered in an amount of about 4 mg/day to patients with leukemia, including AML. In a particular embodiment, the compound can be administered in an amount of about 3 mg/day to patients with leukemia, including AML.

In certain embodiments, the therapeutically or prophylactically effective amount is from about 0.001 to about 100 mg/kg/day, from about 0.01 to about 50 mg/kg/day, from about 0.01 to about 25 mg/kg/day, from about 0.01 to about 10 mg/kg/day, from about 0.01 to about 9 mg/kg/day, 0.01 to about 8 mg/kg/day, from about 0.01 to about 7 mg/kg/day, from about 0.01 to about 6 mg/kg/day, from about 0.01 to about 5 mg/kg/day, from about 0.01 to about 4 mg/kg/day, from about 0.01 to about 3 mg/kg/day, from about 0.01 to about 2 mg/kg/day, from about 0.01 to about 1 mg/kg/day, or from about 0.01 to about 0.05 mg/kg/day.

The administered dose can also be expressed in units other than mg/kg/day. For example, doses for parenteral administration can be expressed as mg/m$^2$/day. One of ordinary skill in the art would readily know how to convert doses from mg/kg/day to mg/m$^2$/day to given either the height or weight of a subject or both (see, www.fda.gov/cder/cancer/animalframe.htm). For example, a dose of 1 mg/kg/day for a 65 kg human is approximately equal to 38 mg/m$^2$/day.

In certain embodiments, the amount of the compound administered is sufficient to provide a plasma concentration of the compound at steady state, ranging from about 0.001 to about 500 µM, about 0.002 to about 200 µM, about 0.005 to about 100 µM, about 0.01 to about 50 µM, from about 1 to about 50 µM, about 0.02 to about 25 µM, from about 0.05 to about 20 µM, from about 0.1 to about 20 µM, from about 0.5 to about 20 µM, or from about 1 to about 20 µM.

In other embodiments, the amount of the compound administered is sufficient to provide a plasma concentration of the compound at steady state, ranging from about 5 to about 100 nM, about 5 to about 50 nM, about 10 to about 100 nM, about 10 to about 50 nM or from about 50 to about 100 nM.

As used herein, the term "plasma concentration at steady state" is the concentration reached after a period of administration of a compound provided herein, e.g., the compound of Formula I, or an enantiomer or a mixture of enantiomers thereof, or a pharmaceutically acceptable salt, solvate, hydrate, co-crystal, clathrate, or polymorph thereof. Once steady state is reached, there are minor peaks and troughs on the time dependent curve of the plasma concentration of the compound.

In certain embodiments, the amount of the compound administered is sufficient to provide a maximum plasma concentration (peak concentration) of the compound, ranging from about 0.001 to about 500 µM, about 0.002 to about 200 µM, about 0.005 to about 100 µM, about 0.01 to about 50 µM, from about 1 to about 50 µM, about 0.02 to about 25 µM, from about 0.05 to about 20 µM, from about 0.1 to about 20 µM, from about 0.5 to about 20 µM, or from about 1 to about 20 µM.

In certain embodiments, the amount of the compound administered is sufficient to provide a minimum plasma concentration (trough concentration) of the compound, ranging from about 0.001 to about 500 µM, about 0.002 to about 200 µM, about 0.005 to about 100 µM, about 0.01 to about 50 µM, from about 1 to about 50 µM, about 0.01 to about 25 µM, from about 0.01 to about 20 µM, from about 0.02 to about 20 PM, from about 0.02 to about 20 µM, or from about 0.01 to about 20 µM.

In certain embodiments, the amount of the compound administered is sufficient to provide an area under the curve (AUC) of the compound, ranging from about 100 to about 100,000 ng*hr/mL, from about 1,000 to about 50,000 ng*hr/mL, from about 5,000 to about 25,000 ng*hr/mL, or from about 5,000 to about 10,000 ng*hr/mL.

In certain embodiments, the patient to be treated with one of the methods provided herein has not been treated with anticancer therapy prior to the administration of the compound of Formula I, or an enantiomer or a mixture of enantiomers thereof, or a pharmaceutically acceptable salt, solvate, hydrate, co-crystal, clathrate, or polymorph thereof. In certain embodiments, the patient to be treated with one of the methods provided herein has been treated with anticancer therapy prior to the administration of the compound of Formula I, or an enantiomer or a mixture of enantiomers thereof, or a pharmaceutically acceptable salt, solvate, hydrate, co-crystal, clathrate, or polymorph thereof. In certain embodiments, the patient to be treated with one of the methods provided herein has developed drug resistance to the anticancer therapy.

The methods provided herein encompass treating a patient regardless of patient's age, although some diseases or disorders are more common in certain age groups.

Depending on the disease to be treated and the subject's condition, the compound of Formula I, or an enantiomer or a mixture of enantiomers thereof; or a pharmaceutically acceptable salt, solvate, hydrate, co-crystal, clathrate, or polymorph thereof, may be administered by oral, parenteral (e.g., intramuscular, intraperitoneal, intravenous, CIV, intracisternal injection or infusion, subcutaneous injection, or implant), inhalation, nasal, vaginal, rectal, sublingual, or topical (e.g., transdermal or local) routes of administration. The compound of Formula I, or an enantiomer or a mixture of enantiomers thereof; or a pharmaceutically acceptable salt, solvate, hydrate, co-crystal, clathrate, or polymorph thereof, may be formulated, alone or together, in suitable dosage unit with pharmaceutically acceptable excipients, carriers, adjuvants and vehicles, appropriate for each route of administration.

In one embodiment, the compound of Formula I, or an enantiomer or a mixture of enantiomers thereof; or a pharmaceutically acceptable salt, solvate, hydrate, co-crystal, clathrate, or polymorph thereof, is administered orally. In another embodiment, the compound of Formula I, or an enantiomer or a mixture of enantiomers thereof; or a pharmaceutically acceptable salt, solvate, hydrate, co-crystal, clathrate, or polymorph thereof, is administered parenterally. In yet another embodiment, the compound of Formula I, or an enantiomer or a mixture of enantiomers thereof; or a pharmaceutically acceptable salt, solvate, hydrate, co-crystal, clathrate, or polymorph thereof, is administered intravenously.

The compound of Formula I, or an enantiomer or a mixture of enantiomers thereof; or a pharmaceutically acceptable salt, solvate, hydrate, co-crystal, clathrate, or polymorph thereof, can be delivered as a single dose such as, e.g., a single bolus injection, or oral tablets or pills; or over time, such as, e.g., continuous infusion over time or divided bolus doses over time. The compound can be administered repeatedly if necessary, for example, until the patient experiences stable disease or regression, or until the patient experiences disease progression or unacceptable toxicity. For example, stable disease for solid tumors generally means that the perpendicular diameter of measurable lesions has not increased by 25% or more from the last measurement. Response Evaluation Criteria in Solid Tumors (RE- CIST) Guidelines, *Journal of the National Cancer Institute* 92(3): 205-216 (2000). Stable disease or lack thereof is determined by methods known in the art such as evaluation of patient symptoms, physical examination, visualization of the tumor that has been imaged using X-ray, CAT, PET, or MRI scan and other commonly accepted evaluation modalities.

The compound of Formula I, or an enantiomer or a mixture of enantiomers thereof; or a pharmaceutically acceptable salt, solvate, hydrate, co-crystal, clathrate, or polymorph thereof, can be administered once daily (QD), or divided into multiple daily doses such as twice daily (BID), three times daily (TID), and four times daily (QID). In addition, the administration can be continuous (i.e., daily for consecutive days or every day), intermittent, e.g., in cycles (i.e., including days, weeks, or months of rest without drug). As used herein, the term "daily" is intended to mean that a therapeutic compound, such as the compound of Formula I, is administered once or more than once each day, for example, for a period of time. The term "continuous" is intended to mean that a therapeutic compound, such as the compound of Formula I, is administered daily for an uninterrupted period of at least 10 days to 52 weeks. The term "intermittent" or "intermittently" as used herein is intended to mean stopping and starting at either regular or irregular intervals. For example, intermittent administration of the compound of Formula I is administration for one to six days per week, administration in cycles (e.g., daily administration for two to eight consecutive weeks, then a rest period with no administration for up to one week), or administration on alternate days. The term "cycling" as used herein is intended to mean that a therapeutic compound, such as the compound of Formula I, is administered daily or continuously but with a rest period. In some such embodiments, administration is once a day for two to six days, then a rest period with no administration for five to seven days.

In some embodiments, the frequency of administration is in the range of about a daily dose to about a monthly dose. In certain embodiments, administration is once a day, twice a day, three times a day, four times a day, once every other day, twice a week, once every week, once every two weeks, once every three weeks, or once every four weeks. In one embodiment, the compound of Formula I, or an enantiomer or a mixture of enantiomers thereof; or a pharmaceutically acceptable salt, solvate, hydrate, co-crystal, clathrate, or polymorph thereof, is administered once a day. In another embodiment, the compound of Formula I, or an enantiomer or a mixture of enantiomers thereof; or a pharmaceutically acceptable salt, solvate, hydrate, co-crystal, clathrate, or polymorph thereof, is administered twice a day. In yet another embodiment, the compound of Formula I, or an enantiomer or a mixture of enantiomers thereof; or a pharmaceutically acceptable salt, solvate, hydrate, co-crystal, clathrate, or polymorph thereof, is administered three times a day. In still another embodiment, the compound of Formula I, or an enantiomer or a mixture of enantiomers thereof; or a pharmaceutically acceptable salt, solvate, hydrate, co-crystal, clathrate, or polymorph thereof, is administered four times a day.

In certain embodiments, the compound of Formula I, or an enantiomer or a mixture of enantiomers thereof; or a pharmaceutically acceptable salt, solvate, hydrate, co-crystal, clathrate, or polymorph thereof, is administered once per day from one day to six months, from one week to three months, from one week to four weeks, from one week to three weeks, or from one week to two weeks. In certain embodiments, the compound of Formula I, or a pharmaceutically acceptable salt or solvate thereof, is administered once per day for one week, two weeks, three weeks, or four weeks. In one embodiment, the compound of Formula I, or an enantiomer or a mixture of enantiomers thereof; or a pharmaceutically acceptable salt, solvate, hydrate, co-crystal, clathrate, or polymorph thereof, is administered once per day for 4 days. In one embodiment, the compound of Formula I, or an enantiomer or a mixture of enantiomers thereof; or a pharmaceutically acceptable salt, solvate, hydrate, co-crystal, clathrate, or polymorph thereof, is administered once per day for 5 days. In one embodiment, the compound of Formula I, or an enantiomer or a mixture of enantiomers thereof; or a pharmaceutically acceptable salt, solvate, hydrate, co-crystal, clathrate, or polymorph thereof, is administered once per day for 6 days. In one embodiment, the compound of Formula I, or an enantiomer or a mixture of enantiomers thereof; or a pharmaceutically acceptable salt, solvate, hydrate, co-crystal, clathrate, or polymorph thereof, is administered once per day for one week. In another embodiment, the compound of Formula I, or an enantiomer or a mixture of enantiomers thereof; or a pharmaceutically acceptable salt, solvate, hydrate, co-crystal, clathrate, or polymorph thereof, is administered once per day for two weeks. In yet another embodiment, the compound of Formula I, or an enantiomer or a mixture of enantiomers thereof; or a pharmaceutically acceptable salt, solvate, hydrate, co-crystal, clathrate, or polymorph thereof, is administered once per day for three weeks. In still another embodiment, the compound of Formula I, or an enantiomer or a mixture of enantiomers thereof; or a pharmaceutically acceptable salt, solvate, hydrate, co-crystal, clathrate, or polymorph thereof, is administered once per day for four weeks.

C-1. Combination Therapy with a Second Active Agent

The compound of Formula I, or an enantiomer or a mixture of enantiomers thereof; or a pharmaceutically acceptable salt, solvate, hydrate, co-crystal, clathrate, or polymorph thereof, can also be combined or used in combination with other therapeutic agents useful in the treatment and/or prevention of cancer described herein.

In one embodiment, provided herein is a method of treating, preventing, or managing cancer, comprising administering to a patient a compound of Formula I, or an enantiomer or a mixture of enantiomers thereof; or a pharmaceutically acceptable salt, solvate, hydrate, co-crystal, clathrate, or polymorph thereof; in combination with one or more second active agents, and optionally in combination with radiation therapy, blood transfusions, or surgery. Examples of second active agents are disclosed herein (see, e.g., section 5.4).

As used herein, the term "in combination" includes the use of more than one therapy (e.g., one or more prophylactic and/or therapeutic agents). However, the use of the term "in combination" does not restrict the order in which therapies (e.g., prophylactic and/or therapeutic agents) are administered to a patient with a disease or disorder. A first therapy (e.g., a prophylactic or therapeutic agent such as a compound provided herein, a compound provided herein, e.g., the compound of Formula I, or an enantiomer or a mixture of enantiomers thereof, or a pharmaceutically acceptable salt, solvate, hydrate, co-crystal, clathrate, or polymorph thereof) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent) to the subject. Triple therapy is also contemplated herein.

Administration of the compound of Formula I and one or more second active agents to a patient can occur simultaneously or sequentially by the same or different routes of administration. The suitability of a particular route of administration employed for a particular active agent will depend on the active agent itself (e.g., whether it can be administered orally without decomposing prior to entering the blood stream) and the cancer being treated.

The route of administration of the compound of Formula I is independent of the route of administration of a second therapy. In one embodiment, the compound of Formula I is administered orally. In another embodiment, the compound of Formula I is administered intravenously. Thus, in accordance with these embodiments, the compound of Formula I is administered orally or intravenously, and the second therapy can be administered orally, parenterally, intraperitoneally, intravenously, intraarterially, transdermally, sublingually, intramuscularly, rectally, transbuccally, intranasally, liposomally, via inhalation, vaginally, intraocularly, via local delivery by catheter or stent, subcutaneously, intraadiposally, intraarticularly, intrathecally, or in a slow release dosage form. In one embodiment, the compound of Formula I and a second therapy are administered by the same mode of administration, orally or by IV. In another embodiment, the compound of Formula I is administered by one mode of administration, e.g., by IV, whereas the second agent (an anticancer agent) is administered by another mode of administration, e.g., orally.

In one embodiment, the second active agent is administered intravenously or subcutaneously and once or twice daily in an amount of from about 1 to about 1000 mg, from about 5 to about 500 mg, from about 10 to about 350 mg, or from about 50 to about 200 mg. The specific amount of the second active agent will depend on the specific agent used, the type of disease being treated or managed, the severity and stage of disease, and the amount of the compound of Formula I provided herein and any optional additional active agents concurrently administered to the patient.

One or more second active ingredients or agents can be used together with the compound of formula I in the methods and compositions provided herein. Second active agents can be large molecules (e.g., proteins) or small molecules (e.g., synthetic inorganic, organometallic, or organic molecules).

Examples of large molecule active agents include, but are not limited to, hematopoietic growth factors, cytokines, and monoclonal and polyclonal antibodies, particularly, therapeutic antibodies to cancer antigens. Typical large molecule active agents are biological molecules, such as naturally occurring or synthetic or recombinant proteins. Proteins that are particularly useful in the methods and compositions provided herein include proteins that stimulate the survival and/or proliferation of hematopoietic precursor cells and immunologically active poietic cells in vitro or in vivo. Other useful proteins stimulate the division and differentiation of committed erythroid progenitors in cells in vitro or in vivo. Particular proteins include, but are not limited to: interleukins, such as IL-2 (including recombinant IL-II ("rIL2") and canarypox IL-2), IL-10, IL-12, and IL-18; interferons, such as interferon alfa-2a, interferon alfa-2b, interferon alfa-n1, interferon alfa-n3, interferon beta-I a, and interferon gamma-I b; GM-CF and GM-CSF; and EPO.

In certain embodiments, GM-CSF, G-CSF, SCF or EPO is administered subcutaneously during about five days in a four or six week cycle in an amount ranging from about 1 to about 750 mg/m$^2$/day, from about 25 to about 500 mg/m$^2$/day, from about 50 to about 250 mg/m$^2$/day, or from about 50 to about 200 mg/m$^2$/day. In certain embodiments, GM-CSF may be administered in an amount of from about 60 to about 500 mcg/m$^2$ intravenously over 2 hours or from about 5 to about 12 mcg/m$^2$/day subcutaneously. In certain embodiments, G-CSF may be administered subcutaneously in an amount of about 1 mcg/kg/day initially and can be adjusted depending on rise of total granulocyte counts. The maintenance dose of G-CSF may be administered in an amount of about 300 (in smaller patients) or 480 mcg subcutaneously. In certain embodiments, EPO may be administered subcutaneously in an amount of 10,000 Unit 3 times per week.

Particular proteins that can be used in the methods and compositions include, but are not limited to: filgrastim, which is sold in the United States under the trade name Neupogen® (Amgen, Thousand Oaks, Calif.); sargramostim, which is sold in the United States under the trade name Leukine® (Immunex, Seattle, Wash.); and recombinant EPO, which is sold in the United States under the trade name Epogen® (Amgen, Thousand Oaks, Calif.).

Recombinant and mutated forms of GM-CSF can be prepared as described in U.S. Pat. Nos. 5,391,485; 5,393,870; and 5,229,496; all of which are incorporated herein by reference. Recombinant and mutated forms of G-CSF can be prepared as described in U.S. Pat. Nos. 4,810,643; 4,999,291; 5,528,823; and 5,580,755; the entireties of which are incorporated herein by reference.

Also provided for use in combination with a compound provided herein or an enantiomer or a mixture of enantiomers thereof, or a pharmaceutically acceptable salt, solvate, hydrate, co-crystal, clathrate, or polymorph thereof are native, naturally occurring, and recombinant proteins. Further encompassed are mutants and derivatives (e.g., modified forms) of naturally occurring proteins that exhibit, in vivo, at least some of the pharmacological activity of the proteins upon which they are based. Examples of mutants include, but are not limited to, proteins that have one or more amino acid residues that differ from the corresponding residues in the naturally occurring forms of the proteins. Also encompassed by the term "mutants" are proteins that lack carbohydrate moieties normally present in their naturally occurring forms (e.g., nonglycosylated forms). Examples of derivatives include, but are not limited to, pegylated derivatives and fusion proteins, such as proteins formed by fusing IgG1 or IgG3 to the protein or active portion of the protein of interest. See, e.g., Penichet, M. L. and Morrison, S. L., *J. Immunol. Methods* 248:91-101 (2001).

Antibodies that can be used in combination with a compound provided herein or an enantiomer or a mixture of enantiomers thereof, or a pharmaceutically acceptable salt, solvate, hydrate, co-crystal, clathrate, or polymorph thereof include monoclonal and polyclonal antibodies. Examples of antibodies include, but are not limited to, trastuzumab (Herceptin®), rituximab (Rituxan®), bevacizumab (Avastin™), pertuzumab (Omnitarg™), tositumomab (Bexxar®), edrecolomab (Panorex®), and G250. The compounds provided herein or an enantiomer or a mixture of enantiomers thereof, or a pharmaceutically acceptable salt, solvate, hydrate, co-crystal, clathrate, or polymorph thereof can also be combined with, or used in combination with, anti-TNF-α antibodies, and/or anti-EGFR antibodies, such as, for example, Erbitux® or panitumumab.

Additional anticancer drugs that may be included in the present invention are antibody drug conjugates (ADC). An antibody-drug-conjugate consists of 3 components: Antibody, Payload and Linker. The Antibody targets the ADC and may also elicit a therapeutic response. The Payload elicits the desired therapeutic response. The Linker attaches the payload to the antibody and should be stable in circulation only releasing the payload at the desired target. An anticancer drug (Payload) is coupled via the Linker to an Antibody that specifically targets a certain tumor antigen (e.g. a protein that, ideally, is only to be found in or on tumor cells). Antibodies attach themselves to the antigens on the surface of cancerous cells. The biochemical reaction between the antibody and the target protein (antigen) triggers a signal in the tumor cell, which then absorbs or internalizes the antibody together with the linked Payload. After the ADC is internalized, the Payload kills the cancer. This targeting limits side effects and gives a wider therapeutic window than other chemotherapeutic agents. In certain embodiments, the compounds of Formula I can be incorporated as the Payload linked to the Antibody.

Large molecule active agents may be administered in the form of anti-cancer vaccines. For example, vaccines that secrete, or cause the secretion of, cytokines such as IL-2, G-CSF, and GM-CSF can be used in the methods and pharmaceutical compositions provided. See, e.g., Emens, L. A., et al., Curr. Opinion Mol. Ther. 3(1):77-84 (2001).

Second active agents that are small molecules can also be used to alleviate adverse effects associated with the administration of a compound provided herein or an enantiomer or a mixture of enantiomers thereof, or a pharmaceutically acceptable salt, solvate, hydrate, co-crystal, clathrate, or polymorph thereof. However, like some large molecules, many are believed to be capable of providing a synergistic effect when administered with (e.g., before, after or simultaneously) a compound provided herein or an enantiomer or a mixture of enantiomers thereof, or a pharmaceutically acceptable salt, solvate, hydrate, co-crystal, clathrate, or polymorph thereof. Examples of small molecule second active agents include, but are not limited to, anti-cancer agents, antibiotics, immunosuppressive agents, and steroids.

In certain embodiments, the second agent is an HSP inhibitor, a proteasome inhibitor, a FLT3 inhibitor, a TOR kinase inhibitor, an antineoplastic, a tyrosine kinase inhibitor, a hedgehog pathway inhibitor, a Bcl-2 inhibitor, or an isocitrate dehydrogenase (IDH) inhibitor.

Examples of anti-cancer agents to be used within the methods or compositions described herein include, but are not limited to: acivicin; aclarubicin; acodazole hydrochloride; acronine; adozelesin; aldesleukin; altretamine; ambomycin; ametantrone acetate; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; celecoxib (COX-2 inhibitor); cerubidine; chlorambucil; cirolemycin; cisplatin; cladribine; clofarabine; crisnatol mesylate; cytarabine; cyclophosphamide; Ara-C; dacarbazine; dactinomycin; daunorubicin hydrochloride; daunorubicin hydrochloride and cytarabine liposome; daurismo; decitabine; dexormaplatin; dexamethasone; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enasidenib mesylate; enloptatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; gemtuzumab ozogamcin; hydroxyurea; ibrutinib; idarubicin hydrochloride; ifosfamide; ilmofosine; iproplatin; irinotecan; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; omacetaxine; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; safingol; safingol hydrochloride; semustine; simtrazene; sorafenib; sparfosate sodium; sparsomycin; spirogermanium hydrochloride; spiromustine; spiroplatin; streptonigrin; streptozocin; sulofenur; talisomycin; tecogalan sodium; taxotere; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; venetoclax; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other anti-cancer drugs to be included within the methods or compositions include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; arsenic trioxide; asulacrine; atamestane; atrimustine; axinastatin 1; axinastatin 2; axinastatin 3; azacytidine; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; capecitabine; carboxamide-amino-triazole; carboxyamidotriazole; CaRest M3; CARN 700; cartilage derived inhibitor; carzelesin;

casein kinase inhibitors (ICOS); castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cyclophosphamide; cycloplatam; cypemycin; Ara-C ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; doxorubicin; droloxifene; dronabinol; duocarmycin SA; ebselen; ecomustine; edelfosine; edrecolomab; eflornithine; elemene; emitefur; enasidenib; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; gemtuzumab; gilteritinib; glasdegib; glutathione inhibitors; hepsulfam; heregulin; hexamethylene bisacetamide; hypericin; ibandronic acid; idarubicin; idoxifene; idramantone; ilmofosine; ilomastat; imatinib (e.g., Gleevec®); imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; ivosidenib; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; midostaurin; MIF inhibitor; mifepristone; miltefosine; mirimostim; mitoguazone; mitolactol; mitomycin analogues; mitonafide; mitotoxin fibroblast growth factor-saporin; mitoxantrone; mofarotene; molgramostim; Mylotarg; Erbitux, human chorionic gonadotrophin; monophosphoryl lipid A+myobacterium cell wall sk; mopidamol; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; nilutamide; nisamycin; nitric oxide modulators; nitroxide antioxidant; nitrullyn; oblimersen (Genasense®); O⁶-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stipiamide; stromelysin inhibitors; sulfinosine; superactive vasoactive intestinal peptide antagonist; suradista; suramin; swainsonine; tallimustine; tamoxifen methiodide; tauromustine; tazarotene; tecogalan sodium; tegafur; tellurapyrylium; telomerase inhibitors; temoporfin; teniposide; tetrachlorodecaoxide; tetrazomine; thaliblastine; thiocoraline; thioguanine; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; velaresol; veramine; verdins; verteporfin; vincristine sulfate; vinorelbine; vinxaltine; vitaxin; vorozole; zanoterone; zeniplatin; zilascorb; and zinostatin stimalamer. Specific second active agents particularly useful in the methods or compositions include, but are not limited to, rituximab, oblimersen (Genasense®), remicade, docetaxel, celecoxib, melphalan, dexamethasone (Decadron®), steroids, gemcitabine, cis-platinum, temozolomide, etoposide, cyclophosphamide, temodar, carboplatin, procarbazine, gliadel, tamoxifen, topotecan, methotrexate, Arisa®, taxol, taxotere, fluorouracil, leucovorin, irinotecan, xeloda, CPT-11, interferon alpha, pegylated interferon alpha (e.g., PEG INTRON-A), capecitabine, cisplatin, thiotepa, fludarabine, carboplatin, liposomal daunorubicin, Ara-C, doxetaxol, paclitaxel, vinblastine, IL-2, GM-CSF, dacarbazine, vinorelbine, zoledronic acid, palmitronate, biaxin, busulphan, prednisone, bisphosphonate, arsenic trioxide, vincristine, doxorubicin (Doxil®), paclitaxel, ganciclovir, adriamycin, estramustine sodium phosphate (Emcyt®), sulindac, and etoposide.

In certain embodiments of the methods provided herein, use of a second active agent in combination with a compound provided herein or an enantiomer or a mixture of enantiomers thereof, or a pharmaceutically acceptable salt, solvate, hydrate, co-crystal, clathrate, or polymorph thereof may be modified or delayed during or shortly following administration of a compound provided herein or an enantiomer or a mixture of enantiomers thereof, or a pharmaceutically acceptable salt, solvate, hydrate, co-crystal, clathrate, or polymorph thereof as deemed appropriate by the practitioner of skill in the art. In certain embodiments, subjects being administered a compound provided herein or an enantiomer or a mixture of enantiomers thereof, or a pharmaceutically acceptable salt, solvate, hydrate, co-crystal, clathrate, or polymorph thereof alone or in combination with other therapies may receive supportive care including antiemetics, myeloid growth factors, and transfusions of platelets, when appropriate. In some embodiments, subjects being administered a compound provided herein or an enantiomer or a mixture of enantiomers thereof, or a pharmaceutically acceptable salt, solvate, hydrate, co-crystal, clathrate, or polymorph thereof may be administered a growth factor as a second active agent according to the judgment of the practitioner of skill in the art. In some embodiments, provided is administration of a compound provided herein or an enantiomer or a mixture of enantiomers thereof, or a pharmaceutically acceptable salt, solvate, hydrate, co-crystal, clathrate, or polymorph thereof in combination with erythropoietin or darbepoetin (Aranesp).

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered with gemcitabine and cisplatinum to patients with locally advanced or metastatic transitional cell bladder cancer.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered in combination with a second active ingredient as follows: temozolomide to pediatric patients with relapsed or progressive brain tumors or recurrent neuroblastoma; celecoxib, etoposide and cyclophosphamide for relapsed or progressive CNS cancer; temodar to patients with recurrent or progressive meningioma, malignant meningioma, hemangiopericytoma, multiple brain metastases, relapased brain tumors, or newly diagnosed glioblastoma multiforms; irinotecan to patients with recurrent glioblastoma; carboplatin to pediatric patients with brain stem glioma; procarbazine to pediatric patients with progressive malignant gliomas; cyclophosphamide to patients with poor prognosis malignant brain tumors, newly diagnosed or recurrent glioblastoma multiforms; Gliadel® for high grade recurrent malignant gliomas; temozolomide and tamoxifen for anaplastic astrocytoma; or topotecan for gliomas, glioblastoma, anaplastic astrocytoma or anaplastic oligodendroglioma.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered with methotrexate, cyclophosphamide, taxane, abraxane, lapatinib, herceptin, aromatase inhibitors, selective estrogen modulators, estrogen receptor antagonists, and/or PLX3397 (Plexxikon) to patients with metastatic breast cancer. In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered with temozolomide to patients with neuroendocrine tumors.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered with gemcitabine to patients with recurrent or metastatic head or neck cancer.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered with gemcitabine to patients with pancreatic cancer.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered to patients with colon cancer in combination with ARISA®, avastatin, taxol, and/or taxotere.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered with capecitabine and/or PLX4032 (Plexxikon) to patients with refractory colorectal cancer or patients who fail first line therapy or have poor performance in colon or rectal adenocarcinoma.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered in combination with fluorouracil, leucovorin, and irinotecan to patients with Dukes C & D colorectal cancer or to patients who have been previously treated for metastatic colorectal cancer.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered to patients with refractory colorectal cancer in combination with capecitabine, xeloda, and/or CPT-11.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered with capecitabine and irinotecan to patients with refractory colorectal cancer or to patients with unresectable or metastatic colorectal carcinoma.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered alone or in combination with interferon alpha or capecitabine to patients with unresectable or metastatic hepatocellular carcinoma; or with cisplatin and thiotepa to patients with primary or metastatic liver cancer.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered in combination with pegylated interferon alpha to patients with Kaposi's sarcoma.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered in combination with fludarabine, carboplatin, and/or topotecan to patients with refractory or relapsed or high-risk acute myeloid leukemia.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered in combination with liposomal daunorubicin, topotecan and/or cytarabine to patients with unfavorable karotype acute myeloblastic leukemia.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered in combination with gemcitabine, abraxane, erlotinib, geftinib, and/or irinotecan to patients with non-small cell lung cancer.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered in combination with carboplatin and irinotecan to patients with non-small cell lung cancer.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered with doxetaxol to patients with non-small cell lung cancer who have been previously treated with carbo/VP 16 and radiotherapy.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered in combination with carboplatin and/or taxotere, or in combination with carboplatin, paclitaxel and/or thoracic radiotherapy to patients with non-small cell lung cancer.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered in combination with taxotere to patients with stage IIIB or IV non-small cell lung cancer.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered in combination with oblimersen (Genasense®) to patients with small cell lung cancer.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered in combination with ABT-737 (Abbott Laboratories) and/or obatoclax (GX15-070) to patients with lymphoma and other blood cancers.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered alone or in combination with a second active ingredient such as vinblastine or fludarabine to patients with various types of lymphoma, including, but not limited to, Hodgkin's lymphoma, non-Hodgkin's lymphoma, cutaneous T-Cell lymphoma, cutaneous B-Cell lymphoma, diffuse large B-Cell lymphoma or relapsed or refractory low grade follicular lymphoma.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered in combination with taxotere, IL-2, IFN, GM-CSF, PLX4032 (Plexxikon) and/or dacarbazine to patients with various types or stages of melanoma.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered alone or in combination with vinorelbine to patients with malignant mesothelioma, or stage IIIB non-small cell lung cancer with pleural implants or malignant pleural effusion mesothelioma syndrome.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered to patients with various types or stages of multiple myeloma in combination with dexamethasone, zoledronic acid, palmitronate, GM-CSF, biaxin, vinblastine, melphalan, busulphan, cyclophosphamide, IFN, palmidronate, prednisone, bisphosphonate, celecoxib, arsenic trioxide, PEG INTRON-A, vincristine, or a combination thereof.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered to patients with relapsed or refractory multiple myeloma in combination with doxorubicin (Doxil®), vincristine and/or dexamethasone (Decadron®).

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered to patients with various types or stages of ovarian cancer such as peritoneal carcinoma, papillary serous carcinoma, refractory ovarian cancer or recurrent ovarian cancer, in combination with taxol, carboplatin, doxorubicin, gemcitabine, cisplatin, xeloda, paclitaxel, dexamethasone, or a combination thereof.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered to patients with various types or stages of prostate cancer, in combination with xeloda, 5 FU/LV, gemcitabine, irinotecan plus gemcitabine, cyclophosphamide, vincristine, dexamethasone, GM-CSF, celecoxib, taxotere, ganciclovir, paclitaxel, adriamycin, docetaxel, estramustine, Emcyt, denderon or a combination thereof.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered to patients with various types or stages of renal cell cancer, in combination with capecitabine, IFN, tamoxifen, IL-2, GM-CSF, Celebrex®, or a combination thereof.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered to patients with various types or stages of gynecologic, uterus or soft tissue sarcoma cancer in combination with IFN, a COX-2 inhibitor such as Celebrex®, and/or sulindac.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered to patients with various types or stages of solid tumors in combination with celebrex, etoposide, cyclophosphamide, docetaxel, apecitabine, IFN, tamoxifen, IL-2, GM-CSF, or a combination thereof.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered to patients with scleroderma or cutaneous vasculitis in combination with celebrex, etoposide, cyclophosphamide, docetaxel, apecitabine, IFN, tamoxifen, IL-2, GM-CSF, or a combination thereof.

Also encompassed herein is a method of increasing the dosage of an anti-cancer drug or agent that can be safely and effectively administered to a patient, which comprises administering to the patient (e.g., a human) or an enantiomer or a mixture of enantiomers thereof, or a pharmaceutically acceptable salt, solvate, hydrate, co-crystal, clathrate, or polymorph thereof. Patients that can benefit by this method are those likely to suffer from an adverse effect associated with anti-cancer drugs for treating a specific cancer of the skin, subcutaneous tissue, lymph nodes, brain, lung, liver, bone, intestine, colon, heart, pancreas, adrenal, kidney, prostate, breast, colorectal, or combinations thereof. The administration of a compound provided herein, e.g., the compound of Formula I, or an enantiomer or a mixture of enantiomers thereof, or a pharmaceutically acceptable salt, solvate, hydrate, co-crystal, clathrate, or polymorph thereof, alleviates or reduces adverse effects which are of such severity that it would otherwise limit the amount of anti-cancer drug.

In one embodiment, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered orally and daily in an amount ranging from about 0.1 to about 150 mg, from about 1 to about 50 mg, or from about 2 to about 25 mg, prior to, during, or after the occurrence of the adverse effect associated with the administration of an anti-cancer drug to a patient. In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered in combination with specific agents such as heparin, aspirin, coumadin, or G-CSF to avoid adverse effects that are associated with anti-cancer drugs such as but not limited to neutropenia or thrombocytopenia.

In one embodiment, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered to patients with diseases and disorders associated with or characterized by, undesired angiogenesis in combination with additional active ingredients, including, but not limited to, anti-cancer drugs, anti-inflammatories, antihistamines, antibiotics, and steroids.

In another embodiment, encompassed herein is a method of treating, preventing and/or managing cancer, which comprises administering the compound of Formula I, or an enantiomer or a mixture of enantiomers thereof, or a pharmaceutically acceptable salt, solvate, hydrate, co-crystal, clathrate, or polymorph thereof, in conjunction with (e.g. before, during, or after) conventional therapy including, but not limited to, surgery, immunotherapy, biological therapy, radiation therapy, or other non-drug based therapy presently used to treat, prevent or manage cancer. The combined use of the compound provided herein and conventional therapy may provide a unique treatment regimen that is unexpectedly effective in certain patients. Without being limited by theory, it is believed that the compound of Formula I may provide additive or synergistic effects when given concurrently with conventional therapy.

As discussed elsewhere herein, encompassed herein is a method of reducing, treating and/or preventing adverse or undesired effects associated with conventional therapy including, but not limited to, surgery, chemotherapy, radiation therapy, hormonal therapy, biological therapy and immunotherapy. A compound provided herein, e.g., the compound of Formula I, or an enantiomer or a mixture of enantiomers thereof, or a pharmaceutically acceptable salt, solvate, hydrate, co-crystal, clathrate, or polymorph thereof, and other active ingredient can be administered to a patient prior to, during, or after the occurrence of the adverse effect associated with conventional therapy.

In one embodiment, the compound of Formula I can be administered in an amount ranging from about 0.1 to about 150 mg, from about 1 to about 25 mg, or from about 2 to about 10 mg orally and daily alone, or in combination with a second active agent disclosed herein (see, e.g., section 5.4), prior to, during, or after the use of conventional therapy.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, and doxetaxol are administered to patients with non-small cell lung cancer who were previously treated with carbo/VP 16 and radiotherapy.

C-2. Use with Transplantation Therapy

The compound of Formula I, or an enantiomer or a mixture of enantiomers thereof, or a pharmaceutically acceptable salt, solvate, hydrate, co-crystal, clathrate, or polymorph thereof, provided herein can be used to reduce the risk of Graft Versus Host Disease (GVHD). Therefore, encompassed herein is a method of treating, preventing and/or managing cancer, which comprises administering the compound of Formula I, or an enantiomer or a mixture of enantiomers thereof, or a pharmaceutically acceptable salt, solvate, hydrate, co-crystal, clathrate, or polymorph thereof, in conjunction with transplantation therapy.

As those of ordinary skill in the art are aware, the treatment of cancer is often based on the stages and mechanism of the disease. For example, as inevitable leukemic transformation develops in certain stages of cancer, transplantation of peripheral blood stem cells, hematopoietic stem cell preparation or bone marrow may be necessary. The combined use of the compound of Formula I, or an enantiomer or a mixture of enantiomers thereof, or a pharmaceutically acceptable salt, solvate, hydrate, co-crystal, clathrate, or polymorph thereof, provided herein and transplantation therapy provides a unique and unexpected synergism. In particular, the compound of Formula I, or an enantiomer or a mixture of enantiomers thereof, or a pharmaceutically acceptable salt, solvate, hydrate, co-crystal, clathrate, or polymorph thereof, exhibits immunomodulatory activity that may provide additive or synergistic effects when given concurrently with transplantation therapy in patients with cancer.

The compound of Formula I, or an enantiomer or a mixture of enantiomers thereof, or a pharmaceutically acceptable salt, solvate, hydrate, co-crystal, clathrate, or polymorph thereof, can work in combination with transplantation therapy reducing complications associated with the invasive procedure of transplantation and risk of GVHD. Encompassed herein is a method of treating, preventing and/or managing cancer which comprises administering to a patient (e.g., a human) the compound of Formula I, or an enantiomer or a mixture of enantiomers thereof, or a pharmaceutically acceptable salt, solvate, hydrate, co-crystal, clathrate, or polymorph thereof, before, during, or after the transplantation of umbilical cord blood, placental blood, peripheral blood stem cell, hematopoietic stem cell preparation, or bone marrow. Some examples of stem cells suitable for use in the methods provided herein are disclosed in U.S. Pat. No. 7,498,171, the disclosure of which is incorporated herein by reference in its entirety.

In one embodiment, the compound of Formula I, or an enantiomer or a mixture of enantiomers thereof, or a pharmaceutically acceptable salt, solvate, hydrate, co-crystal, clathrate, or polymorph thereof, is administered to patients with multiple myeloma before, during, or after the transplantation of autologous peripheral blood progenitor cell.

In one embodiment, the compound of Formula I, or an enantiomer or a mixture of enantiomers thereof, or a pharmaceutically acceptable salt, solvate, hydrate, co-crystal, clathrate, or polymorph thereof, is administered to patients with NHL (e.g., DLBCL) before, during, or after the transplantation of autologous peripheral blood progenitor cell.

C-3. Cycling Therapy

In certain embodiments, the prophylactic or therapeutic agents provided herein are cyclically administered to a patient. Cycling therapy involves the administration of an active agent for a period of time, followed by a rest for a period of time, and repeating this sequential administration. Cycling therapy can reduce the development of resistance to one or more of the therapies, avoid, or reduce the side effects of one of the therapies, and/or improves the efficacy of the treatment.

Consequently, in certain embodiments, the compound of Formula I, or an enantiomer or a mixture of enantiomers thereof, or a pharmaceutically acceptable salt, solvate, hydrate, co-crystal, clathrate, or polymorph thereof, provided herein is administered daily in a single or divided doses in a four to six week cycle with a rest period of about a week or two weeks. The cycling method further allows the frequency, number, and length of dosing cycles to be increased. Thus, encompassed herein in certain embodiments is the administration of a compound provided herein, e.g., the compound of Formula I, or an enantiomer or a mixture of enantiomers thereof, or a pharmaceutically acceptable salt, solvate, hydrate, co-crystal, clathrate, or polymorph thereof, for more cycles than are typical when it is administered alone. In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered for a greater number of cycles that would typically cause dose-limiting toxicity in a patient to whom a second active ingredient is not also being administered.

In one embodiment, the compound of Formula I, or an enantiomer or a mixture of enantiomers thereof, or a pharmaceutically acceptable salt, solvate, hydrate, co-crystal, clathrate, or polymorph thereof, is administered daily and continuously for three or four weeks at a dose of from about 0.1 to about 150 mg/d followed by a break of one or two weeks.

In another embodiment, the compound of Formula I, or an enantiomer or a mixture of enantiomers thereof, or a pharmaceutically acceptable salt, solvate, hydrate, co-crystal, clathrate, or polymorph thereof, and a second active ingredient are administered orally, with administration of the compound of Formula I occurring 30 to 60 minutes prior to a second active ingredient, during a cycle of four to six weeks. In certain embodiments, the combination of the compound of Formula I, or an enantiomer or a mixture of enantiomers thereof, or a pharmaceutically acceptable salt, solvate, hydrate, co-crystal, clathrate, or polymorph thereof, and a second active ingredient is administered by intravenous infusion over about 90 minutes every cycle. In certain embodiments, one cycle comprises the administration from about 0.1 to about 150 mg/day of the compound of Formula I, or an enantiomer or a mixture of enantiomers thereof, or a pharmaceutically acceptable salt, solvate, hydrate, co-crystal, clathrate, or polymorph thereof, and from about 50 to about 200 $mg/m^2$/day of a second active ingredient daily for three to four weeks and then one or two weeks of rest. In certain embodiments, the number of cycles during which the combinatorial treatment is administered to a patient is ranging from about one to about 24 cycles, from about two to about 16 cycles, or from about four to about three cycles.

D. Patient Population

In certain embodiments of the methods provided herein, the subject is an animal, preferably a mammal, more preferably a non-human primate. In particular embodiments, the subject is a human. The subject can be a male or female subject.

Particularly useful subjects for the methods provided herein include human cancer patients, for example, those who have been diagnosed with leukemia, including acute myeloid leukemia, acute lymphocytic leukemia, chronic myelogenous leukemia, and chronic myelogenous leukemia. In certain embodiments, the subject has not been diagnosed with acute promyelocytic leukemia.

In some embodiments, the subject has a higher than normal blast population. In some embodiments, the subject has a blast population of at least 10%. In some embodiments, the subject has a blast population of between 10 and 15%. In some embodiments, the subject has a blast population of at least 15%. In some embodiments, the subject has a blast population of between 15 and 20%. In some embodiments, the subject has a blast population of at least 20%. In some embodiments, the subject has a blast population of about 10-15%, about 15-20%, or about 20-25%. In other embodiments, the subject has a blast population of less than 10%. In the context of the methods described herein, useful subjects having a blast population of less than 10% includes those subjects that, for any reason according to the judgment of the skilled practitioner in the art, are in need of treatment with a compound provided herein, alone or in combination with a second active agent.

In some embodiments, the subject is treated based on the Eastern Cooperative Oncology Group (ECOG) performance status score of the subject for leukemia. ECOG performance status can be scored on a scale of 0 to 5, with 0 denoting asymptomatic; 1 denoting symptomatic but completely ambulant; 2 denoting symptomatic and <50% in bed during the day; 3 denoting symptomatic and >50% in bed, but not bed bound; 4 denoting bed bound; and 5 denoting death. In some embodiments, the subject has an ECOG performance status score of 0 or 1. In some embodiments, the subject has an ECOG performance status score of 0. In some embodiments, the subject has an ECOG performance status score of 1. In other embodiments, the subject has an ECOG performance status score of 2.

In certain embodiments, the methods provided herein encompass the treatment of subjects who have not been previously treated for leukemia. In some embodiments, the subject has not undergone allogeneic bone marrow transplantation. In some embodiments, the subject has not undergone a stem cell transplantation. In some embodiments, the subject has not received hydroxyurea treatment. In some embodiments, the subject has not been treated with any investigational products for leukemia. In some embodiments, the subject has not been treated with systemic glucocorticoids.

In other embodiments, the methods encompass treating subjects who have been previously treated or are currently being treated for leukemia. For example, the subject may have been previously treated or are currently being treated with a standard treatment regimen for leukemia. The subject may have been treated with any standard leukemia treatment regimen known to the practitioner of skill in the art. In certain embodiments, the subject has been previously treated with at least one induction/reinduction or consolidation AML regimen. In some embodiments, the subject has undergone autologous bone marrow transplantation or stem cell transplantation as part of a consolidation regimen. In some embodiments, the bone marrow or stem cell transplantation occurred at least 3 months prior to treatment according to the methods provided herein. In some embodiments, the subject has undergone hydroxyurea treatment. In some embodiments, the hydroxyurea treatment occurred no later than 24 hours prior to treatment according to the methods provided herein. In some embodiments, the subject has undergone prior induction or consolidation therapy with cytarabine (Ara-C). In some embodiments, the subject has undergone treatment with systemic glucocorticosteroids. In some embodiments, the glucocorticosteroid treatment occurred no later 24 hours prior to treatment according to the methods described herein. In other embodiments, the methods encompass treating subjects who have been previously treated for cancer, but are non-responsive to standard therapies.

Also encompassed are methods of treating subjects having relapsed or refractory leukemia. In some embodiments, the subject has been diagnosed with a relapsed or refractory AML subtype, as defined by the World Health Organization (WHO). Relapsed or refractory disease may be de novo AML or secondary AML, e.g., therapy-related AML (t-AML).

In some embodiments, the methods provided herein are used to treat drug resistant leukemias, such as chronic myelogenous leukemia (CML). Thus, treatment with a compound provided herein could provide an alternative for patients who do not respond to other methods of treatment. In some embodiments, such other methods of treatment encompass treatment with Gleevec® (imatinib mesylate). In some embodiments, provided herein are methods of treatment of Philadelphia chromosome positive chronic myelogenous leukemia (Ph+CML). In some embodiments, provided herein are methods of treatment of Gleevec® (imatinib mesylate) resistant Philadelphia chromosome positive chronic myelogenous leukemia (Ph+CML).

Also encompassed are methods of treating a subject regardless of the subject's age, although some diseases or disorders are more common in certain age groups. In some embodiments, the subject is at least 18 years old. In some embodiments, the subject is more than 18, 25, 35, 40, 45, 50, 55, 60, 65, or 70 years old. In other embodiments, the subject is less than 65 years old. In some embodiments, the subject is less than 18 years old. In some embodiments, the subject is less than 18, 15, 12, 10, 9, 8 or 7 years old.

In some embodiments, the methods may find use in subjects at least 50 years of age, although younger subjects could benefit from the method as well. In other embodiments, the subjects are at least 55, at least 60, at least 65, and at least 70 years of age. In another embodiment, the subjects have adverse cytogenetics. "Adverse cytogenetics" is defined as any nondiploid karyotype, or greater than or equal to 3 chromosomal abnormalities. In another embodiment, the subjects are at least 60 years of age and have adverse cytogenetics. In another embodiment, the subjects are 60-65 years of age and have adverse cytogenetics. In another embodiment, the subjects are 65-70 years of age and have adverse cytogenetics.

In certain embodiments, the subject treated has no history of myocardial infarction within three months of treatment according to the methods provided herein. In some embodiments, the subject has no history of cerebrovascular accident or transient ischemic attack within three months of treatment according to the methods provided herein. In some embodiments, the subject has no suffered no thromboembelic event, including deep vein thrombosis or pulmonary embolus, within 28 days of treatment according to the methods provided herein. In other embodiments, the subject has not experienced or is not experiencing uncontrolled disseminated intravascular coagulation.

Because subjects with cancer have heterogeneous clinical manifestations and varying clinical outcomes, the treatment given to a patient may vary, depending on his/her prognosis. The skilled clinician will be able to readily determine without undue experimentation specific secondary agents, types of surgery, and types of non-drug based standard therapy that can be effectively used to treat an individual subject with cancer.

It will be appreciated that every suitable combination of the compounds provided herein with one or more of the aforementioned compounds and optionally one or more further pharmacologically active substances is contemplated herein.

E. Formulation of Pharmaceutical Compositions

The pharmaceutical compositions provided herein contain therapeutically effective amounts of one or more of compounds provided herein and a pharmaceutically acceptable carrier, diluent or excipient.

The compounds can be formulated into suitable pharmaceutical preparations such as solutions, suspensions, tablets, dispersible tablets, pills, capsules, powders, sustained release formulations or elixirs, for oral administration or in sterile solutions or suspensions for ophthalmic or parenteral administration, as well as transdermal patch preparation and dry powder inhalers. Typically the compounds described above are formulated into pharmaceutical compositions using techniques and procedures well known in the art (see, e.g., Ansel Introduction to Pharmaceutical Dosage Forms, Seventh Edition 1999).

In the compositions, effective concentrations of one or more compounds or pharmaceutically acceptable salts is (are) mixed with a suitable pharmaceutical carrier or vehicle. In certain embodiments, the concentrations of the compounds in the compositions are effective for delivery of an amount, upon administration, that treats, prevents, or ameliorates one or more of the symptoms and/or progression of cancer, including solid tumors and blood borne tumors.

Typically, the compositions are formulated for single dosage administration. To formulate a composition, the weight fraction of compound is dissolved, suspended, dispersed or otherwise mixed in a selected vehicle at an effective concentration such that the treated condition is relieved or ameliorated. Pharmaceutical carriers or vehicles suitable for administration of the compounds provided herein include any such carriers known to those skilled in the art to be suitable for the particular mode of administration.

In addition, the compounds may be formulated as the sole pharmaceutically active ingredient in the composition or may be combined with other active ingredients. Liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as known in the art. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

The active compound is included in the pharmaceutically acceptable carrier in an amount sufficient to exert a therapeutically useful effect in the absence of undesirable side effects on the patient treated. The therapeutically effective concentration may be determined empirically by testing the compounds in in vitro and in vivo systems described herein and then extrapolated therefrom for dosages for humans.

The concentration of active compound in the pharmaceutical composition will depend on absorption, tissue distribution, inactivation and excretion rates of the active compound, the physicochemical characteristics of the compound, the dosage schedule, and amount administered as well as other factors known to those of skill in the art. For example, the amount that is delivered is sufficient to ameliorate one or more of the symptoms of cancer, including solid tumors and blood borne tumors.

In certain embodiments, a therapeutically effective dosage should produce a serum concentration of active ingredient of from about 0.1 ng/mL to about 50-100 µg/mL. In one embodiment, the pharmaceutical compositions provide a dosage of from about 0.001 mg to about 2000 mg of compound per kilogram of body weight per day. Pharmaceutical dosage unit forms are prepared to provide from about 1 mg to about 1000 mg and in certain embodiments, from about 10 to about 500 mg of the essential active ingredient or a combination of essential ingredients per dosage unit form. The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

Thus, effective concentrations or amounts of one or more of the compounds described herein or pharmaceutically acceptable salts thereof are mixed with a suitable pharmaceutical carrier or vehicle for systemic, topical or local administration to form pharmaceutical compositions. Compounds are included in an amount effective for ameliorating one or more symptoms of, or for treating, retarding progression, or preventing. The concentration of active compound in the composition will depend on absorption, tissue distribution, inactivation, excretion rates of the active compound, the dosage schedule, amount administered, particular formulation as well as other factors known to those of skill in the art.

The compositions are intended to be administered by a suitable route, including but not limited to orally, parenterally, rectally, topically and locally. For oral administration, capsules and tablets can be formulated. The compositions are in liquid, semi-liquid or solid form and are formulated in a manner suitable for each route of administration.

Solutions or suspensions used for parenteral, intradermal, subcutaneous, or topical application can include any of the following components: a sterile diluent, such as water for injection, saline solution, fixed oil, polyethylene glycol, glycerine, propylene glycol, dimethyl acetamide or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of tonicity such as sodium chloride or dextrose. Parenteral preparations can be enclosed in ampules, pens, disposable syringes or single or multiple dose vials made of glass, plastic or other suitable material.

In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as TWEEN®, or dissolution in aqueous sodium bicarbonate.

Upon mixing or addition of the compound(s), the resulting mixture may be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil water emulsions containing suitable quantities of the compounds or pharmaceutically acceptable salts thereof. The pharmaceutically therapeutically active compounds and salts thereof are formulated and administered in unit dosage forms or multiple dosage forms. Unit dose forms as used herein refer to physically discrete units suitable for human and animal subjects and packaged individually as is known in the art. Each unit dose contains a predetermined quantity of the therapeutically active compound sufficient to produce the desired therapeutic effect, in association with the required pharmaceutical carrier, vehicle or diluent. Examples of unit dose forms include ampules and syringes and individually packaged tablets or capsules. Unit dose forms may be administered in fractions or multiples thereof. A multiple dose form is a plurality of identical unit dosage forms packaged in a single container to be administered in segregated unit dose form. Examples of multiple dose forms include vials, bottles of tablets or capsules or bottles of pints or gallons. Hence, multiple dose form is a multiple of unit doses which are not segregated in packaging.

Sustained-release preparations can also be prepared. Suitable examples of sustained-release preparations include semipermeable matrices of solid hydrophobic polymers containing the compound provided herein, which matrices are in the form of shaped articles, e.g., films, or microcapsule. Examples of sustained-release matrices include iontophoresis patches, polyesters, hydrogels (for example, poly(2-hydroxyethyl-methacrylate), or poly(vinylalcohol)), polylactides, copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated compound remain in the body for a long time, they may denature or aggregate as a result of exposure to moisture at 370° C., resulting in a loss of biological activity and possible changes in their structure. Rational strategies can be devised for stabilization depending on the mechanism of action involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Dosage forms or compositions containing active ingredient in the range of 0.005% to 100% with the balance made up from non toxic carrier may be prepared. For oral administration, a pharmaceutically acceptable non toxic composition is formed by the incorporation of any of the normally employed excipients, such as, for example pharmaceutical grades of mannitol, lactose, starch, magnesium stearate, talcum, cellulose derivatives, sodium crosscarmellose, glucose, sucrose, magnesium carbonate or sodium saccharin. Such compositions include solutions, suspensions, tablets, capsules, powders and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparation of these compositions are known to those skilled in the art. The contemplated compositions may contain about 0.001% 100% active ingredient, in certain embodiments, about 0.1 85% or about 75-95%.

The active compounds or pharmaceutically acceptable salts may be prepared with carriers that protect the compound against rapid elimination from the body, such as time release formulations or coatings.

The compositions may include other active compounds to obtain desired combinations of properties. The compounds provided herein, or pharmaceutically acceptable salts thereof as described herein, may also be advantageously administered for therapeutic or prophylactic purposes together with another pharmacological agent known in the general art to be of value in treating one or more of the diseases or medical conditions referred to hereinabove, such as diseases related to oxidative stress. It is to be understood that such combination therapy constitutes a further aspect of the compositions and methods of treatment provided herein.

Lactose-free compositions provided herein can contain excipients that are well known in the art and are listed, for example, in the U.S. Pharmocopia (USP) SP (XXI)/NF (XVI). In general, lactose-free compositions contain an active ingredient, a binder/filler, and a lubricant in pharmaceutically compatible and pharmaceutically acceptable amounts.

Exemplary lactose-free dosage forms contain an active ingredient, microcrystalline cellulose, pre-gelatinized starch and magnesium stearate.

Further encompassed are anhydrous pharmaceutical compositions and dosage forms containing a compound provided herein. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, Drug Stability: Principles & Practice, 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment and use of formulations.

Anhydrous pharmaceutical compositions and dosage forms provided herein can be prepared using anhydrous or low moisture containing ingredients and low moisture or low humidity conditions. Pharmaceutical compositions and dosage forms that comprise lactose and at least one active ingredient that comprises a primary or secondary amine are anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e.g., vials), blister packs and strip packs.

E-1. Oral Dosage Forms

Oral pharmaceutical dosage forms are either solid, gel or liquid. The solid dosage forms are tablets, capsules, granules, and bulk powders. Types of oral tablets include compressed, chewable lozenges and tablets which may be enteric coated, sugar coated or film coated. Capsules may be hard or soft gelatin capsules, while granules and powders may be provided in non effervescent or effervescent form with the combination of other ingredients known to those skilled in the art.

In certain embodiments, the formulations are solid dosage forms, such as capsules or tablets. The tablets, pills, capsules, troches and the like can contain any of the following ingredients, or compounds of a similar nature: a binder; a diluent; a disintegrating agent; a lubricant; a glidant; a sweetening agent; and a flavoring agent.

Examples of binders include microcrystalline cellulose, gum tragacanth, glucose solution, acacia mucilage, gelatin solution, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate. If oral administration is desired, the compound could be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action, such as antacids, H2 blockers, and diuretics. The active ingredient is a compound or pharmaceutically acceptable salt thereof as described herein. Higher concentrations, up to about 98% by weight of the active ingredient may be included.

Pharmaceutically acceptable carriers included in tablets are binders, lubricants, diluents, disintegrating agents, coloring agents, flavoring agents, and wetting agents. Enteric coated tablets, because of the enteric coating, resist the action of stomach acid and dissolve or disintegrate in the neutral or alkaline intestines. Sugar coated tablets are compressed tablets to which different layers of pharmaceutically acceptable substances are applied. Film coated tablets are compressed tablets which have been coated with a polymer or other suitable coating. Multiple compressed tablets are compressed tablets made by more than one compression cycle utilizing the pharmaceutically acceptable substances previously mentioned. Coloring agents may also be used in the above dosage forms. Flavoring and sweetening agents are used in compressed tablets, sugar coated, multiple compressed and chewable tablets. Flavoring and sweetening agents are especially useful in the formation of chewable tablets and lozenges.

Liquid oral dosage forms include aqueous solutions, emulsions, suspensions, solutions and/or suspensions reconstituted from non effervescent granules and effervescent preparations reconstituted from effervescent granules. Aqueous solutions include, for example, elixirs and syrups. Emulsions are either oil in-water or water in oil.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two phase system in which one liquid is dispersed in the form of small globules throughout another liquid. Pharmaceutically acceptable carriers used in emulsions are non aqueous liquids, emulsifying agents and preservatives. Suspensions use pharmaceutically acceptable suspending agents and preservatives. Pharmaceutically acceptable substances used in non effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic add, sodium benzoate and alcohol. Examples of non aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Diluents include lactose and sucrose. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic adds include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation.

For a solid dosage form, the solution or suspension, in for example propylene carbonate, vegetable oils or triglycerides, is encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include, but are not limited to, those containing a compound provided herein, a dialkylated mono- or poly-alkylene glycol, including, but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl) acetals of lower alkyl aldehydes such as acetaldehyde diethyl acetal.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

E-2. Injectables, Solutions and Emulsions

Parenteral administration, generally characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. Suitable excipients are, for example, water, saline, dextrose, glycerol or ethanol. In addition, if desired, the pharmaceutical compositions to be administered may also contain minor amounts of non toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins. Implantation of a slow release or sustained release system, such that a constant level of dosage is maintained is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The compound diffuses through the outer polymeric membrane in a release rate controlling step. The percentage of active compound contained in such parenteral compositions is highly dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple dose containers which include phenols or cresols, mercurials, benzyl alcohol, chlorobutanol, methyl and propyl p hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcellulose, hydroxypropyl methylcellulose and polyvinylpyrrolidone. Emulsifying agents include Polysorbate 80 (TWEEN® 80). A sequestering or chelating agent of metal ions include EDTA. Pharmaceutical carriers also include ethyl alcohol, polyethylene glycol and propylene glycol for water miscible vehicles and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the patient or animal as is known in the art.

The unit dose parenteral preparations are packaged in an ampule, a vial or a syringe with a needle. All preparations for parenteral administration must be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. Typically a therapeutically effective dosage is formulated to contain a concentration of at least about 0.1% w/w up to about 90% w/w or more, such as more than 1% w/w of the active compound to the treated tissue(s). The active ingredient may be administered at once, or may be divided into a number of smaller doses to be administered at intervals of time. It is understood that the precise dosage and duration of treatment is a function of the tissue being treated and may be determined empirically using known testing protocols or by extrapolation from in vivo or in vitro test data. It is to be noted that concentrations and dosage values may also vary with the age of the individual treated. It is to be further understood that for any particular subject, specific dosage regimens should be adjusted over time according to the individual need and the professional judgment of the person administering or supervising the administration of the formulations, and that the concentration ranges set forth herein are exemplary only and are not intended to limit the scope or practice of the claimed formulations.

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined.

E-3. Lyophilized Powders

Of interest herein are also lyophilized powders, which can be reconstituted for administration as solutions, emulsions and other mixtures. They may also be reconstituted and formulated as solids or gels.

The sterile, lyophilized powder is prepared by dissolving a compound provided herein, or a pharmaceutically acceptable salt thereof, in a suitable solvent. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose or other suitable agent. The solvent may also contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides the desired formulation. Generally, the resulting solution will be apportioned into vials for lyophilization. Each vial will contain a single dosage (including but not limited to 10-1000 mg or 100-500 mg) or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, about 1-50 mg, about 5-35 mg, or about 9-30 mg of lyophilized powder, is added per mL of sterile water or other suitable carrier. The precise amount depends upon the selected compound. Such amount can be empirically determined.

E-4. Topical Administration

Topical mixtures are prepared as described for the local and systemic administration. The resulting mixture may be a solution, suspension, emulsion or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compounds or pharmaceutically acceptable salts thereof may be formulated as aerosols for topical application, such as by inhalation (see, e.g., U.S. Pat. Nos. 4,044,126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will have diameters of less than 50 microns or less than 10 microns.

The compounds may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered.

These solutions, particularly those intended for ophthalmic use, may be formulated as 0.01%-10% isotonic solutions, pH about 5-7, with appropriate salts.

E-5. Compositions for Other Routes of Administration

Other routes of administration, such as topical application, transdermal patches, and rectal administration are also contemplated herein.

For example, pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin gelatin, carbowax (polyoxyethylene glycol) and appropriate mixtures of mono, di and triglycerides of fatty acids. Combinations of the various bases may be used. Agents to raise the melting point of suppositories include spermaceti and wax. Rectal suppositories may be prepared either by the compressed method or by molding. An exemplary weight of a rectal suppository is about 2 to 3 grams.

Tablets and capsules for rectal administration are manufactured using the same pharmaceutically acceptable substance and by the same methods as for formulations for oral administration.

E-6. Sustained Release Compositions

Active ingredients provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, 5,639,480, 5,733,566, 5,739,108, 5,891,474, 5,922,356, 5,972,891, 5,980,945, 5,993,855, 6,045,830, 6,087,324, 6,113,943, 6,197,350, 6,248,363, 6,264,970, 6,267,981, 6,376,461, 6,419,961, 6,589,548, 6,613,358, 6,699,500 and 6,740,634, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients provided herein.

All controlled-release pharmaceutical products have a common goal of improving drug therapy over that achieved by their non-controlled counterparts. In one embodiment, the use of an optimally designed controlled-release preparation in medical treatment is characterized by a minimum of drug substance being employed to cure or control the condition in a minimum amount of time. In certain embodiments, advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

In certain embodiments, the agent may be administered using intravenous infusion, an implantable osmotic pump, a transdermal patch, liposomes, or other modes of administration. In one embodiment, a pump may be used (see, Sefton, *CRC Crit. Ref Biomed. Eng.* 14:201 (1987); Buchwald et al., *Surgery* 88:507 (1980); Saudek et al., *N. Engl. J. Med.* 321:574 (1989). In another embodiment, polymeric materials can be used. In yet another embodiment, a controlled release system can be placed in proximity of the therapeutic target, i.e., thus requiring only a fraction of the systemic dose (see, e.g., Goodson, Medical Applications of Controlled Release, vol. 2, pp. 115-138 (1984).

In some embodiments, a controlled release device is introduced into a subject in proximity of the site of inappropriate immune activation or a tumor. Other controlled release systems are discussed in the review by Langer (Science 249:1527-1533 (1990). The active ingredient can be dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The active ingredient then diffuses through the outer polymeric membrane in a release rate controlling step. The percentage of active ingredient contained in such parenteral compositions is highly dependent on the specific nature thereof, as well as the needs of the subject.

E-7. Targeted Formulations

The compounds provided herein, or pharmaceutically acceptable salts thereof, may also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874.

In one embodiment, liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as described in U.S. Pat. No. 4,522,811. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

E-8. Articles of Manufacture

The compounds or pharmaceutically acceptable salts can be packaged as articles of manufacture containing packaging material, a compound or pharmaceutically acceptable salt thereof provided herein, which is used for treatment, prevention or amelioration of one or more symptoms or progression of cancer, including solid tumors and blood borne tumors, and a label that indicates that the compound or pharmaceutically acceptable salt thereof is used for treatment, prevention or amelioration of one or more symptoms or progression of cancer, including solid tumors and blood borne tumors.

The articles of manufacture provided herein contain packaging materials. Packaging materials for use in packaging pharmaceutical products are well known to those of skill in the art. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, pens, bottles, and any packaging material suitable for a selected formulation and intended mode of administration and treatment. A wide array of formulations of the compounds and compositions provided herein are contemplated.

F. Preparation of Compounds

The compounds provided herein can be prepared by methods known to one of skill in the art and following procedures similar to those described in the Examples section herein and routine modifications thereof. Exemplary reaction schemes for the preparation of compounds are illustrated below.

General Synthesis Including Schemes

The compounds of the present invention may be synthesized by many methods available to those skilled in the art of organic chemistry (Maffrand, J. P. et al., *Heterocycles*, 16(1):35-37 (1981)). General synthetic schemes for preparing compounds of the present invention are described below.

These schemes are illustrative and are not meant to limit the possible techniques one skilled in the art may use to prepare the compounds disclosed herein. Different methods to prepare the compounds of the present invention will be evident to those skilled in the art. Additionally, the various steps in the synthesis may be performed in an alternate sequence in order to give the desired compound or compounds.

Examples of compounds of the present invention prepared by methods described in the general schemes are given in the intermediates and examples section set out hereinafter. Preparation of homochiral examples may be carried out by techniques known to one skilled in the art. For example, homochiral compounds may be prepared by separation of racemic products by chiral phase preparative HPLC. Alternatively, the example compounds may be prepared by methods known to give enantiomerically enriched products. These include, but are not limited to, the incorporation of chiral auxiliary functionalities into racemic intermediates which serve to control the diastereoselectivity of transformations, providing enantio-enriched products upon cleavage of the chiral auxiliary.

together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being affected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al. (*Protective Groups in Organic Synthesis*, 4th Edition, Wiley-Interscience (2006)).

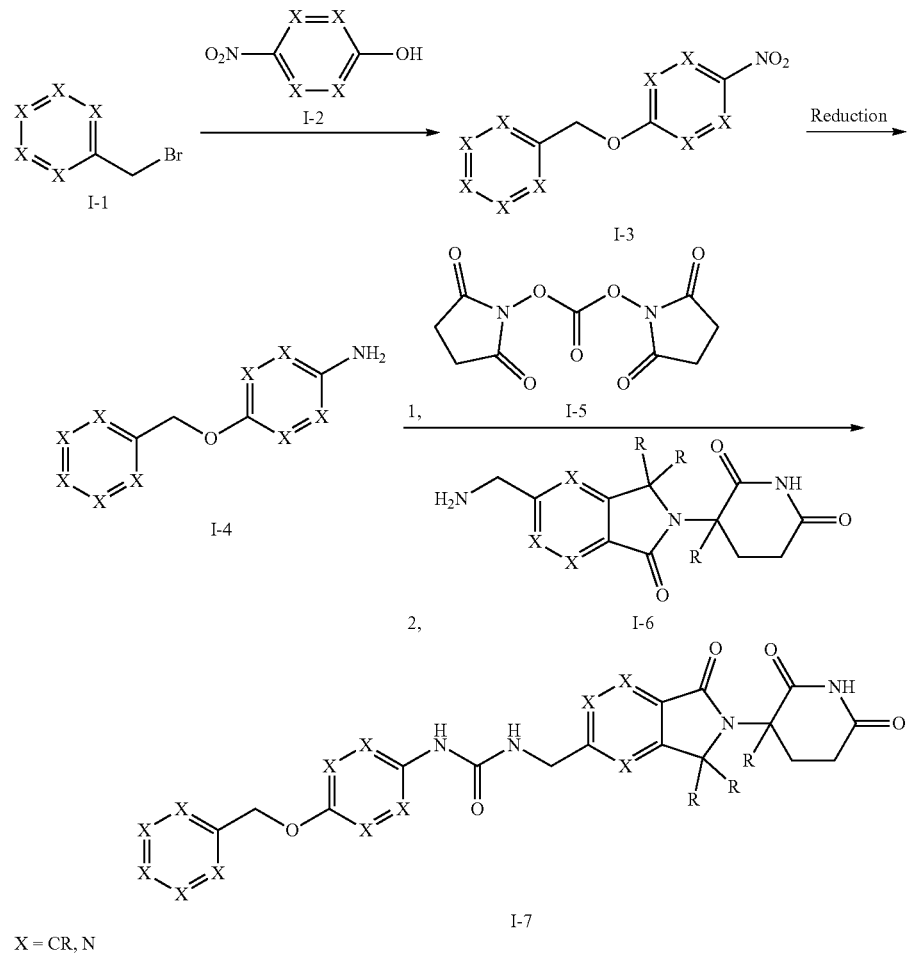

Scheme I. General Synthetic Scheme

X = CR, N

The compounds of the present invention can be prepared in a number of ways known to one skilled in the art of organic synthesis. The compounds of the present invention can be synthesized using the methods described below, Scheme 1 depicts the synthesis of generic compounds I-7. Arylmethyl bromide or heteroarylmethyl bromide I-1 can react with nitrophenol or nitro-heteroaryl alcohol I-2 with base such as potassium carbonate to give compound I-3.

Reduction of the nitro group in I-3 provides aniline I-4, which can react with bis(2,5-dioxopyrrolidin-1-yl) carbonate and then couple with isoindoline methylamine I-6 to generate I-7. The procedures described here can also be used for compounds where the aryl and heteroaryl moieties replaced with 3-12 membered saturated ring systems with some modifications as shown in Examples 32 and 33.

EXAMPLES

Example 1

1-((2-(2,6-dioxopiperidin-3-yl)-1-oxoisoindolin-5-yl)methyl)-3-(4-((4-(hydroxymethyl)benzyl)oxy)phenyl)urea

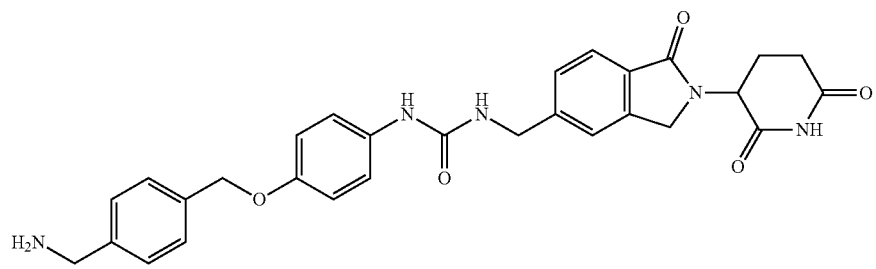

Step 1-1:
(4-((4-nitrophenoxy)methyl)phenyl)methanol

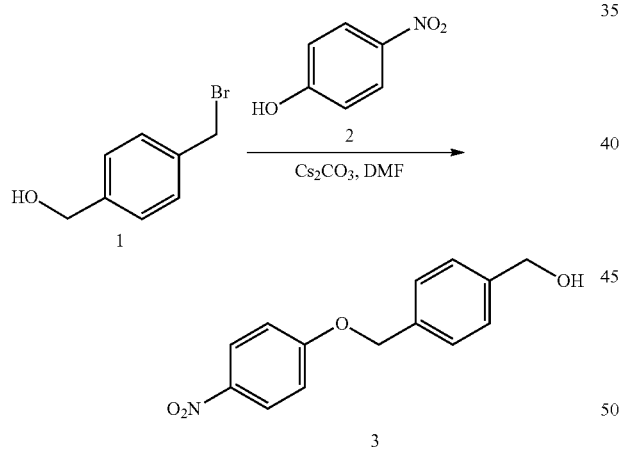

To a solution of (4-(bromomethyl)phenyl)methanol (0.500 g, 2.49 mmol, 1 eq) in DMF (10 mL) were added 4-nitrophenol (0.415 g, 2.98 mmol, 1.2 eq) and cesium carbonate (1.620 g, 4.97 mmol, 2 eq), then the reaction was stirred at 25° C. for 12 h. TLC showed the reaction was completed. The reaction mixture was filtered, and the filtrate was concentrated. It was then diluted with water (20 mL), extracted with ethyl acetate (10 mL×2). The combined organic phase was washed with brine (10 mL×2), dried with anhydrous sodium sulfate, filtered, and concentrated in vacuum. It was used directly into the next step without further purification. (2-((4-Nitrophenoxy)methyl)phenyl)methanol (0.620 g, 2.39 mmol, 96.2% yield) was obtained as a white solid. $^1$H NMR (400 MHz DMSO-$d_6$) δ 8.23-8.17 (m, 2H), 7.45-7.39 (m, 2H), 7.35-7.31 (m, 2H), 7.23-7.17 (m, 2H), 5.24 (s, 2H), 5.18 (t, J=5.6 Hz, 1H), 4.49 (d, J=5.6 Hz, 2H)

Step 1-2: 4-((4-(((tert-butyldimethylsilyl)oxy)methyl)benzyl)oxy)aniline

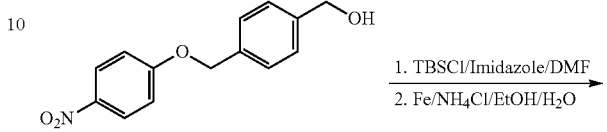

-continued

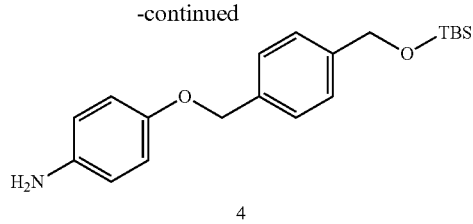

To a solution of (3-((4-nitrophenoxy)methyl)phenyl)methanol (0.620 g, 2.39 mmol, 1 eq) in DMF (15 mL) were added tert-butylchlorodimethylsilane (0.721 g, 4.78 mmol, 2 eq) and 1H-imidazole (0.488 g, 7.17 mmol, 3 eq), then the reaction was stirred at 25° C. for 12 h. TLC showed the reaction was completed. The reaction was dissolved with water (10 mL), extracted with ethyl acetate (10 mL×2). The combined organic phase was washed with brine (10 mL×2), dried with anhydrous sodium sulfate, filtered, and concentrated in vacuum. It was used directly into the next step without further purification. tert-Butyldimethyl((4-((4-nitrophenoxy)methyl)benzyl)oxy)silane (0.800 g, 2.14 mmol, 89.6% yield) was obtained as a white oil.

To a solution of tert-butyldimethyl((4-((4-nitrophenoxy)methyl)benzyl)oxy)silane (0.800 g, 2.14 mmol, 1 eq) in water (5 mL) were added iron (0.598 g, 10.71 mmol, 5 eq), ammonium chloride (1.150 g, 21.42 mmol, 10 eq) and ethanol (10 mL), then the reaction was stirred at 80° C. for 2 h. LCMS showed the reaction was completed. The reaction mixture was filtered, and the filtrate was concentrated. It was when diluted with water (20 mL), extracted with ethyl acetate (10 mL×2). The combined organic phase was washed with brine (10 mL×2), dried with anhydrous sodium sulfate, filtered, and concentrated in vacuum. The reaction was purified by silica gel column chromatography (2-10% Ethyl acetate in Petroleum ether). 4-((4-(((tert-butyldimethylsilyl)oxy)methyl)benzyl)oxy)aniline (0.500 g, 1.46 mmol, 68.0% yield) was obtained as a yellow solid.

Step 1-3: 1-(4-((4-(((tert-butyldimethylsilyl)oxy)methyl)benzyl)oxy)phenyl)-3-((2-(2,6-dioxopiperidin-3-yl)-1-oxoisoindolin-5-yl)methyl)

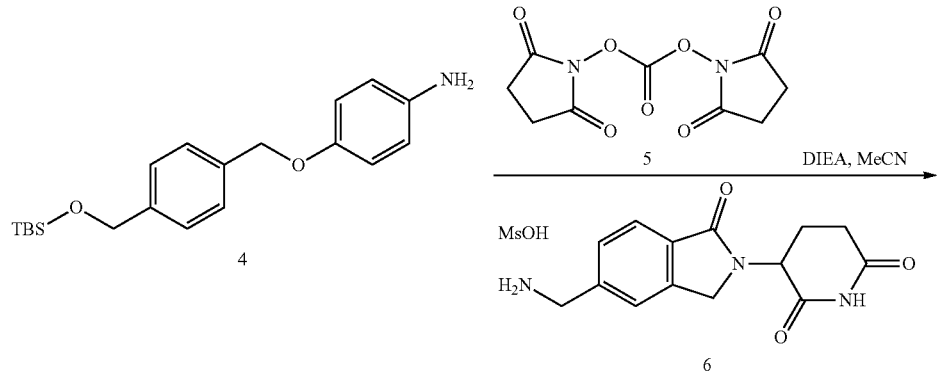

To a solution of 4-((4-(((tert-butyldimethylsilyl)oxy)methyl)benzyl)oxy)aniline (0.209 g, 0.61 mmol, 1.5 eq) and bis(2,5-dioxopyrrolidin-1-yl) carbonate (0.156 g, 0.61 mmol, 1.5 eq) in acetonitrile (3 mL) was added N-ethyl-N-isopropylpropan-2-amine (0.105 g, 0.81 mmol, 2 eq), after stirred at 0° C. for 0.1 h, 3-(5-(aminomethyl)-1-oxoisoindolin-2-yl)piperidine-2,6-dione methanesulfonate (0.150 g, 0.41 mmol, 1 eq, mesylate) was added to the reaction and it was stirred at 25° C. for 11.9 h. LCMS showed the reaction was completed. The reaction mixture was filtered, and the residue was concentrated. It was used directly into the next step without further purification. 1-(4-((4-(((tert-butyldimethylsilyl)oxy)methyl)benzyl)oxy)phenyl)-3-((2-(2,6-dioxopiperidin-3-yl)-1-oxoisoindolin-5-yl)methyl)urea (0.200 g, 0.31 mmol, 76.6% yield) was obtained as a white solid. LCMS (ESI) m/z: 643.2 [M+1]$^+$, $^1$H NMR (400 MHz DMSO-$d_6$) δ 10.98 (s, 1H), 8.47 (s, 2H), 7.69 (d, J=7.6 Hz, 1H), 7.52 (s, 1H), 7.35-7.27 (m, 6H), 6.89 (d, J=8.8 Hz, 3H), 6.72-6.69 (m, 1H), 5.17-5.08 (m, 2H), 5.02 (s, 3H), 4.71 (s, 2H), 4.52-4.30 (m, 7H), 2.90 (d, J=12.0 Hz, 1H), 2.62 (s, 1H), 2.39 (dd, J=4.4, 13.2 Hz, 1H), 2.02-1.98 (m, 1H), 0.95-0.94 (m, 1H), 0.91 (s, 8H), 0.09 (s, 6H)

Step 1-4: 1-((2-(2,6-dioxopiperidin-3-yl)-1-oxoisoindolin-5-yl)methyl)-3-(4-((4-(hydroxymethyl)benzyl)oxy)phenyl)urea

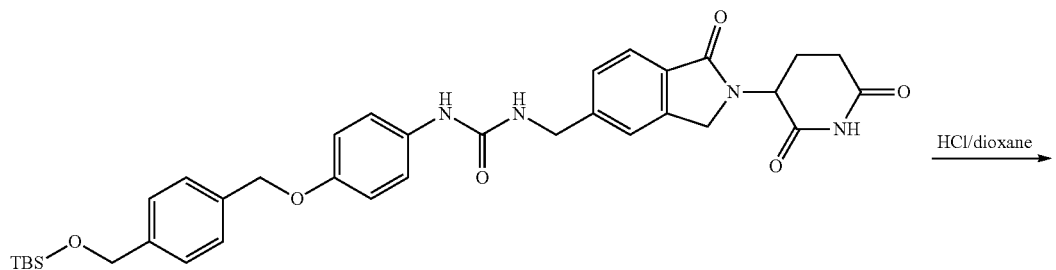

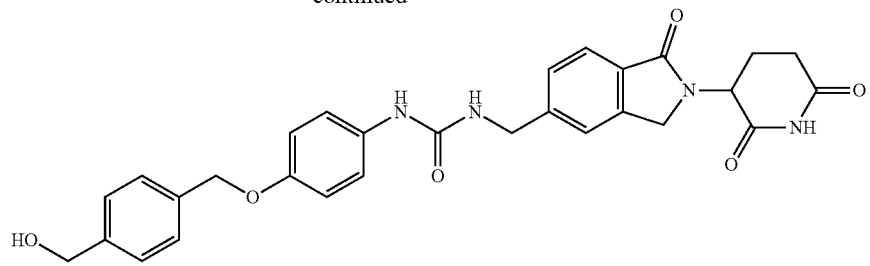

EX. 1

A mixture of 1-(4-((3-((((tert-butyldimethylsilyl)oxy)methyl)benzyl)oxy)phenyl)-3-((2-(2,6-dioxopiperidin-3-yl)-1-oxoisoindolin-5-yl)methyl)urea (0.150 g, 0.23 mmol, 1 eq) in hydrogen chloride/dioxane (3 mL, 4M) was stirred at 25° C. for 1 h. LCMS showed the reaction was completed. The reaction mixture was concentrated under reduced pressure. The reaction was purified by semi-preparative reverse phase HPLC (25-55% acetonitrile+0.225% formic acid in water, over 10 min), then the collected fraction was concentrated to remove most of the acetonitrile, and it was lyophilized to afford the desired compound. 1-((2-(2,6-Dioxopiperidin-3-yl)-1-oxoisoindolin-5-yl)methyl)-3-(4-((3-(hydroxymethyl)benzyl)oxy)phenyl)urea (0.012 g, 0.02 mmol, 9.2% yield, 96.0% purity) was obtained as a white solid. LCMS (ESI) m/z: 529.2 [M+1]$^+$, $^1$H NMR (400 MHz DMSO-d$_6$) δ 10.97 (s, 1H), 8.41 (s, 1H), 7.69 (d, J=7.6 Hz, 1H), 7.51 (s, 1H), 7.43 (d, J=8.0 Hz, 1H), 7.39-7.34 (m, 2H), 7.33-7.26 (m, 4H), 6.88 (d, J=8.8 Hz, 2H), 6.62 (t, J=5.6 Hz, 1H), 5.19-5.07 (m, 2H), 5.01 (s, 2H), 4.52-4.28 (m, 6H), 2.97-2.85 (m, 1H), 2.60 (d, J=16.0 Hz, 1H), 2.41-2.31 (m, 1H), 2.07-1.94 (m, 1H)

Example 2

1-[4-[[4-(aminomethyl)phenyl]methoxy]phenyl]-3-[[2-(2,6-dioxo-3-piperidyl)-1-oxo-isoindolin-5-yl]methyl]urea Step 2-1: tert-butyl N-[[4-[(4-nitrophenoxy)methyl]phenyl]methyl]carbamate

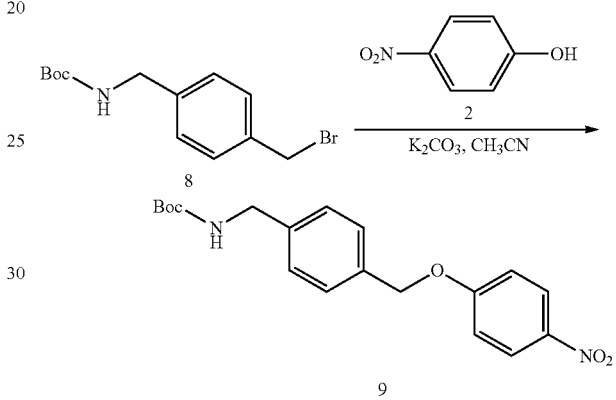

To a solution of tert-butyl N-[[4-(bromomethyl)phenyl]methyl]carbamate (10 g, 33.3 mmol) in MeCN (150 mL) was added 4-nitrophenol (4.82 g, 34.6 mmol) and K$_2$CO$_3$ (13.8 g, 100 mmol). The reaction mixture was stirred at 80° C. for 16 h. TLC (petroleum ether/ethyl acetate, 2:1, Rf$_{\#1}$=0.76 Rf$_{\#2}$=0.6) showed the starting material was consumed and main a new spot formed. The reaction mixture was cooled to r.t and concentrated. The residue was diluted with ethyl acetate/H$_2$O (200 mL/200 mL), the organic layer was washed with brine (250 mL), dried over anhydrous Na$_2$SO$_4$, filtered, and concentrated to give tert-butyl N-[[4-[(4-nitrophenoxy)methyl]phenyl]methyl]carbamate (12 g, crude) as a light yellow solid. $^1$H NMR: (400 MHz, DMSO-d$_6$) δ 8.27 (d, J=9.2 Hz, 2H), 7.48 (d, J=7.6 Hz, 3H), 7.34-7.27 (m, 4H), 5.30 (s, 2H), 4.19 (d, J=6.0 Hz, 1H), 1.45 (s, 9H).

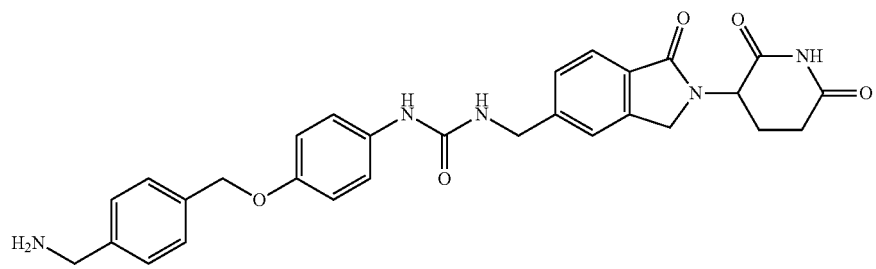 [SMILES: NCc1ccc(COc2ccc(NC(=O)NCc3ccc4c(c3)CN(C3CCC(=O)NC3=O)C4=O)cc2)cc1]

Step 2-2: tert-butyl N-[[4-[(4-aminophenoxy)methyl]phenyl]methyl]carbamate

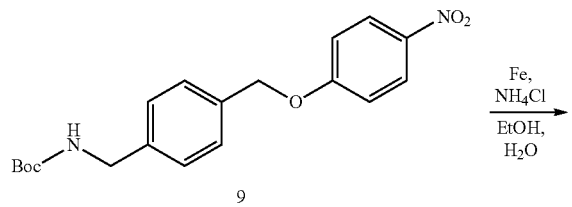

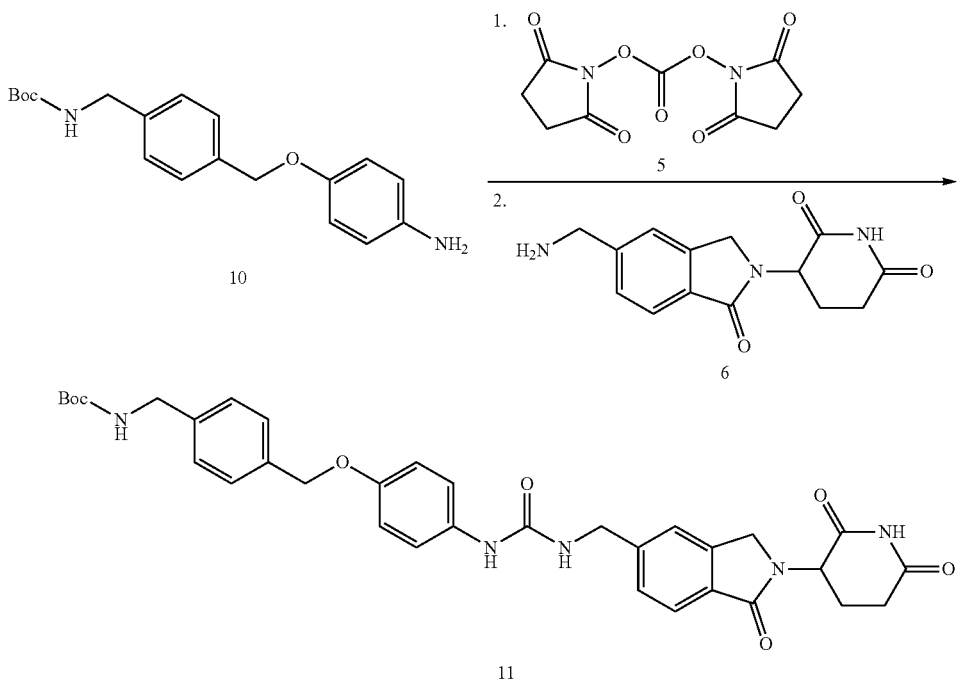

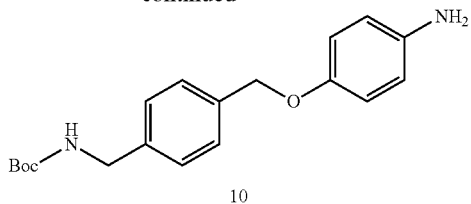

To a solution of tert-butyl N-[[4-[(4-nitrophenoxy)methyl]phenyl]methyl]carbamate (12 g, 33.5 mmol) in EtOH (150 mL) and H₂O (30 mL) was added Fe powder (9.35 g, 167 mmol) and NH₄Cl (17.9 g, 335 mmol). The mixture was stirred at 80° C. for 2 h. TLC (2:1 petroleum ether/ethyl acetate) showed the reaction was finished. The reaction mixture was cooled to rt and filtered. The cake was washed with ethyl acetate (400 mL), the combined filtrate was concentrated. The residue was diluted with water and ethyl acetate (400 mL/400 mL), the organic layer was washed with brine (400 mL), dried over anhydrous Na₂SO₄, filtrated and concentrated to give tert-butyl N-[[4-[(4-aminophenoxy)methyl]phenyl]methyl]carbamate (9 g, 81.9% yield) as a gray solid. This material was used in the next step without further purification.

Step 2-3: tert-butyl N-[[4-[[4-[[2-(2,6-dioxo-3-piperidyl)-1-oxo-isoindolin-5-yl]methyl carbamoylamino]phenoxy]methyl]phenyl]methyl]carbamate To a solution of tert-butyl N-[[4-[(4-aminophenoxy)methyl]phenyl]methyl]carbamate (5.65 g, 17.2 mmol) in MeCN (200 mL) was added bis(2,5-dioxopyrrolidin-1-yl)carbonate (5.64 g, 22.0 mmol) and Et₃N (6.16 g, 60.9 mmol) at −20° C. under nitrogen. The mixture was stirred at −20° C. for 1 h. 3-[5-(Aminomethyl)-1-oxo-isoindolin-2-yl]piperidine-2,6-dione (6.80 g, 18.4 mmol, MsOH salt) was added to the mixture. The mixture was stirred at 20° C. for 15 h. TLC (2:1 petroleum ether/ethyl acetate) showed the reaction was finished. The reaction mixture was filtered, the cake was washed with MeCN (50 mL) and dried to give tert-butyl N-[[4-[[4-[[2-(2,6-dioxo-3-piperidyl)-1-oxo-isoindolin-5-yl]methyl carbamoylamino]phenoxy]methyl]phenyl]methyl]carbamate (9 g, crude) as a gray solid. ¹H NMR: (400 MHz, DMSO-d₆) δ 10.99 (s, 1H), 8.43 (s, 1H), 7.69 (d, J=8.0 Hz, 1H), 7.53-7.23 (m, 9H), 6.88 (d, J=8.8 Hz, 2H), 6.63 (d, J=6.0 Hz, 1H), 5.14-5.09 (m, 1H), 5.09 (s, 2H), 4.47-4.29 (m, 4H), 4.12 (d, J=6.0 Hz, 2H), 2.92-2.91 (m, 1H), 2.62-2.51 (m, 1H), 2.41-2.37 (m, 1H), 1.40 (s, 9H).

Step 2-4: 1-[4-[[4-(aminomethyl)phenyl]methoxy]phenyl]-3-[[2-(2,6-dioxo-3-piperidyl)-1-oxo-isoindolin-5-yl]methyl]urea

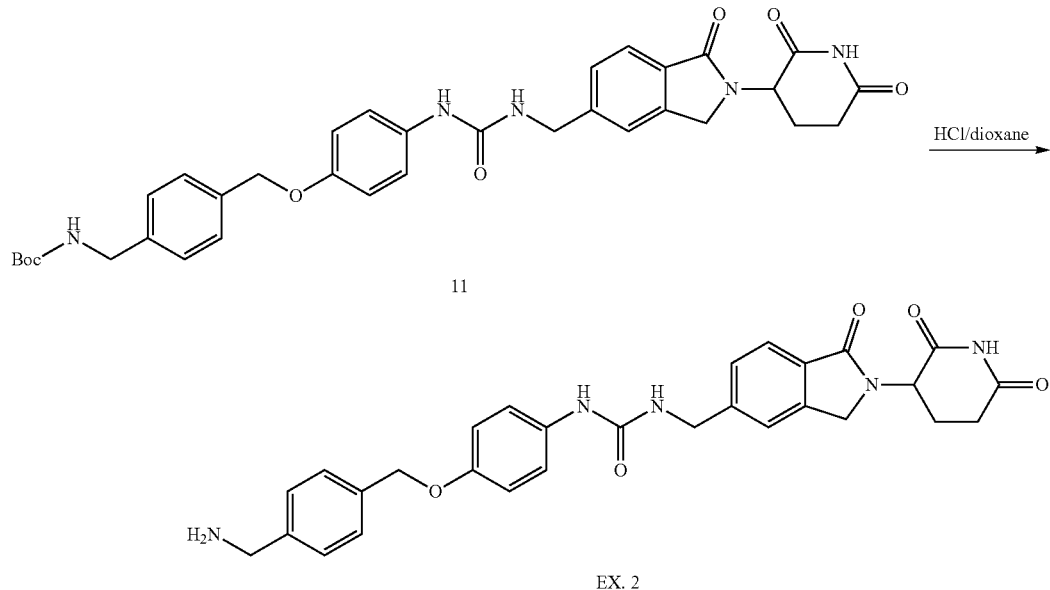 [SMILES: CC(C)(C)OC(=O)NCc1ccc(COc2ccc(NC(=O)NCc3ccc4c(c3)CN(C3CCC(=O)NC3=O)C4=O)cc2)cc1 ; NCc1ccc(COc2ccc(NC(=O)NCc3ccc4c(c3)CN(C3CCC(=O)NC3=O)C4=O)cc2)cc1]

EX. 2

A solution of tert-butyl N-[[4-[[4-[[2-(2,6-dioxo-3-piperidyl)-1-oxo-isoindolin-5-yl]methyl carbamoylamino]phenoxy]methyl]phenyl]methyl]carbamate (9.0 g, 14.3 mmol) and HCl (30 mL, 12 N in dioxane) was stirred at 0° C. for 1 h. LCMS showed the staring material was consumed. MeCN (500 mL) was added into the mixture slowly at 0-10° C. After stirring for 30 minutes, the resulting solid was filtered and dried to give 1-[4-[[4-(aminomethyl)phenyl]methoxy]phenyl]-3-[[2-(2,6-dioxo-3-piperidyl)-1-oxo-isoindolin-5-yl]methyl]urea (7.12 g, 88.0% yield, HC salt) as an off-white solid. $^1$H NMR: (400 MHz, DMSO-$d_6$) δ 10.98 (s, 1H), 8.66 (s, 1H), 9.30 (s, 3H), 7.69 (d, J=7.6 Hz, 1H), 7.51-7.43 (m, 6H), 7.31-7.29 (m, 2H), 6.89 (d, J=2.0 Hz, 2H), 6.88 (s, 1H), 5.13-5.07 (m, 3H), 4.47-4.29 (m, 4H), 4.01 (t, J=5.6 Hz, 2H), 2.95-2.87 (m, 1H), 2.62-2.52 (m, 1H), 2.50-2.38 (m, 1H), 2.01-1.94 (m, 1H).

The examples listed in Table 1 were prepared by following similar procedures to those described in Example 1 and Example 2 from the appropriate commercially available starting materials.

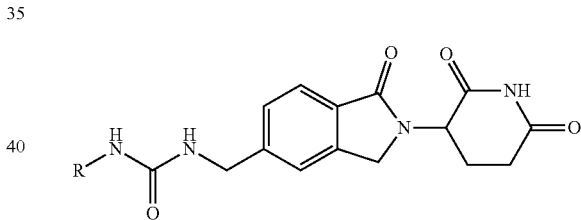

TABLE 1

| Ex# | Name | R | LCMS (M + H)+ | $^1$H NMR (δ ppm) (400 MHz, DMSO-$d_6$) |
|---|---|---|---|---|
| 3 | 1-(4-((2-(aminomethyl)benzyl)oxy)phenyl)-3-((2-(2,6-dioxopiperidin-3-yl)-1-oxoisoindolin-5-yl)methyl)urea | (H2N-benzyl-CH2-O-phenyl) | 528.3 | 10.99 (s, 1 H), 8.75 (s, 1 H), 8.35 (s, 3 H), 7.70 (d, J = 7.6 Hz, 1 H), 7.51-7.60 (m, 3 H), 7.40-7.49 (m, 3 H), 7.35 (d, J = 9.2 Hz, 2 H), 6.97 (d, J = 9.2 Hz, 2 H), 6.87 (s, 1H), 5.17 (s, 2 H), 5.11 (m Hz, 1 H), 4.26-4.52 (m, 4 H), 4.12 (d, J = 5.6 Hz, 2 H), 2.85-3.00 (m, 1 H), 2.57-2.69 (m, 1 H), 2.26-2.42 (m, 1 H), 1.96-2.08 (m, 1 H) |
| 4 | 1-(4-((3-(aminomethyl)benzyl)oxy)phenyl)-3-((2-(2,6-dioxopiperidin-3-yl)-1-oxoisoindolin-5-yl)methyl)urea | (H2N-benzyl-CH2-O-phenyl) | 528.1 | 10.97 (s, 1 H), 8.68 (s, 1 H), 8.32 (s, 3 H), 7.68 (d, J = 7.6 Hz, 1 H), 7.56 (s, 1 H), 7.51 (s, 1 H), 7.42-7.47 (m, 4 H), 7.29-7.34 (m, 2 H), 6.90 (d, J = 9.2 Hz, 2 H), 6.82 (t, J = 6.2 Hz, 1 H), 5.00-5.17 (m, 3 H), 4.28-4.50 (m, 4 H), 4.04 (s, 2 H), 2.82-3.01 (m, 1 H), 2.54-2.63 (m, 1 H), 2.29-2.43 (m, 1 H), 1.93-2.07 (m, 1 H) |

TABLE 1-continued

| Ex# | Name | R | LCMS (M + H)+ | ¹H NMR (δ ppm) (400 MHz, DMSO-d₆) |
|---|---|---|---|---|
| 5 | 1-(4-((3-aminobenzyl)oxy)phenyl)-3-((2-(2,6-dioxopiperidin-3-yl)-1-oxoisoindolin-5-yl)methyl)urea | | 514.2 | 10.97 (s, 1H), 8.55 (s, 1H), 7.69 (d, J = 8.0 Hz, 1H), 7.51 (s, 1H), 7.46-7.37 (m, 2H), 7.33-7.22 (m, 4H), 7.13 (s, 1H), 6.89 (d, J = 9.2 Hz, 2H), 6.73 (s, 1H), 5.10 (dd, J = 5.2, 13.6 Hz, 1H), 5.05 (s, 2H), 4.48-4.38 (m, 3H), 4.34-4.27 (m, 1H), 2.96-2.86 (m, 1H), 2.69-2.52 (m, 2H), 2.38 (dq, J = 4.8, 13.2 Hz, 2H), 1.95-2.04 (m, 1H) |
| 6 | 1-[4-(benzyloxy)phenyl]-3-{[2-(2,6-dioxopiperidin-3-yl)-1-oxo-2,3-dihydro-1H-isoindol-5-yl]methyl}urea | | 499.1 | 10.98 (s, 1H), 8.43 (s, 1H), 7.69 (d, J = 7.6 Hz, 1H), 7.51-7.43 (m, 6H), 7.31-7.29 (m, 2H), 6.89 (d, J = 2.0 Hz, 2H), 6.63 (m, 1H), 5.14-5.09 (m, 3H), 4.28-4.48 (m, 4H), 2.95-2.87 (m, 1H), 2.62-2.52 (m, 1H), 2.50-2.38 (m, 1H), 2.01-1.94 (m, 1H). |
| 7 | 1-((2-(2,6-dioxopiperidin-3-yl)-1-oxoisoindolin-5-yl)methyl)-3-(4-((3-(hydroxymethyl)benzyl)oxy)phenyl)urea | | 529.2 | 10.96 (s, 1H), 8.44 (s, 1H), 7.68 (d, J = 7.6 Hz, 1H), 7.50 (s, 1H), 7.43 (d, J = 7.6 Hz, 1H), 7.38 (s, 1H), 7.34-7.21 (m, 5H), 6.89 (d, J = 9.2 Hz, 2H), 6.64 (t, J = 5.6 Hz, 1H), 5.18 (t, J = 5.6 Hz, 1H), 5.10 (dd, J = 5.2, 13.2 Hz, 1H), 5.02 (s, 2H), 4.53-4.28 (m, 6H), 2.96-2.85 (m, 1H), 2.59 (d, J = 18.0 Hz, 1H), 2.38 (dd, J = 4.4, 13.2 Hz, 1H), 2.04-1.94 (m, 1H) |
| 8 | 1-((2-(2,6-dioxopiperidin-3-yl)-1-oxoisoindolin-5-yl)methyl)-3-(4-((2-(hydroxymethyl)benzyl)oxy)phenyl)urea | | 529.3 | 10.97 (s, 1H), 8.47 (s, 1H), 7.69 (d, J = 7.6 Hz, 1H), 7.52 (s, 1H), 7.48-7.40 (m, 3H), 7.35-7.29 (m, 3H), 7.28-7.22 (m, 1H), 6.91 (d, J = 8.8 Hz, 2H), 6.66 (t, J = 6.0 Hz, 1H), 5.20-5.06 (m, 4H), 4.60 (s, 2H), 4.49-4.27 (m, 4H), 2.96-2.86 (m, 1H), 2.60 (d, J = 16.4 Hz, 1H), 2.44-2.33 (m, 1H), 2.05-1.96 (m, 1H) |
| 9 | 1-((2-(2,6-dioxopiperidin-3-yl)-1-oxoisoindolin-5-yl)methyl)-3-(4-((2-hydroxybenzyl)oxy)phenyl)urea | | 515.1 | 10.99 (s, 1H), 9.45 (s, 1H), 8.50 (s, 1H), 7.69 (d, J = 7.6 Hz, 1H), 7.51 (s, 1H), 7.43 (d, J = 7.6 Hz, 1H), 7.30 (d, J = 9.2 Hz, 2H), 7.18-7.11 (m, 1H), 6.91-6.78 (m, 4H), 6.74-6.66 (m, 2H), 5.11 (dd, J = 5.2, 13.2 Hz, 1H), 4.95 (s, 2H), 4.48-4.26 (m, 4H), 2.96-2.86 (m, 1H), 2.63-2.57 (m, 1H), 2.44-2.35 (m, 1H), 2.03-1.95 (m, 1H) |
| 10 | 1-((2-(2,6-dioxopiperidin-3-yl)-1-oxoisoindolin-5-yl)methyl)-3-(4-((2-hydroxybenzyl)oxy)phenyl)urea | | 497.1 (M − 18 + 1) | 10.97 (br s, 1H), 8.80-8.60 (m, 1H), 7.69 (d, J = 7.8 Hz, 1H), 7.55-7.49 (m, 2H), 7.44 (d, J = 7.6 Hz, 1H), 7.40 (d, J = 9.2 Hz, 2H), 7.24-7.17 (m, 1H), 7.14-7.08 (m, 1H), 6.85 (d, J = 8.8 Hz, 3H), 6.73 (d, J = 7.6 Hz, 1H), 5.15-5.06 (m, 2H), 4.54 (d, J = 5.2 Hz, 2H), 4.48-4.38 (m, 3H), 4.35-4.27 (m, 1H), 2.97-2.85 (m, 1H), 2.63-2.58 (m, 1H), 2.38 (br dd, J = 4.4, 13.2 Hz, 1H), 2.04-1.95 (m, 1H) |

TABLE 1-continued

| Ex# | Name | R | LCMS (M + H)+ | 1H NMR (δ ppm) (400 MHz, DMSO-d6) |
|---|---|---|---|---|
| 11 | 1-(4-{[4-(aminomethyl)-2-fluorophenyl]methoxy}phenyl)-3-{[2-(2,6-dioxopiperidin-3-yl)-1-oxo-2,3-dihydro-1H-isoindol-5-yl]methyl}urea | | 546.1 | 10.99 (s, 1H), 8.52 (s, 1H), 8.20 (s, 3H), 7.69 (d, J = 7.8 Hz, 1H), 7.58 (t, J = 7.8 Hz, 1H), 7.51 (s, 1H), 7.47-7.40 (m, 1H), 7.36 (dd, J = 11.0, 1.6 Hz, 1H), 7.30 (td, J = 6.1, 5.6, 3.4 Hz, 3H), 6.95-6.86 (m, 2H), 6.74 (t, J = 6.1 Hz, 1H), 5.09 (s, 3H), 4.45-4.40 (m, J = 6.0 Hz, 3H), 4.31 (d, J = 17.3 Hz, 1H), 4.07 (s, 2H), 2.92 (ddd, J = 17.2, 13.6, 5.4 Hz, 1H), 2.59 (dd, J = 17.4, 3.6 Hz, 1H), 2.40 (td, J = 13.2, 4.5 Hz, 1H), 2.00 (ddq, J = 10.4, 5.4, 3.1, 2.6 Hz, 1H) |
| 12 | 1-(4-{[4-(aminomethyl)-2-methylphenyl]methoxy}phenyl)-3-{[2-(2,6-dioxopiperidin-3-yl)-1-oxo-2,3-dihydro-1H-isoindol-5-yl]methyl}urea | | 542.1 | 7.77 (d, J = 7.9 Hz, 1H), 7.58-7.43 (m, 3H), 7.33-7.22 (m, 4H), 6.92 (d, J = 8.9 Hz, 2H), 5.15 (dd, J = 13.4, 5.3 Hz, 1H), 5.07 (s, 2H), 4.58-4.39 (m, 4H), 4.08 (s, 2H), 2.88 (dd, J = 13.2, 5.2 Hz, 1H), 2.80 (s, 1H), 2.49 (dd, J = 13.0, 4.8 Hz, 1H), 2.41 (s, 3H), 2.17 (m, 1H) |
| 13 | 1-(4-{[5-(aminomethyl)pyridin-2-yl]methoxy}phenyl)-3-{[2-(2,6-dioxopiperidin-3-yl)-1-oxo-2,3-dihydro-1H-isoindol-5-yl]methyl}urea | | 529.2 | 10.99 (s, 1H), 8.63 (d, J = 2.3 Hz, 1H), 8.52 (d, J = 12.5 Hz, 1H), 8.19 (s, 3H), 7.90 (dd, J = 8.1, 2.3 Hz, 1H), 7.69 (d, J = 7.8 Hz, 1H), 7.56 (d, J = 8.0 Hz, 1H), 7.50 (s, 1H), 7.43 (dd, J = 7.8, 1.4 Hz, 1H), 7.35-7.26 (m, 2H), 6.95-6.86 (m, 2H), 6.72 (d, J = 6.0 Hz, 1H), 5.14-5.11 (m, J = 13.2, 5.0 Hz, 3H), 4.49-4.36 (m, 3H), 4.30 (d, J = 17.3 Hz, 1H), 4.09 (q, J = 5.8 Hz, 2H), 2.91 (ddd, J = 17.2, 13.6, 5.4 Hz, 1H), 2.60 (d, J = 17.8 Hz, 1H), 2.46-2.33 (m, 1H), 2.00 (ddq, J = 10.5, 5.4, 3.3, 2.7 Hz, 1H). |
| 14 | 1-(4-{[6-(aminomethyl)pyridin-3-yl]methoxy}phenyl)-3-{[2-(2,6-dioxopiperidin-3-yl)-1-oxo-2,3-dihydro-1H-isoindol-5-yl]methyl}urea | | 529.3 | 11.00 (s, 1H), 8.69 (d, J = 2.1 Hz, 1H), 8.55 (s, 1H), 8.28 (s, 3H), 7.93 (dd, J = 8.1, 2.2 Hz, 1H), 7.69 (d, J = 7.8 Hz, 1H), 7.49 (d, J = 8.4 Hz, 2H), 7.43 (dd, J = 7.8, 1.4 Hz, 1H), 7.36-7.24 (m, 2H), 6.97-6.87 (m, 2H), 6.76 (t, J = 6.0 Hz, 1H), 5.12 (d, J = 13.5 Hz, 3H), 4.44-4.39 (dd, J = 5.9 Hz, 3H), 4.30 (d, J = 17.3 Hz, 1H), 4.21 (q, J = 5.9 Hz, 2H), 2.92 (ddd, J = 17.3, 13.6, 5.4 Hz, 1H), 2.65-2.51 (d, 1H), 2.46-2.32 (m, 1H), 2.00 (ddq, J = 10.6, 5.5, 3.3, 2.7 Hz, 1H) |
| 15 | 1-(4-{[5-(aminomethyl)pyrimidin-2-yl]methoxy}phenyl)-3-{[2-(2,6-dioxopiperidin-3-yl)-1-oxo-2,3-dihydro-1H-isoindol-5-yl]methyl}urea | | 530.1 | 8.89 (s, 2H), 7.76 (d, J = 7.9 Hz, 1H), 7.54 (s, 1H), 7.48 (d, J = 7.9 Hz, 1H), 7.29-7.21 (m, 2H), 6.96-6.88 (m, 2H), 5.29 (s, 2H), 5.14 (dd, J = 13.3, 5.2 Hz, 1H), 4.55-4.40 (m, 4H), 4.23 (s, 2H), 3.68 (s, 1H), 2.90 (ddd, J = 18.6, 13.5, 5.4 Hz, 1H), 2.77 (ddd, J = 17.6, 4.6, 2.4 Hz, 1H), 2.48 (qd, J = 13.3, 4.7 Hz, 1H), 2.17 (ddd, J = 9.9, 5.3, 2.7 Hz, 1H) |

TABLE 1-continued

| Ex# | Name | R | LCMS (M + H)+ | 1H NMR (δ ppm) (400 MHz, DMSO-d6) |
|---|---|---|---|---|
| 16 | 1-(4-{[6-(aminomethyl)pyridazin-3-yl]methoxy}phenyl)-3-{[2-(2,6-dioxopiperidin-3-yl)-1-oxo-2,3-dihydro-1H-isoindol-5-yl]methyl}urea | | 530.1 | 7.93 (d, J = 8.7 Hz, 1H), 7.77 (dd, J = 8.3, 7.1 Hz, 2H), 7.54 (s, 1H), 7.52-7.45 (m, 1H), 7.39-7.24 (m, 2H), 7.01-6.92 (m, 2H), 5.40 (s, 2H), 5.14 (dd, J = 13.3, 5.2 Hz, 1H), 4.48 (d, J = 14.7 Hz, 6H), 2.90 (ddd, J = 17.6, 13.5, 5.4 Hz, 1H), 2.77 (ddd, J = 17.6, 4.7, 2.5 Hz, 1H), 2.48 (qd, J = 13.2, 4.7 Hz, 1H), 2.16 (dtd, J = 12.7, 5.3, 2.4 Hz, 1H) |
| 17 | 1-(4-{[4-(aminomethyl)phenyl]methoxy}-3-methylphenyl)-3-{[2-(2,6-dioxopiperidin-3-yl)-1-oxo-2,3-dihydro-1H-isoindol-5-yl]methyl}urea | | 542.2 | 8.81 (s, 1H), 8.21 (s, 1H), 8.03 (s, 2H), 7.68 (d, J = 7.8 Hz, 1H), 7.51 (s, 1H), 7.47-7.35 (m, 3H), 7.30 (d, J = 8.2 Hz, 2H), 7.09 (d, J = 2.7 Hz, 1H), 6.98 (dd, J = 8.5, 2.7 Hz, 1H), 6.67-6.57 (m, 2H), 5.25 (dd, J = 13.4, 5.1 Hz, 1H), 4.90 (d, J = 15.0 Hz, 1H), 4.81 (d, J = 15.0 Hz, 1H), 4.49 (d, J = 17.3 Hz, 1H), 4.39 (d, J = 6.0 Hz, 2H), 4.31 (d, J = 17.2 Hz, 1H), 4.00 (s, 2H), 3.13 (ddd, J = 17.7, 13.4, 5.3 Hz, 1H), 2.88-2.78 (m, 1H), 2.46-2.43 (m, 1H), 2.07 (s, 4H) |
| 18 | 1-(4-{[4-(aminomethyl)phenyl]methoxy}-3-fluorophenyl)-3-{[2-(2,6-dioxopiperidin-3-yl)-1-oxo-2,3-dihydro-1H-isoindol-5-yl]methyl}urea | | 546.2 | 9.29 (s, 1H), 8.59 (s, 1H), 8.09 (s, 2H), 7.69 (d, J = 7.8 Hz, 1H), 7.51 (s, 1H), 7.44 (dd, J = 7.9, 1.4 Hz, 1H), 7.43-7.34 (m, 3H), 7.30 (d, J = 8.1 Hz, 2H), 6.90-6.73 (m, 3H), 5.25 (dd, J = 13.3, 5.1 Hz, 1H), 4.90 (d, J = 14.9 Hz, 1H), 4.81 (d, J = 15.0 Hz, 1H), 4.49 (d, J = 17.3 Hz, 1H), 4.40 (d, J = 6.0 Hz, 2H), 4.31 (d, J = 17.2 Hz, 1H), 4.00 (s, 2H), 3.13 (ddd, J = 17.7, 13.5, 5.4 Hz, 1H), 2.87-2.78 (m, 1H), 2.55-2.39 (m, 1H), 2.11-2.07 (m, 1H) |
| 19 | 1-(6-{[4-(aminomethyl)phenyl]methoxy}pyridazin-3-yl)-3-{[2-(2,6-dioxopiperidin-3-yl)-1-oxo-2,3-dihydro-1H-isoindol-5-yl]methyl}urea | | 530.3 | 11.00 (s, 1H), 9.60 (s, 1H), 8.35 (s, 1H), 8.13 (s, 3H), 7.77-7.71 (d, J = 7.8 Hz, 2H), 7.56-7.46 (m, J = 8.2 Hz, 6H), 7.25 (t, J = 9.1 Hz, 1H), 5.43 (s, 2H), 5.11 (dd, J = 13.3, 5.1 Hz, 1H), 4.52 (d, J = 6.0 Hz, 2H), 4.45-4.31 (m, J = 17.4 Hz, 2H), 4.04 (d, J = 5.7 Hz, 2H), 2.92 (ddd, J = 17.1, 13.6, 5.5 Hz, 1H), 2.62 (s, 1H), 2.38 (dd, J = 13.2, 4.6 Hz, 1H), 2.04-1.94 (m, 1H) |
| 20 | 1-(6-{[4-(aminomethyl)phenyl]methoxy}pyridin-3-yl)-3-{[2-(2,6-dioxopiperidin-3-yl)-1-oxo-2,3-dihydro-1H-isoindol-5-yl]methyl}urea | | 528.8 | 8.73-8.83 (m, 1 H), 8.33-8.37 (m, 1 H), 8.12-8.20 (m, 1 H), 7.76-7.81 (m, 1 H), 7.66-7.71 (m, 1 H), 7.51-7.56 (m, 1 H), 7.35-7.47 (m, 5 H), 6.94-7.05 (m, 1 H), 6.76-6.83 (m, 1 H), 5.26-5.30 (m, 2 H), 5.08-5.17 (m, 1 H), 4.25-4.50 (m, 4 H), 3.81-3.85 (m, 2 H), 2.89-2.96 (m, 1 H), 2.58-2.64 (m, 1 H), 2.34-2.39 (m, 1 H), 1.96-2.06 (m, 1 H) |
| 21 | 1-(4-{[4-(aminomethyl)-2-ethylphenyl]methoxy}phenyl)-3-{[2-(2,6-dioxopiperidin-3-yl)-1-oxo-2,3-dihydro-1H-isoindol-5-yl]methyl}urea | | 556.2 | 7.79-7.73 (m, 1H), 7.54 (s, 1H), 7.49 (d, J = 7.7 Hz, 2H), 7.35 (d, J = 1.9 Hz, 1H), 7.31-7.22 (m, 3H), 6.96-6.87 (m, 2H), 5.14 (dd, J = 13.3, 5.2 Hz, 1H), 5.08 (s, 2H), 4.55-4.40 (m, 4H), 4.10 (s, 2H), 2.90 (ddd, J = 17.5, 13.5, 5.4 Hz, 1H), 2.82-2.72 (m, 3H), 2.48 (qd, J = 13.2, 4.7 Hz, 1H), 2.16 (dtt, J = 13.3, 5.0, 2.5 Hz, 1H), 1.27 (t, J = 7.5 Hz, 3H) |

TABLE 1-continued

| Ex# | Name | R | LCMS (M + H)+ | 1H NMR (δ ppm) (400 MHz, DMSO-d6) |
|---|---|---|---|---|
| 22 | 1-(4-{[4-(aminomethyl)-2-n-propylphenyl]methoxy}phenyl)-3-{[2-(2,6-dioxopiperidin-3-yl)-1-oxo-2,3-dihydro-1H-isoindol-5-yl]methyl}urea | | 570.2 | 7.67 (d, J = 7.9 Hz, 1H), 7.45 (s, 1H), 7.39 (d, J = 7.9 Hz, 2H), 7.23 (d, J = 1.9 Hz, 1H), 7.21-7.13 (m, 3H), 6.85-6.77 (m, 2H), 5.05 (m, 2H), 4.98 (s, H), 4.45- 4.30 (m, 4H), 3.99 (s, 2H), 2.80 (ddd, J = 17.6, 13.5, 5.4 Hz, 1H), 2.67-2.57 (m, 3H), 2.38 (qd, J = 13.3, 4.7 Hz, 1H), 2.06 (dtd, J = 12.9, 5.3, 2.4 Hz, 1H), 1.65-1.52 (m, 2H), 0.89 (t, J = 7.3 Hz, 3H). |
| 23 | 1-(4-{[4-(aminomethyl)-2-methoxyphenyl]methoxy}phenyl)-3-{[2-(2,6-dioxopiperidin-3-yl)-1-oxo-2,3-dihydro-1H-isoindol-5-yl]methyl}urea | | 558.2 | 7.49 (d, J = 8.0 Hz, 1H), 7.53 (s, 1H), 7.60-7.52 (m, 2H), 7.49 (d, J = 7.9 Hz, 1H), 7.41 (dd, J = 8.0, 1.8 Hz, 1H), 7.33-7.22 (m, 2H), 6.97-6.86 (m, 2H), 5.16 (s, 2H), 5.21-5.08 (m, 1H), 4.57-4.38 (m, 4H), 4.12 (s, 2H), 2.91 (ddd, J = 18.4, 13.3, 5.3 Hz, 1H), 2.77 (ddd, J = 17.5, 4.8, 2.5 Hz, 1H), 2.48 (qd, J = 13.1, 4.8 Hz, 1H), 2.16 (dtd, J = 12.8, 5.3, 2.5 Hz, 1H) |
| 24 | 1-(4-{[4-(aminomethyl)-2-(propan-2-yloxy)phenyl]methoxy}phenyl)-3-{[2-(2,6-dioxopiperidin-3-yl)-1-oxo-2,3-dihydro-1H-isoindol-5-yl]methyl}urea | | 586.2 | 7.76 (d, J = 7.9 Hz, 1H), 7.54 (s, 1H), 7.48 (dd, J = 9.7, 7.7 Hz, 2H), 7.28-7.20 (m, 2H), 7.10 (d, J = 1.6 Hz, 1H), 6.99 (dd, J = 7.7, 1.6 Hz, 1H), 6.92-6.84 (m, 2H), 5.15 (dd, J = 13.3, 5.1 Hz, 1H), 5.05 (s, 2H), 4.71 (dq, J = 13.2, 7.1, 6.6 Hz, 1H), 4.55-4.40 (m, 4H), 4.09 (s, 2H), 2.91 (ddd, J = 17.6, 13.5, 5.4 Hz, 1H), 2.77 (ddd, J = 17.6, 4.7, 2.4 Hz, 1H), 2.48 (qd, J = 13.2, 4.7 Hz, 1H), 2.16 (dtd, J = 12.8, 5.3, 2.4 Hz, 1H), 1.37 (d, J = 6.0 Hz, 7H) |
| 25 | 1-(4-{[4-(aminomethyl)-2-chlorophenyl]methoxy}phenyl)-3-{[2-(2,6-dioxopiperidin-3-yl)-1-oxo-2,3-dihydro-1H-isoindol-5-yl]methyl}urea | | 562.1 | 7.76 (d, J = 7.9 Hz, 1H), 7.65 (d, J = 7.9 Hz, 1H), 7.49-7.45 (m, 2H), 7.24 (d, J = 8.8 Hz, 1H), 7.10 (s, 1H), 7.17 (d, J = 7.6 Hz), 6.89 (d, J = 8.8 Hz, 2H), 5.16 (s, 2H), 5.15 (m, 1H), 5.09 (s, 1H), 4.50 (m, 2H), 4.10 (s, 2H), 3.90 (s, 3H), 2.98-2.70 (m, 2H), 2.50-2.40 (m, 1H), 2.20-2.10 (m, 1H) |
| 26 | 1-(4-{[4-(aminomethyl)-2-(oxetan-3-yloxy)phenyl]methoxy}phenyl)-3-{[2-(2,6-dioxopiperidin-3-yl)-1-oxo-2,3-dihydro-1H-isoindol-5-yl]methyl}urea | | 600.2 | 7.76 (d, J = 7.9 Hz, 1H), 7.57-7.49 (m, 2H), 7.52-7.45 (m, 1H), 7.30-7.21 (m, 2H), 7.07 (dd, J = 7.8, 1.6 Hz, 1H), 6.96-6.87 (m, 2H), 6.66 (d, J = 1.6 Hz, 1H), 5.34 (tt, J = 5.9, 4.8 Hz, 1H), 5.15 (dd, J = 13.4, 5.1 Hz, 1H), 5.08-5.00 (m, 2H), 4.75-4.67 (m, 2H), 4.55-4.40 (m, 4H), 4.08 (s, 2H), 2.90 (ddd, J = 17.6, 13.5, 5.4 Hz, 1H), 2.77 (ddd, J = 17.6, 4.7, 2.5 Hz, 1H), 2.48 (qd, J = 13.3, 4.7 Hz, 1H), 2.16 (dtd, J = 12.8, 5.3, 2.4 Hz, 1H) |
| 27 | 1-(4-{[4-(aminomethyl)-2-cyclopropylphenyl]methoxy}phenyl)-3-{[2-(2,6-dioxopiperidin-3-yl)-1-oxo-2,3-dihydro-1H-isoindol-5-yl]methyl}urea | | 568.2 | 7.72 (d, J = 7.9 Hz, 1H), 7.50 (s, 1H), 7.44 (dd, J = 7.7, 2.4 Hz, 2H), 7.21 (td, J = 6.9, 2.0 Hz, 3H), 7.11 (d, J = 1.8 Hz, 1H), 6.93-6.84 (m, 2H), 5.20 (s, 2H), 5.10 (dd, J = 13.3, 5.2 Hz, 1H), 4.45-4.40 (m, J = 5.9 Hz, 4H), 4.02 (s, 2H), 2.86 (ddd, J = 18.6, 13.6, 5.4 Hz, 1H), 2.78-2.68 (m, 1H), 2.44 (qd, J = 13.2, 4.6 Hz, 1H), 2.16-1.96 (m, 2H), 1.00-0.89 (m, 2H), 0.73-0.64 (m, 2H) |

TABLE 1-continued

| Ex# | Name | R | LCMS (M + H)+ | 1H NMR (δ ppm) (400 MHz, DMSO-d6) |
|---|---|---|---|---|
| 28 | 1-(4-((2-aminobenzyl)oxy)phenyl)-3-((2-(2,6-dioxopiperidin-3-yl)-1-oxoisoindolin-5-yl)methyl)urea | | 514.2 | 10.66-11.15 (m, 1 H), 8.46 (s, 1 H) 7.69 (d, J = 7.6 Hz, 1 H), 7.51 (s, 1 H), 7.44 (d, J = 7.6 Hz, 1 H), 7.30 (d, J = 9.2 Hz, 2 H), 7.15 (d, J = 6.8 Hz, 1 H), 7.01 (t, J = 7.6 Hz, 1 H), 6.91 (d, J = 9.2 Hz, 2 H), 6.67 (d, J = 7.6 Hz, 2 H), 6.54 (t, J = 7.19 Hz, 1 H), 5.06-5.17 (m, 1 H), 4.8 -5.04 (m, 4 H), 4.25-4.53 (m, 4 H), 2.87-2.98 (m, 1 H), 2.61 (s, 1 H), 2.36-2.42 (m, 1 H), 1.93-2.05 (m, 1 H) |
| 29 | 1-(4-((4-(aminomethyl)benzyl)oxy)-3-chlorophenyl)-3-((2-(2,6-dioxopiperidin-3-yl)-1-oxoisoindolin-5-yl)methyl)urea | | 562.3 | 10.99 (s, 1 H), 8.78 (s, 1 H), 8.18 (br s, 3 H), 7.61-7.72 (m, 2 H), 7.36-7.60 (m, 6 H), 7.06-7.23 (m, 2 H), 6.84-7.06 (m, 1 H), 5.16 (s, 2 H), 5.03-5.13 (m, 1 H), 4.26-4.49 (m, 4 H), 4.04 (br s, 2 H), 2.82-3.02 (m, 1 H), 2.60 (d, J = 18.0 Hz, 1 H), 2.31-2.40 (m, 1 H), 1.91-2.06 (m, 1 H) |
| 30 | 1-(4-{[4-(aminomethyl)-2-i-propylphenyl]methoxy}phenyl)-3-{[2-(2,6-dioxopiperidin-3-yl)-1-oxo-2,3-dihydro-1H-isoindol-5-yl]methyl}urea | | 570.4 | (Methanol-d4) 7.76 (dd, J = 7.9, 0.7 Hz, 1H), 7.57-7.52 (m, 1H), 7.52-7.42 (m, 3H), 7.32-7.20 (m, 3H), 6.97-6.86 (m, 2H), 5.14-5.09 (m, 3H), 4.56-4.38 (m, 4H), 4.11 (s, 2H), 3.30-3.17 (m, 1H), 2.90 (ddd, J = 18.3, 13.3, 5.3 Hz, 1H), 2.76 (ddd, J = 17.6, 4.8, 2.5 Hz, 1H), 2.48 (qd, J = 13.2, 4.8 Hz, 1H), 2.16 (dtd, J = 12.9, 5.3, 2.5 Hz, 1H), 1.29 (d, J = 6.8 Hz, 6H) |
| 31 | 1-(4-{[4-(aminomethyl)-2-diflouromethoxyphenyl]methoxy}phenyl)-3-{[2-(2,6-dioxopiperidin-3-yl)-1-oxo-2,3-dihydro-1H-isoindol-5-yl]methyl}urea | | 594.1 | (Methanol-d4) 7.76 (d, J = 7.9 Hz, 1H), 7.64 (d, J = 8.2 Hz, 1H), 7.54 (s, 1H), 7.49 (d, J = 8.0 Hz, 1H), 7.34 (d, J = 6.2 Hz, 2H), 7.69-7.06 (m, 3H), 6.95-6.86 (m, 2H), 5.16 (d, J = 5.1 Hz, 1H), 5.12 (s, 2H), 4.50 (q, J = 9.5, 8.0 Hz, 4H), 4.14 (s, 2H), 2.90 (ddd, J = 18.3, 13.3, 5.2 Hz, 1H), 2.77 (d, J = 16.9 Hz, 1H), 2.49 (tt, J = 13.6, 6.9 Hz, 1H), 2.20-2.12 (m, 1H) |

Example 32

1-(4-{[4-(aminomethyl)phenyl]methoxy}phenyl)-3-({2-[(3 S)-3-methyl-2,6-dioxopiperidin-3-yl]-1-oxo-2,3-dihydro-1H-isoindol-5-yl}methyl)urea

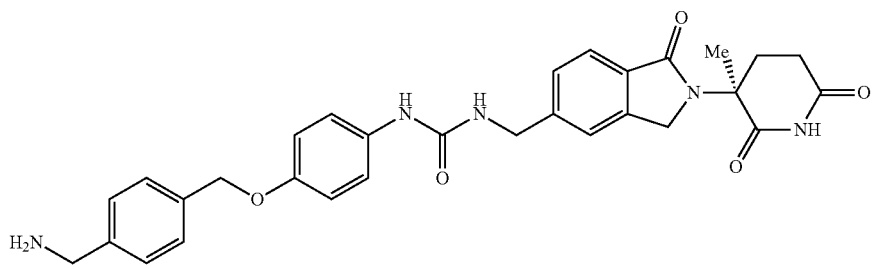 [SMILES: C[C@]1(N2Cc3cc(CNC(=O)Nc4ccc(OCc5ccc(CN)cc5)cc4)ccc3C2=O)CCC(=O)NC1=O]

Step 32-1: (S)-2-(3-methyl-2,6-dioxopiperidin-3-yl)-1-oxoisoindoline-5-carbonitrile

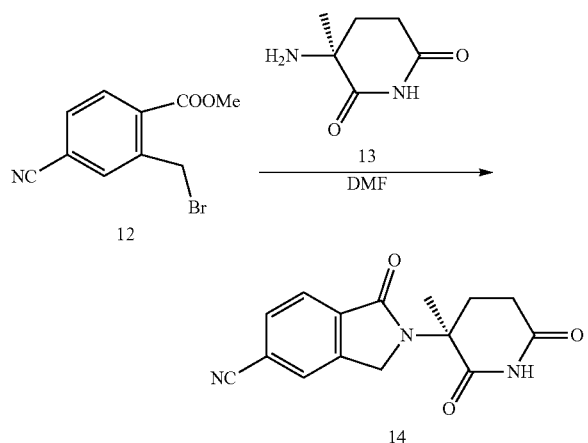

A solution of methyl 2-(bromomethyl)-4-cyano-benzoate (1500 mg, 5.900 mmol, 1.00 equiv) in DMF (15.0 mL) were added (3S)-3-amino-3-methyl-piperidine-2,6-dione (839 mg, 5.900 mmol, 1.00 equiv) and TEA (2.0 mL). The mixture was stirred overnight at 100° C. The resulting mixture was concentrated under reduced pressure. The residue was purified by silica gel column chromatography, eluted with DCM/MeOH (20:1) to afford (S)-2-(3-methyl-2,6-dioxopiperidin-3-yl)-1-oxoisoindoline-5-carbonitrile (1570 mg, 5.542 mmol, 93% yield) as a light yellow solid. LCMS (ESI, m/z): 284 [M+H]$^+$.

Step 32-2: tert-butyl (S)-((2-(3-methyl-2,6-dioxopiperidin-3-yl)-1-oxoisoindolin-5-yl)methyl)carbamate

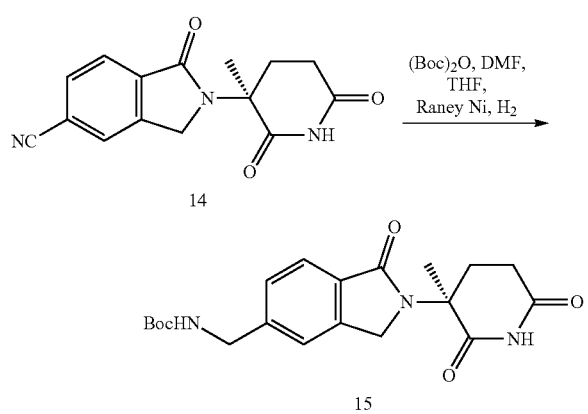

To a solution of (S)-2-(3-methyl-2,6-dioxopiperidin-3-yl)-1-oxoisoindoline-5-carbonitrile (780 mg, 2.750 mmol, 1.00 equiv) in a mixed solvent of DMF (10.0 mL) and THF (10.0 mL) were added di-tert-butyl dicarbonate (120 mg, 5.500 mmol, 2.00 equiv) and 6.0 g Raney Ni. The resulting mixture was stirred overnight at room temperature under hydrogen atmosphere. The solid was filtered out and the filter cake was washed with 30.0 mL MeCN. The filtrate was concentrated under reduced pressure. The residue was purified by Prep-TLC (DCM/MeOH 10:1) to afford tert-butyl (S)-((2-(3-methyl-2,6-dioxopiperidin-3-yl)-1-oxoisoindolin-5-yl)methyl)carbamate (247.0 mg, 0.637 mmol, 23% yield) as a white solid. LCMS (ESI, m/z): 388 [M+H]$^+$.

Step 32-3: (S)-3-(5-(aminomethyl)-1-oxoisoindolin-2-yl)-3-methylpiperidine-2,6-dione

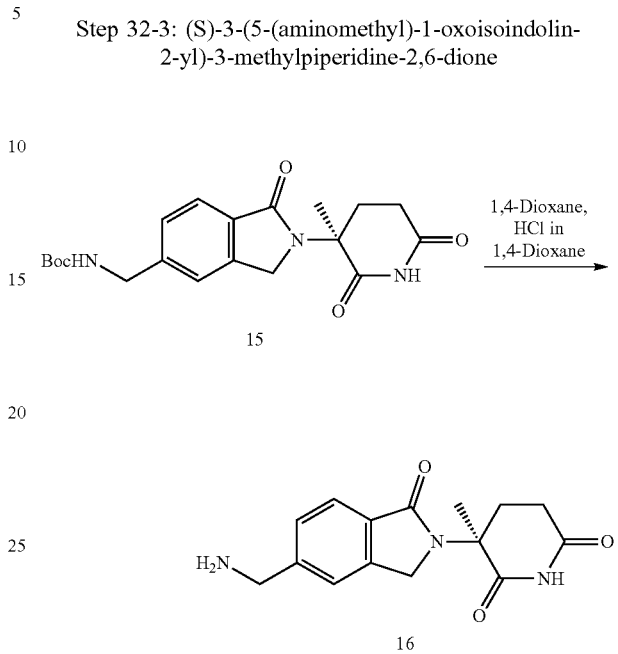

To a stirred mixture of tert-butyl (S)-((2-(3-methyl-2,6-dioxopiperidin-3-yl)-1-oxoisoindolin-5-yl)methyl)carbamate (247 mg, 0.640 mmol, 1.00 equiv) in 1,4-Dioxane (3.0 mL) was added 3.0 mL HCl in 1,4-Dioxane. The resulting mixture was stirred for 2 h at room temperature. The resulting mixture was concentrated under reduced pressure to afford (S)-3-(5-(aminomethyl)-1-oxoisoindolin-2-yl)-3-methylpiperidine-2,6-dione (200 mg, crude, HCl salt) as a light yellow solid. LCMS (ESI, m/z): 288 [M+H]$^+$.

Step 32-4: methyl 4-[(tert-butoxycarbonylamino)methyl]benzoate

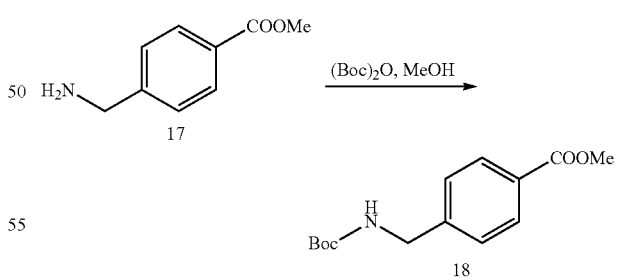

To a stirred mixture of methyl 4-(aminomethyl)benzoate (1000 mg, 6.050 mmol) in Methanol (10.0 mL) was added di-tert-butyl dicarbonate (1387 mg, 6.360 mmol). The resulting mixture was stirred overnight at room temperature. The resulting mixture was concentrated under reduced pressure to afford methyl 4-[(tert-butoxycarbonylamino)methyl]benzoate (1640 mg, 5.810 mmol, 95% yield) as a light yellow solid. LCMS (ESI, m/z): 266 [M+H]$^+$.

Step 32-5: tert-butyl N-[[4-(hydroxymethyl)phenyl]methyl]carbamate

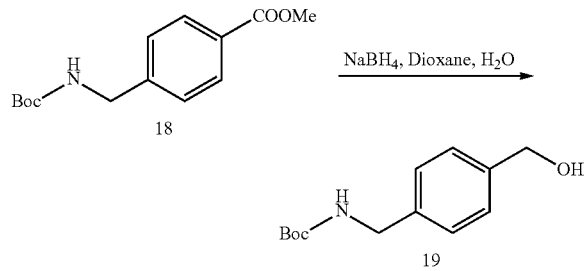

To a stirred solution of methyl 4-[(tert-butoxycarbonylamino)methyl]benzoate (900 mg, 3.390 mmol, 1.00 equiv) in a mixed solvent of 1,4-dioxane (5.0 mL) and water (5.0 mL) was added NaBH₄ (645 mg, 17.000 mmol, 5.00 equiv) in portions at room temperature. The resulting mixture was stirred for overnight at room temperature. The reaction was quenched with 50 mL water. The resulting mixture was extracted with 50.0 mL EtOAc. After combination of the organic phase and dried over anhydrous Na₂SO₄, filtration was performed and the filtrate was concentrated under reduced pressure. The crude product was purified by reverse flash chromatography with the following conditions (Spherial C18, 120 g, 20-40 m; Mobile Phase A: water (0.05% NH₄HCO₃), Mobile Phase B: ACN; Flow rate: 70 mL/min; Gradient: 0% B to 100% B in 20 min, 210 nm; RT: 9.0 min) to afford tert-butyl N-[[4-(hydroxymethyl)phenyl]methyl]carbamate (400.0 mg, 1.685 mmol, 49% yield) as a light yellow solid. LCMS (ESI, m/z): 238 [M+H]⁺.

Step 32-6: tert-butyl N-[[4-[(4-nitrophenoxy)methyl]phenyl]methyl]carbamate

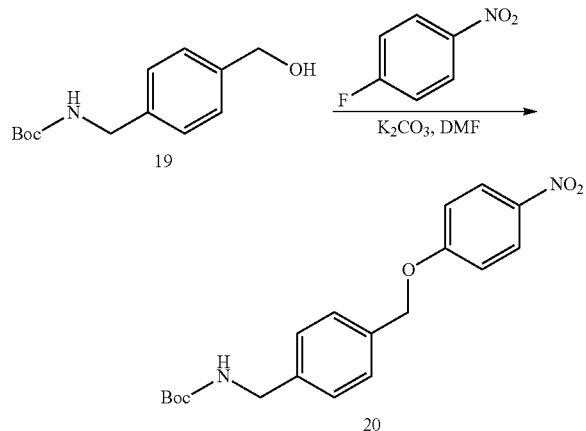

To a stirred mixture of tert-butyl N-[[4-(hydroxymethyl)phenyl]methyl]carbamate (400 mg, 1.690 mmol, 1.00 equiv) in DMF (8.0 mL) was added 1-fluoro-4-nitro-benzene (475 mg, 3.370 mmol, 2.00 equiv). To the above mixture was added K₂CO₃ (697 mg, 5.060 mmol, 3.00 equiv). The resulting mixture was stirred overnight at 100° C. Filtration was performed and the filter cake was washed with 15.0 mL MeCN. The filtrate was concentrated under reduced pressure. The crude product was purified by reverse flash chromatography with the following conditions (Spherial C18, 80 g, 20-40 m; Mobile Phase A: water (0.05% TFA), Mobile Phase B: ACN; Flow rate: 70 mL/min; Gradient: 0% B to 100% B in 20 min, 210 nm; RT: 8.5 min) to afford tert-butyl N-[[4-[(4-nitrophenoxy)methyl]phenyl]methyl]carbamate (410.0 mg, 1.144 mmol, 67% yield) as a yellow solid. LCMS (ESI, m/z): 359 [M+H]⁺.

Step 32-7: tert-butyl N-[[4-[(4-aminophenoxy)methyl]phenyl]methyl]carbamate

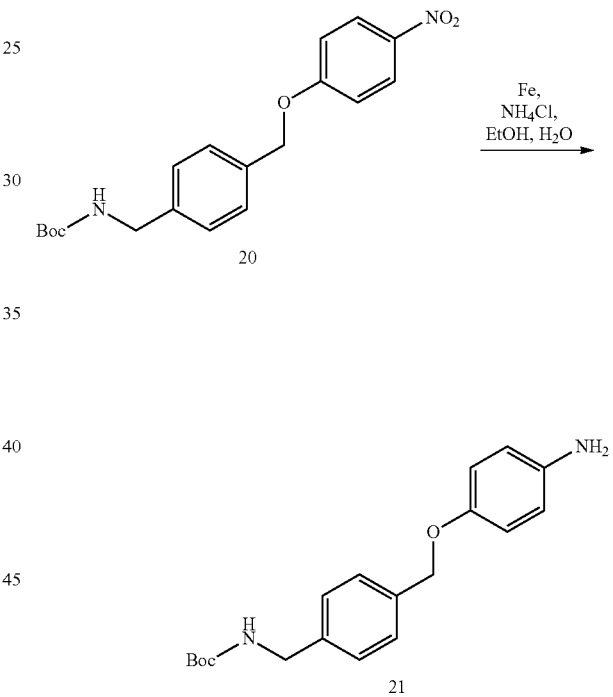

To a stirred mixture of tert-butyl N-[[4-[(4-nitrophenoxy)methyl]phenyl]methyl]carbamate (390 mg, 1.090 mmol, 1.00 equiv) in mixed solvent of ethanol (5.0 mL) and water (1.0 mL) were added Fe (303 mg, 5.450 mmol, 5.00 equiv) and NH₄Cl (587 mg, 10.880 mmol, 10.00 equiv). The above mixture was stirred for 2 h at 80° C. 20 mL ethanol was added to dilute to reaction and the solid was filtered out. The filtrate was concentrated under reduced pressure. He residue was re-dissolved in 20.0 mL EtOAc and filtered. The filtrate was concentrated under vacuum to afford tert-butyl N-[[4-[(4-aminophenoxy)methyl]phenyl]methyl]carbamate (342.0 mg, 1.041 mmol, 95% yield) as a brown solid. LCMS (ESI, m/z): 329 [M+H]⁺.

Step 32-8: tert-butyl (S)-(4-((4-(3-((2-(3-methyl-2,6-dioxopiperidin-3-yl)-1-oxoisoindolin-5-yl)methyl)ureido)phenoxy)methyl)benzyl)carbamate

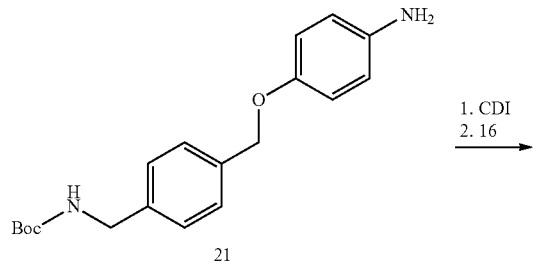

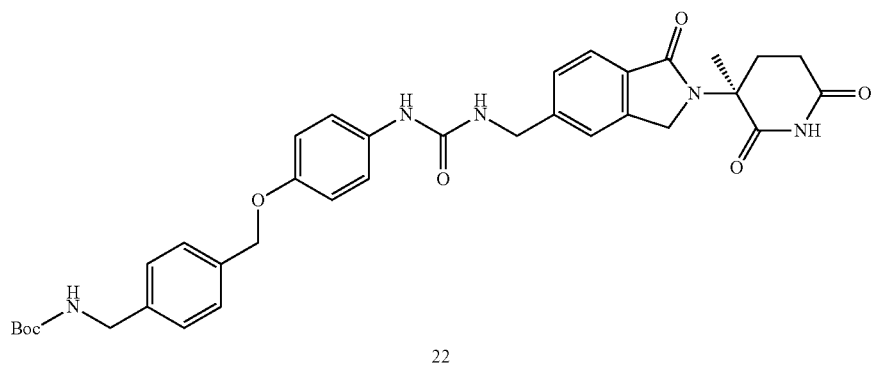

To a stirred mixture of tert-butyl N-[[4-[(4-aminophenoxy)methyl]phenyl]methyl]carbamate (109 mg, 0.330 mmol, 1.00 equiv) in DCE (3.0 mL) was added carbonyl diimidazole (59 mg, 0.370 mmol, 1.12 equiv). The resulting mixture was stirred for 4 h at 60° C. It was concentrated under reduced pressure and the residue was dissolved in 3.0 mL MeCN. To the above mixture was added (S)-3-(5-(aminomethyl)-1-oxoisoindolin-2-yl)-3-methylpiperidine-2,6-dione HCl salt (107 mg, 0.330 mmol, 1.00 equiv) and 0.3 mL TEA in 1.0 mL DMF. The resulting mixture was stirred overnight at room temperature. The resulting mixture was concentrated under reduced pressure. The crude product was purified by reverse flash chromatography with the following conditions (Spherial C18, 40 g, 20-40 m; Mobile Phase A: water (0.05% TFA), Mobile Phase B: ACN; Flow rate: 40 mL/min; Gradient: 0% B to 100% B in 20 min, 210 nm; RT: 7 min) to afford tert-butyl (S)-(4-((4-(3-((2-(3-methyl-2,6-dioxopiperidin-3-yl)-1-oxoisoindolin-5-yl)methyl)ureido)phenoxy)methyl)benzyl)carbamate (100.0 mg, 0.155 mmol, 46% yield) as a light brown solid. LCMS (ESI, m/z): 642 [M+H]$^+$.

Step 32-9: 1-[4-[[4-(aminomethyl)phenyl]methoxy]phenyl]-3-[[1-oxo-2-[rac-(3S)-3-methyl-2,6-dioxo-3-piperidyl]isoindolin-5-yl]methyl]urea

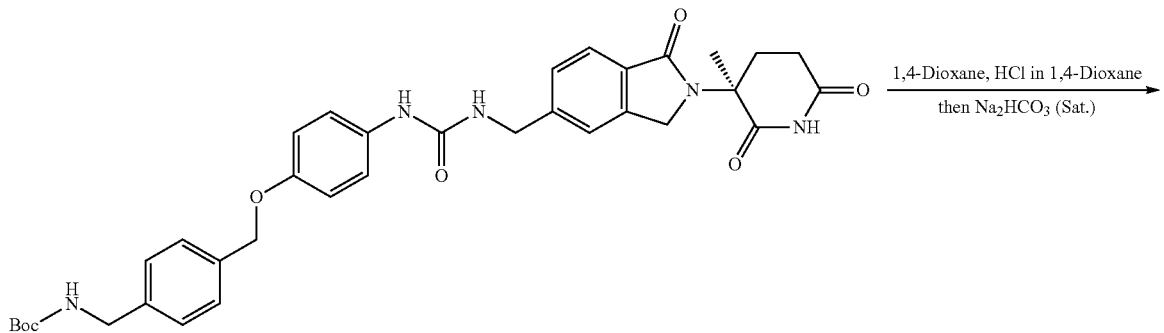

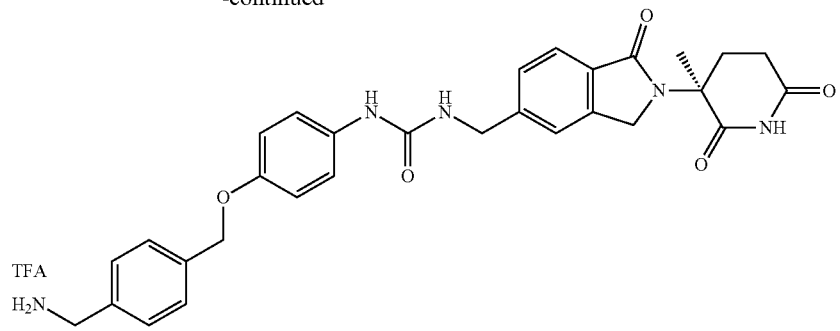

EX. 32

To a stirred mixture of tert-butyl (S)-(4-((4-(3-((2-(3-methyl-2,6-dioxopiperidin-3-yl)-1-oxoisoindolin-5-yl)methyl)ureido)phenoxy)methyl)benzyl)carbamate (95 mg, 0.150 mmol, 1.00 equiv) in 1,4-dioxane (2.0 mL) was added HCl in 1,4-Dioxane (3.0 mL). The resulting mixture was stirred for 2 h at room temperature. The resulting mixture was concentrated under reduced pressure. The crude product was dissolved in 1.0 ml ACN, and then added 1.0 ml saturated NaHCO₃ solution to adjust the pH value to 8. It was concentrated and the crude product was purified directly by Prep-HPLC with the following conditions (Column: Xselect CSH C18 OBD Column 30*150 mm 5 m, n; Mobile Phase A: Water (0.05% TFA), Mobile Phase B: ACN; Flow rate: 60 mL/min; Gradient: 2% B to 32% B in 10 min, 32% B; Wave Length: 254 nm; RT1(min): 9.32) to afford 1-(4-{[4-(aminomethyl)phenyl]methoxy}phenyl)-3-({2-[(3S)-3-methyl-2,6-dioxopiperidin-3-yl]-1-oxo-2,3-dihydro-1H-isoindol-5-yl}methyl)urea (40.0 mg, 49% yield, TFA salt) as a white solid. LCMS (ESI, m/z): 542 [M+H]⁺. ¹H NMR (400 MHz, Methanol-d₄) δ 7.68 (d, J=7.9 Hz, 1H), 7.57-7.42 (m, 6H), 7.28-7.20 (m, 2H), 6.93-6.87 (m, 2H), 5.09 (s, 2H), 4.68 (s, 2H), 4.49 (s, 2H), 4.11 (s, 2H), 2.88-2.73 (m, 2H), 2.73-2.61 (m, 1H), 2.04-1.93 (m, 1H), 1.77 (s, 3H).

Example 33

1-(4-{[4-(aminomethyl)phenyl]methoxy}phenyl)-3-({2-[(3R)-3-methyl-2,6-dioxopiperidin-3-yl]-1-oxo-2,3-dihydro-1H-isoindol-5-yl}methyl)urea Step 33-1: (R)-2-(3-methyl-2,6-dioxopiperidin-3-yl)-1-oxoisoindoline-5-carbonitrile

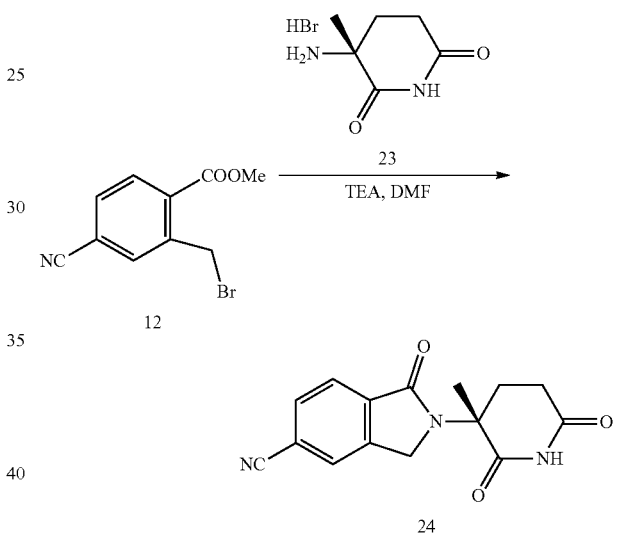

To a stirred mixture of (3R)-3-amino-3-methyl-piperidine-2,6-dione; hydrobromide (1000 mg, 4.483 mmol, 1.00 equiv) in DMF (10.0 mL) was added methyl 2-(bromomethyl)-4-cyano-benzoate (1139 mg, 4.483 mmol, 1.00 equiv) and TEA (0.8 mL). The resulting mixture was stirred for 12 h at 110° C. Desired product could be detected by LCMS. The resulting mixture was concentrated under vacuum. The residue was purified by silica gel column chromatography, eluted with DCM/MeOH (20/1) to afford (R)-2-(3-methyl-

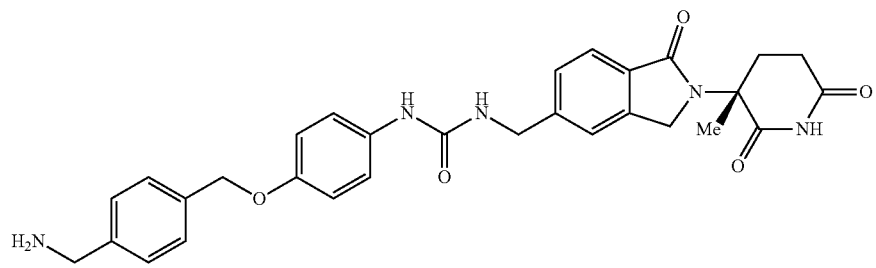 [SMILES: C[C@@]1(N2Cc3cc(CNC(=O)Nc4ccc(OCc5ccc(CN)cc5)cc4)ccc3C2=O)CCC(=O)NC1=O]

2,6-dioxopiperidin-3-yl)-1-oxoisoindoline-5-carbonitrile (320.0 mg, 1.130 mmol, 25% yield) as a yellow solid. LCMS (ESI, m/z): 284 [M+H]⁺.

Step 33-2: tert-butyl (R)-((2-(3-methyl-2,6-dioxopiperidin-3-yl)-1-oxoisoindolin-5-yl)methyl)carbamate

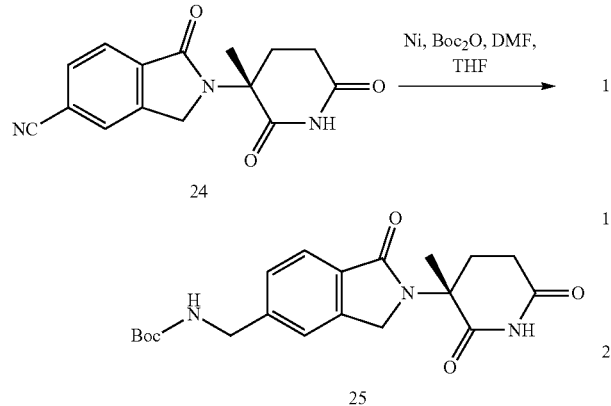

To a stirred mixture of 2.0 g Raney Ni and (R)-2-(3-methyl-2,6-dioxopiperidin-3-yl)-1-oxoisoindoline-5-carbonitrile (200 mg, 0.706 mmol, 1.00 equiv) in a mixed solvent of DMF (8.0 mL) in THF (12.0 mL) was added Boc₂O (308 mg, 1.411 mmol, 2.00 equiv) at room temperature. The resulting mixture was stirred for 12 h at room temperature under H₂ atmosphere. Desired product could be detected by LCMS. The solid was filtered out, the filter cake was washed with 60.0 mL MeCN. The filtrate was concentrated under reduced pressure. The residue was purified by Prep-TLC [MeOH/DCM (1/20)] to afford tert-butyl (R)-((2-(3-methyl-2,6-dioxopiperidin-3-yl)-1-oxoisoindolin-5-yl)methyl)carbamate (92.0 mg, 0.237 mmol, 34% yield) as a colorless oil. LCMS (ESI, m/z): 388 [M+H]⁺.

Step 33-3: (R)-3-(5-(aminomethyl)-1-oxoisoindolin-2-yl)-3-methylpiperidine-2,6-dione

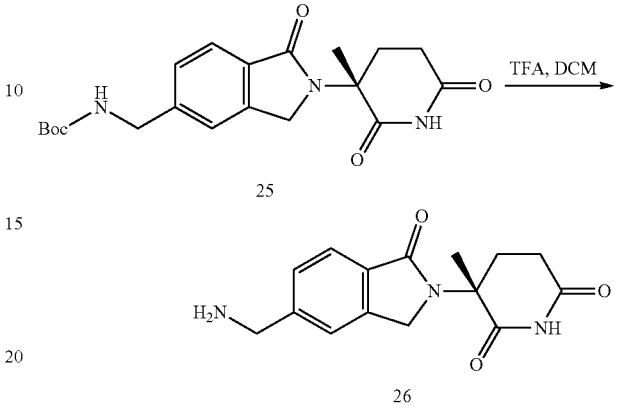

To a stirred mixture of tert-butyl (R)-((2-(3-methyl-2,6-dioxopiperidin-3-yl)-1-oxoisoindolin-5-yl)methyl)carbamate (92 mg, 0.237 mmol, 1.00 equiv) in DCM (10.0 mL) was added TFA (3.0 mL). The resulting mixture was stirred for 1 h at room temperature and then concentrated under vacuum to afford (R)-3-(5-(aminomethyl)-1-oxoisoindolin-2-yl)-3-methylpiperidine-2,6-dione (107.0 mg, crude, TFA salt) as a yellow oil. LCMS (ESI, m/z): 288 [M+H]⁺.

Step 33-4: (R)-1-(4-((4-(aminomethyl)benzyl)oxy)phenyl)-3-((2-(3-methyl-2,6-dioxopiperidin-3-yl)-1-oxoisoindolin-5-yl)methyl)urea

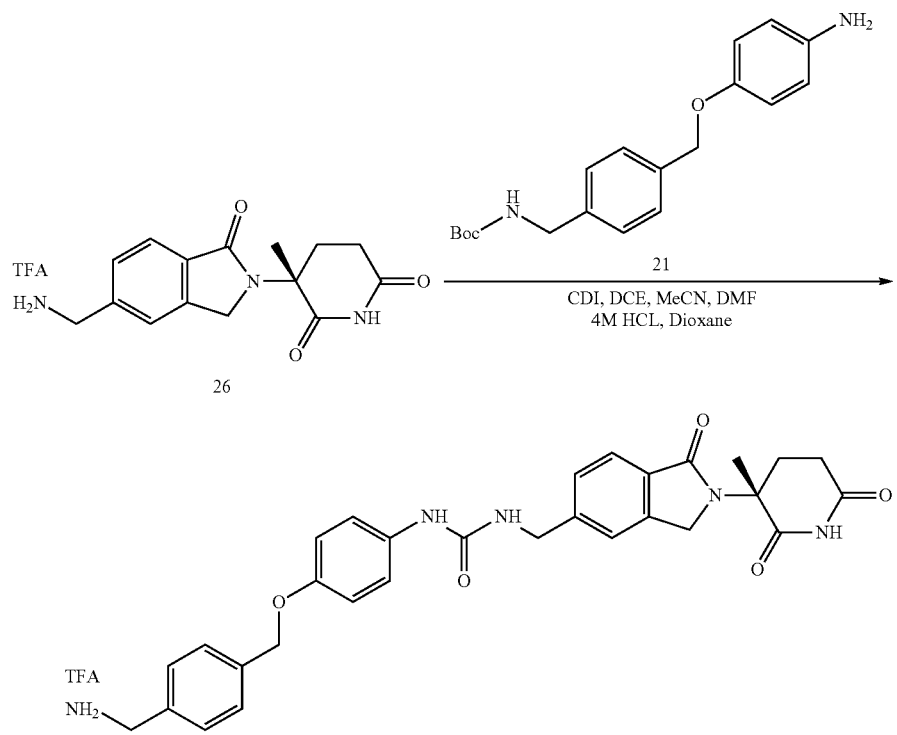

EX. 33

To a stirred mixture of (R)-3-(5-(aminomethyl)-1-oxoisoindolin-2-yl)-3-methylpiperidine-2,6-dione trifluoroacetic acid salt (100 mg, 0.249 mmol, 1.00 equiv) and 0.5 mL TEA in DCE (4.0 mL) was added carbonyl diimidazole (48 mg, 0.298 mmol, 1.20 equiv) at room temperature. The resulting mixture was stirred at 60° C. for 1 h and then concentrated under reduced pressure. The residue was re-dissolved in 4.0 mL MeCN and add a solution of tert-butyl N-[[4-[(4-aminophenoxy)methyl]phenyl]methyl]carbamate (98 mg, 0.298 mmol, 1.20 equiv). The resulting mixture was stirred for 2 h at room temperature and concentrated under vacuum. The above crude Boc-protected intermediate was dissolved in 5.0 mL 1,4-dioxane and 5.0 mL 4 M HCl in dioxane and then stirred for 2 h at room temperature. After the mixture was concentrated under reduced pressure, the crude product was dissolved in 1.0 ml ACN, and then added 1.0 ml saturated $NaHCO_3$ solution to adjust the PH value to 8. The resulting solution of the crude product was purified by directly Prep-HPLC (Column: Xselect CSH C18 OBD Column 30*150 mm 5 μm, n; Mobile Phase A: Water (0.05% TFA), Mobile Phase B: ACN; Flow rate: 60 mL/min; Gradient: 2% B to 25% B in 10 min, 25% B; Wave Length: 254 nm; RT1 (min): 9.37) to afford (R)-1-(4-((4-(aminomethyl)benzyl)oxy)phenyl)-3-((2-(3-methyl-2,6-dioxopiperidin-3-yl)-1-oxoisoindolin-5-yl)methyl)urea (34.5 mg, 0.054 mmol, 15%, 100% ee) (TFA salt) as a white solid. LCMS (ESI, m/z): 542 $[M+H]^+$. $^1H$ NMR: (400 MHz, Methanol-$d_4$) δ 7.68 (d, J=7.9 Hz, 1H), 7.57-7.49 (m, 3H), 7.49-7.42 (m, 3H), 7.28-7.21 (m, 2H), 6.94-6.87 (m, 2H), 5.09 (s, 2H), 4.68 (s, 1H), 4.49 (s, 2H), 4.11 (s, 2H), 2.89-2.73 (m, 2H), 2.73-2.61 (m, 1H), 2.04-1.93 (m, 1H), 1.77 (s, 3H).

Example 34

3-{[2-(2,6-dioxopiperidin-3-yl)-1-oxo-2,3-dihydro-1H-isoindol-5-yl]methyl}-1-(4-{[(1r,4r)-4-(aminomethyl)cyclohexyl]methoxy}phenyl)urea

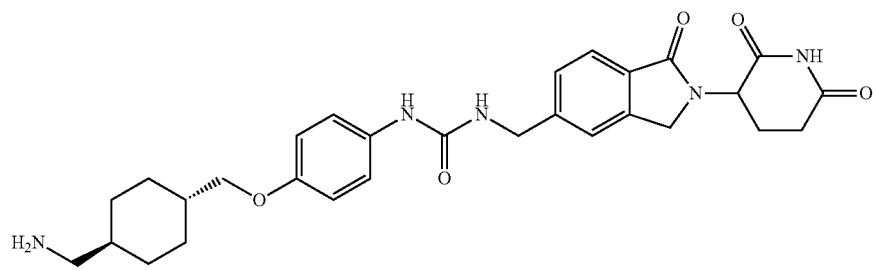 [SMILES: NC[C@H]1CC[C@H](COc2ccc(NC(=O)NCc3ccc4c(c3)CN(C3CCC(=O)NC3=O)C4=O)cc2)CC1]

Step 34-1: tert-butyl N-[[4-[(4-nitrophenoxy)methyl]cyclohexyl]methyl]carbamate

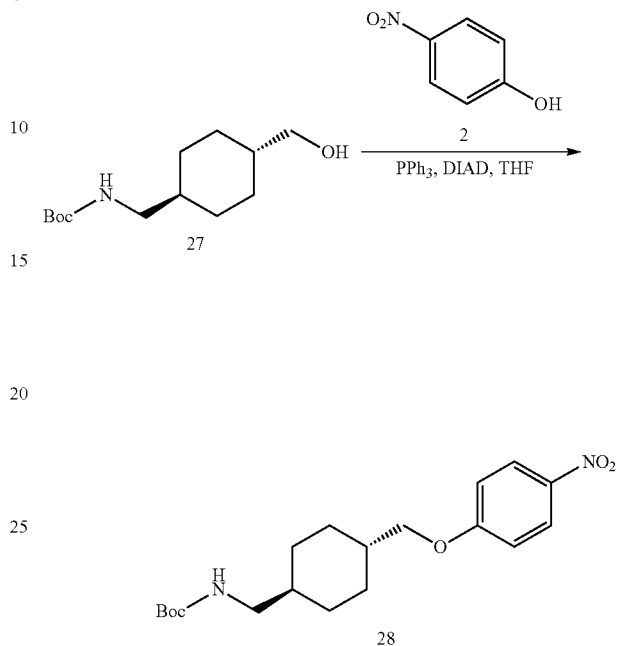

To a stirred mixture of tert-butyl (((1r,4r)-4-(hydroxymethyl)cyclohexyl)methyl)carbamate (300 mg, 1.234 mmol, 1.00 equiv) in THF (6.0 mL) were added 4-nitrophenol (171 mg, 1.230 mmol, 1.00 equiv) and Triphenylphosphine (355 mg, 1.360 mmol, 1.10 equiv). To the above mixture was added DIAD (0.3 mL, 1.360 mmol, 1.10 equiv) dropwise at 0° C. and then stirred for 2 h at room temperature. The resulting mixture was concentrated under reduced pressure. The crude product was purified by reverse flash chromatography with the following conditions (Spherial C18, 120 g, 20-40 m; Mobile Phase A: water (0.05% $NH_4HCO_3$), Mobile Phase B: ACN; Flow rate: 90 mL/min; Gradient: 0% B to 100% B in 30 min, 210 nm; RT: 15.0 min) to afford tert-butyl (((1r,4r)-4-((4-nitrophenoxy)methyl)cyclohexyl)methyl)carbamate (340.0 mg, 0.932 mmol, 75% yield) as a light yellow solid. LCMS (ESI, m/z): 365 $[M+H]^+$.

Step 34-2: tert-butyl (((1r,4r)-4-((4-aminophenoxy)methyl)cyclohexyl)methyl)carbamate

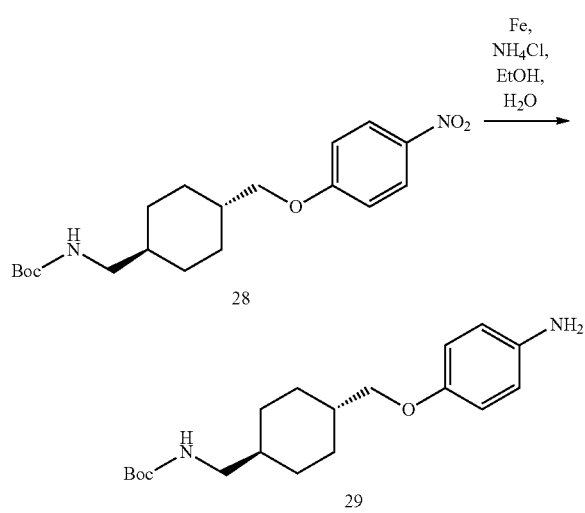

A stirred solution of tert-butyl (((1r,4r)-4-((4-nitrophenoxy)methyl)cyclohexyl)methyl)carbamate (330 mg, 0.910 mmol) in mixed solvent of Ethanol (5.0 mL) and Water (1.0 mL) were added NH$_4$Cl (484 mg, 9.070 mmol, 10.00 equiv) and Fe (253 mg, 4.530 mmol, 5.00 equiv). The resulting mixture was stirred for 2 h at 80° C. and then diluted with 20.0 mL ethanol. The solid was filtered out and the filtrate was concentrated under reduced pressure. 30.0 mL EA was added to the above residue and once more filtration again. The filtrate was concentrated under vacuum to afford tert-butyl (((1r,4r)-4-((4-aminophenoxy)methyl)cyclohexyl)methyl)carbamate (225.0 mg, 0.672 mmol, 74% yield) as a light brown solid. LCMS (ESI, m/z): 335 [M+H]$^+$.

Step 34-3: tert-butyl (((1r,4r)-4-((4-(3-((2-(2,6-dioxopiperidin-3-yl)-1-oxoisoindolin-5-yl)methyl)ureido)phenoxy)methyl)cyclohexyl)methyl)carbamate

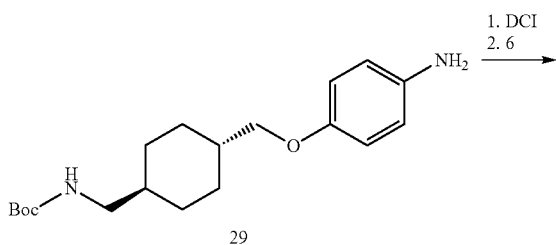

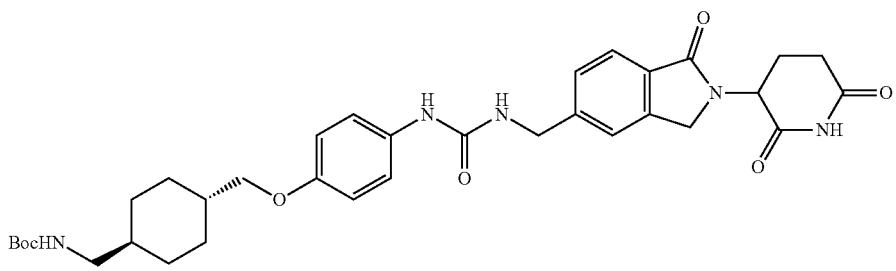

To a stirred mixture of tert-butyl (((1r,4r)-4-((4-amino-phenoxy)methyl)cyclohexyl)methyl)carbamate (50 mg, 0.150 mmol) in DCE (2.0 mL) was added carbonyl diimidazole (26 mg, 0.160 mmol, 1.07 equiv). The resulting mixture was stirred for 2 h at 60° C. The resulting mixture was concentrated under reduced pressure. To the above residue was added 2.0 mL MeCN and then a solution of 3-[5-(aminomethyl)-1-oxo-isoindolin-2-yl]piperidine-2,6-dione trifluoroacetic acid salt (58 mg, 0.1500 mmol, 1.00 equiv) and 0.5 mL TEA in 1.0 mL DMF was added. The resulting mixture was stirred for additional 2 h at rt. This was purified by reverse flash chromatography with the following conditions (Spherial C18, 80 g, 20-40 m; Mobile Phase A: water (0.05% TFA), Mobile Phase B: ACN; Flow rate: 70 mL/min; Gradient: 0% B to 100% B in 10 min, 210 nm; RT: 12 min) to afford tert-butyl (((1r,4r)-4-((4-(3-((2-(2,6-dioxopiperidin-3-yl)-1-oxoisoindolin-5-yl)methyl)ureido) phenoxy)methyl)cyclohexyl)methyl)carbamate (33.0 mg, 0.052 mmol, 34% yield) as a light yellow solid. LCMS (ESI, m/z): 634 [M+H]$^+$.

Step 34-4: 1-(4-(((1r,4r)-4-(aminomethyl)cyclohexyl)methoxy)phenyl)-3-((2-(2,6-dioxopiperidin-3-yl)-1-oxoisoindolin-5-yl)methyl)urea To a stirred mixture of tert-butyl (((1r,4r)-4-((4-(3-((2-(2,6-dioxopiperidin-3-yl)-1-oxoisoindolin-5-yl)methyl)ureido) phenoxy)methyl)cyclohexyl)methyl)carbamate (28 mg, 0.040 mmol) in 1,4-Dioxane (2.0 mL) was added HCl in 1,4-Dioxane (2.0 mL) dropwise at room temperature. The resulting mixture was stirred for 2 h at room temperature and then concentrated under reduced pressure. The crude product was dissolved in 1.0 ml ACN, and then added 1.0 ml saturated NaHCO$_3$ solution to adjust the PH value to 8. The resulting solution was purified Prep-HPLC with the following conditions (Column: Xselect CSH C18 OBD Column 30*150 mm 5 m, n; Mobile Phase A: Water (0.1% FA), Mobile Phase B: ACN; Flow rate: 60 mL/min; Gradient: 2% B to 20% B in 10 min, 20% B; Wave Length: 254 nm; RT1 (min): 10.57) to afford 1-(4-(((1r,4r)-4-(aminomethyl)cyclohexyl)methoxy)phenyl)-3-((2-(2,6-dioxopiperidin-3-yl)-1-oxoisoindolin-5-yl)methyl)urea (12.0 mg, 0.022 mmol, 50% yield) as a white solid. LCMS (ESI, m/z): 534 [M+H]$^+$. $^1$H NMR (300 MHz, Methanol-d$_4$) δ 8.85 (s, 1H), 7.77 (d, J=7.9 Hz, 1H), 7.58-7.45 (m, 2H), 7.24 (d, J=9.0 Hz, 2H), 7.00 (s, 1H), 6.82 (d, J=9.0 Hz, 2H), 5.14 (dd, J=13.3, 5.2 Hz, 1H), 4.58-4.39 (m, 4H), 3.77 (d, J=6.2 Hz, 2H), 3.00-2.90 (m, 1H), 2.70-2.60 (m, 4H), 2.59-2.40 (m, 2H), 2.00 (m, 1H), 1.99-1.75 (m, 4H), 1.70-1.55 (s, 1H), 1.50-1.42 (s, 1H), 1.10-0.85 (m, 4H).

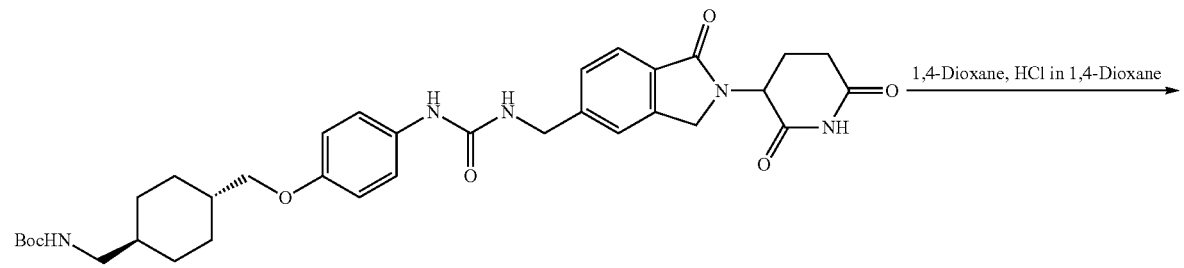

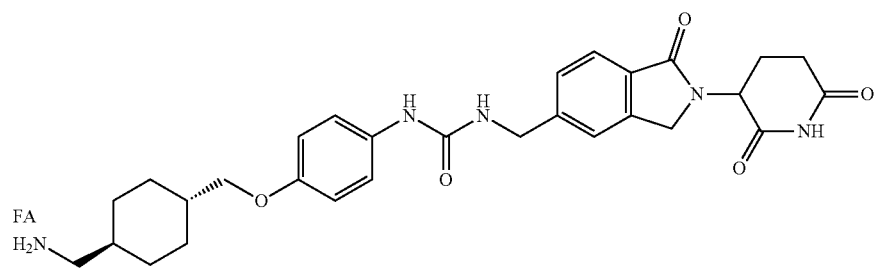

EX. 34

Example 35

3-{[2-(2,6-dioxopiperidin-3-yl)-1-oxo-2,3-dihydro-1H-isoindol-5-yl]methyl}-1-[(1r,4r)-4-{[4-(aminomethyl)phenyl]methoxy}cyclohexyl]urea

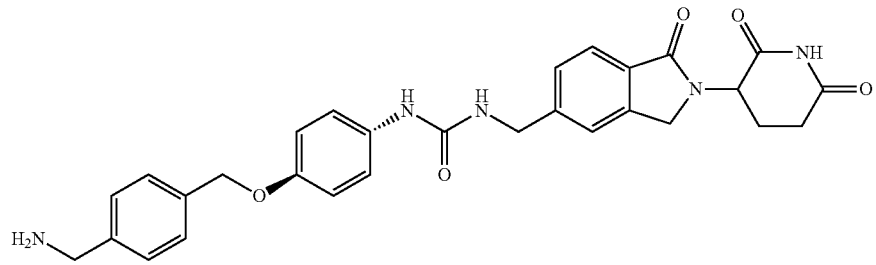

Step 35-1: (1r,4r)-4-(2,5-dimethyl-1H-pyrrol-1-yl)cyclohexan-1-ol

Step 35-2: 1-((1r,4r)-4-((4-bromobenzyl)oxy)cyclohexyl)-2,5-dimethyl-1H-pyrrole

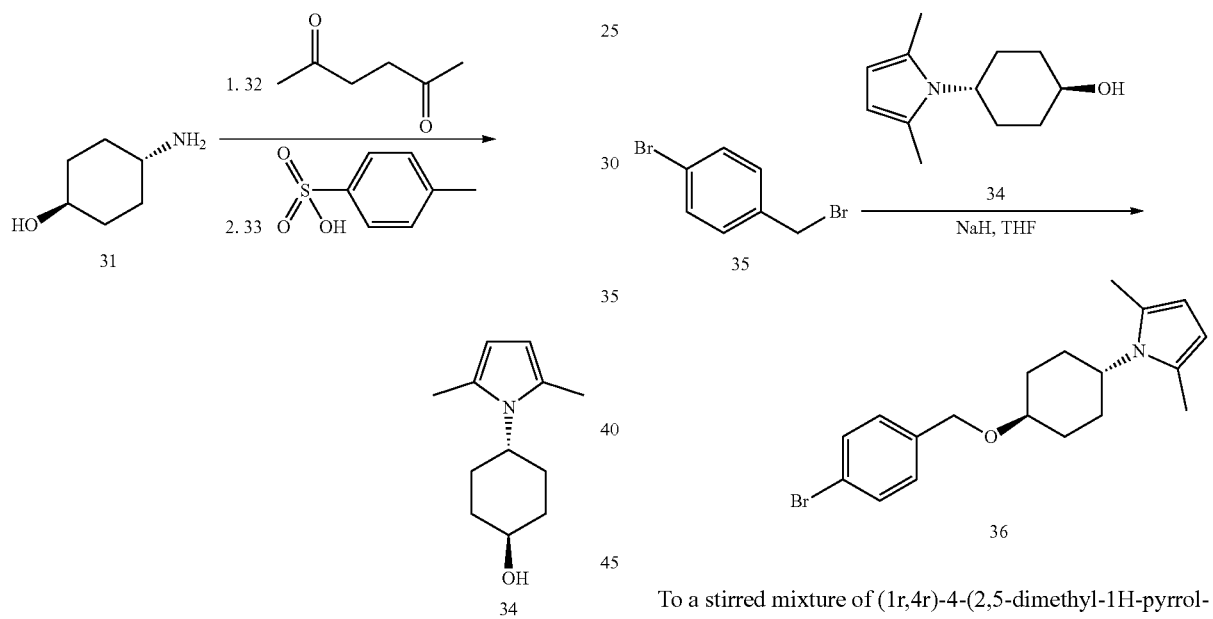

To a stirred mixture of (1r,4r)-4-aminocyclohexan-1-ol (240 mg, 2.080 mmol, 1.00 equiv) in Methanol (5.0 mL) was added hexane-2,5-dione (0.3 mL, 2.080 mmol, 1.00 equiv). The above mixture was added p-toluenesulfonic acid (86 mg, 0.500 mmol, 2.40 equiv) and stirred for 4 h at 60° C. The resulting mixture was concentrated under reduced pressure. The residue was dissolved 50.0 mL EA and washed with 15 mL 1M HCl aq and then 15 mL saturated NaHCO$_3$ aq solution. After dried over anhydrous Na$_2$SO$_4$ and filtration the filtrate was concentrated under reduced pressure to afford (1r,4r)-4-(2,5-dimethyl-1H-pyrrol-1-yl)cyclohexan-1-ol (230 mg, 1.189 mmol, 57% yield) as a yellow solid. LCMS (ESI, m/z): 194 [M+H]$^+$.

To a stirred mixture of (1r,4r)-4-(2,5-dimethyl-1H-pyrrol-1-yl)cyclohexan-1-ol (332 mg, 1.720 mmol, 1.00 equiv) in THF (5.0 mL) was added NaH (82 mg, 3.440 mmol, 2.00 equiv) in portions at room temperature. To the above mixture was added a solution of 1-bromo-4-(bromomethyl)benzene (430 mg, 1.720 mmol) in 5.0 mL THF. The resulting mixture was stirred overnight at 60° C. The reaction was quenched with 20.0 mL H$_2$O. The resulting mixture was extracted with 50.0 mL*3 EA. The combined organic layers was dried over anhydrous Na$_2$SO$_4$. After filtration, the filtrate was concentrated under reduced pressure. The crude product was purified by reverse flash chromatography with the following conditions (Spherial C18, 80 g, 20-40 m; Mobile Phase A: water (0.05% TFA), Mobile Phase B: ACN; Flow rate: 70 mL/min; Gradient: 0% B to 100% B in 10 min, 210 nm; RT: 6 min) to afford 1-((1r,4r)-4-((4-bromobenzyl)oxy)cyclohexyl)-2,5-dimethyl-1H-pyrrole (420.0 mg, 1.159 mmol, 67% yield) as a yellow solid. LCMS (ESI, m/z): 362 [M+H]$^+$.

Step 35-3: tert-butyl (4-((((1r,4r)-4-(2,5-dimethyl-1H-pyrrol-1-yl)cyclohexyl)oxy)methyl)benzyl)carbamate

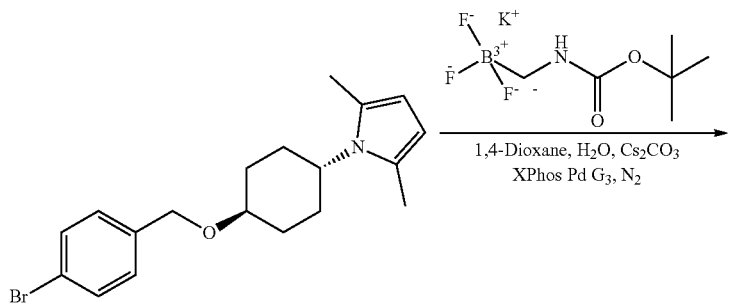

36

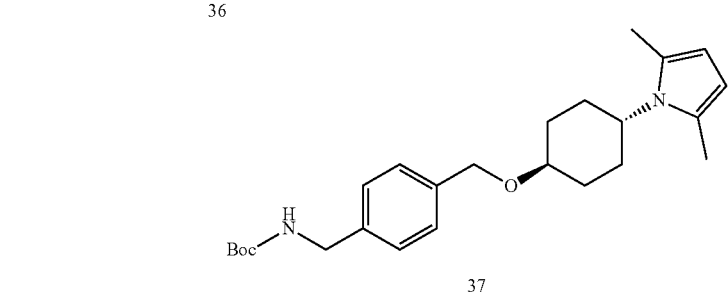

37

To a stirred mixture of 1-(((1r,4r)-4-((4-bromobenzyl)oxy)cyclohexyl)-2,5-dimethyl-1H-pyrrole (420 mg, 1.160 mmol, 1.00 equiv) in mixed solvent of 1,4-Dioxane (3.0 mL) and Water (0.3 mL) was added potassium; potassium N-Boc-aminomethyl trifluoroborate (273 mg, 1.160 mmol, 1.16 equiv). To the above mixture was added $Cs_2CO_3$ (1130 mg, 3.480 mmol, 3.48 equiv) and XPhos Pd G3 (106 mg, 0.120 mmol, 0.12 equiv). The resulting mixture was stirred overnight at 110° C. under nitrogen atmosphere. The reaction was quenched with 10.0 mL water and then extracted with 40.0 mL*3 EtOAc. The combined organic layers were dried over anhydrous $Na_2SO_4$. After filtration, the filtrate was concentrated under reduced pressure. The above residue was purified by reverse flash chromatography with the following conditions (Spherial C18, 80 g, 20-40 m; Mobile Phase A: water (0.05% $NH_4HCO_3$), Mobile Phase B: ACN; Flow rate: 70 mL/min; Gradient: 0% B to 100% B in 20 min, 210 nm; RT: 10 min) to afford tert-butyl (4-((((1r,4r)-4-(2,5-dimethyl-1H-pyrrol-1-yl)cyclohexyl)oxy)methyl)benzyl)carbamate (125.0 mg, 0.303 mmol, 26% yield) as a yellow oil. LCMS (ESI, m/z): 413 [M+H]$^+$.

Step 35: tert-butyl (4-((((1r,4r)-4-aminocyclohexyl)oxy)methyl)benzyl)carbamate

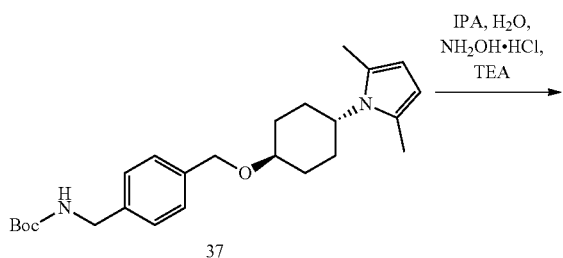

37

-continued

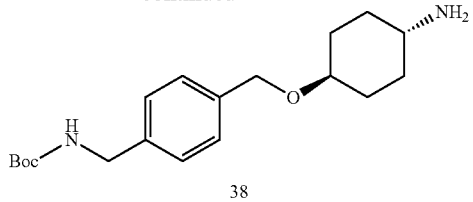

38

To a stirred mixture of tert-butyl (4-((((1r,4r)-4-(2,5-dimethyl-1H-pyrrol-1-yl)cyclohexyl)oxy)methyl)benzyl)carbamate (102 mg, 0.250 mmol, 1.00 equiv) in IPA (4.3 mL) and Water (1.1 mL) was added hydroxylamine; hydrochloride (257 mg, 3.710 mmol, 1.50 equiv). To the above mixture was added TEA (0.4 mL) and then stirred overnight at 80° C. The crude product was purified by reverse flash chromatography with the following conditions (Spherial C18, 80 g, 20-40 m; Mobile Phase A: water (0.05% $NH_4HCO_3$), Mobile Phase B: ACN; Flow rate: 60 mL/min; Gradient: 0% B to 100% B in 10 min, 210 nm; RT: 9 min) to afford tert-butyl (4-((((1r,4r)-4-aminocyclohexyl)oxy)methyl)benzyl)carbamate (65.0 mg, 0.194 mmol, 78% yield) as a yellow solid. LCMS (ESI, m/z): 335 [M+H]$^+$.

Step 35-5: tert-butyl (4-((((1r,4r)-4-(3-((2-(2,6-di-oxopiperidin-3-yl)-1-oxoisoindolin-5-yl)methyl)ureido)cyclohexyl)oxy)methyl)benzyl)carbamate

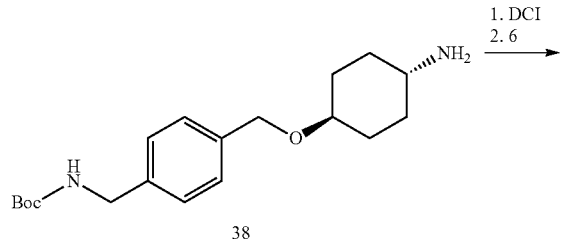

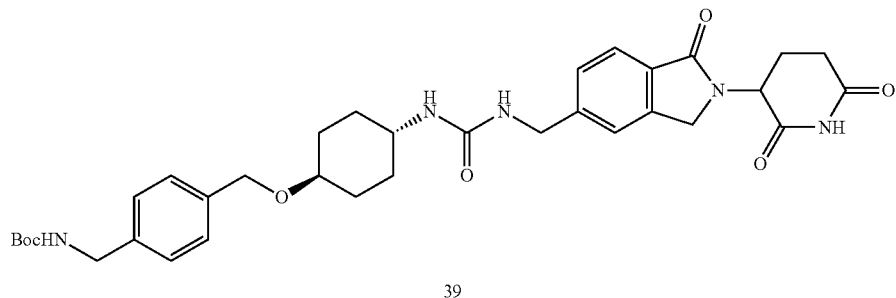

To a stirred mixture of tert-butyl (4-((((1r,4r)-4-aminocyclohexyl)oxy)methyl)benzyl)carbamate (44 mg, 0.130 mmol, 1.00 equiv) in DCE (2.0 mL) was added carbonyl diimidazole (23 mg, 0.140 mmol, 1.08 equiv). The resulting mixture was stirred for 2 h at 60° C. The resulting mixture was concentrated under reduced pressure. The residue was dissolved in 2.0 mL MeCN and then added a solution 3-[5-(aminomethyl)-1-oxo-isoindolin-2-yl]piperidine-2,6-dione; 2,2,2-trifluoroacetaic acid salt (51 mg, 0.130 mmol, 1.00 equiv) and 1.0 mL TEA in DMF. The resulting mixture was stirred for 2 h at room temperature. The crude product was purified by reverse flash chromatography with the following conditions (Spherial C18, 48 g, 20-40 m; Mobile Phase A: water (0.05% TFA), Mobile Phase B: ACN; Flow rate: 50 mL/min; Gradient: 0% B to 100% B in 20 min, 210 nm; RT: 11.0 min) to afford tert-butyl (4-((((1r,4r)-4-(3-((2-(2,6-dioxopiperidin-3-yl)-1-oxoisoindolin-5-yl)methyl)ureido)cyclohexyl)oxy)methyl)benzyl)carbamate (21.0 mg, 0.033 mmol, 25% yield) as a light yellow solid. LCMS (ESI, m/z): 634 [M+H]⁺.

Step 35-6: 3-{[2-(2,6-dioxopiperidin-3-yl)-1-oxo-2,3-dihydro-1H-isoindol-5-yl]methyl}-1-[(1r,4r)-4-{[4-(aminomethyl)phenyl]methoxy}cyclohexyl]urea

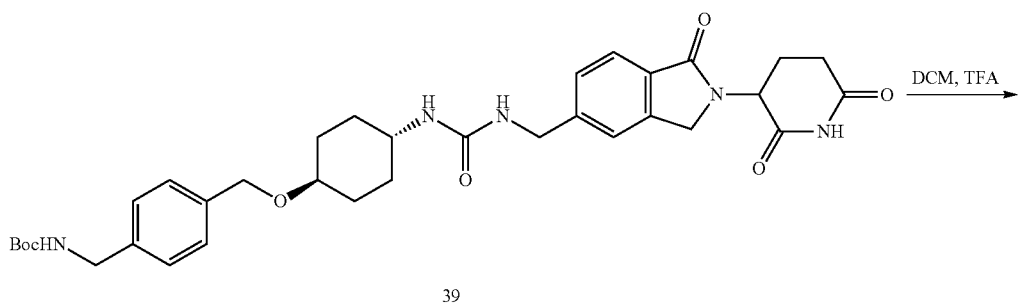

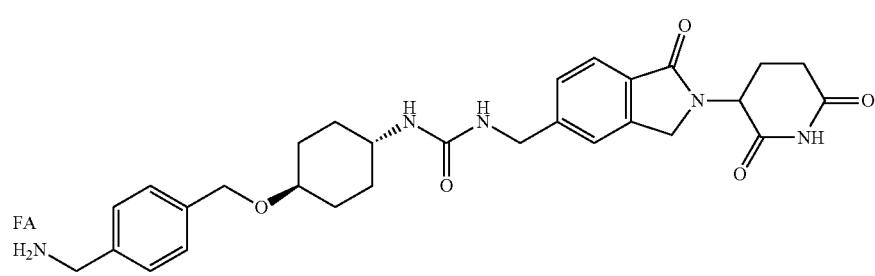

EX. 35

To a stirred mixture of tert-butyl (4-((((1r,4r)-4-(3-((2-(2,6-dioxopiperidin-3-yl)-1-oxoisoindolin-5-yl)methyl)ureido)cyclohexyl)oxy)methyl)benzyl)carbamate (16 mg, 0.030 mmol, 1.00 equiv) in DCM (1.8 mL) was added TFA (0.6 mL). The resulting mixture was stirred for 2 h at room temperature. After the mixture was concentrated under reduced pressure, the crude product was dissolved in 1.0 ml ACN, and then added 1.0 ml saturated $NaHCO_3$ solution to adjust the PH value to 8. The crude product (30 mg) was purified by Prep-HPLC with the following conditions (Column: Xselect CSH C18 OBD Column 30*150 mm 5 μm, n; Mobile Phase A: Water (0.1% FA), Mobile Phase B: ACN; Flow rate: 60 mL/min; Gradient: 2% B to 20% B in 10 min, 20% B; Wave Length: 254 nm; RT1 (min): 10.57; Number Of Runs: 0) to afford 3-{[2-(2,6-dioxopiperidin-3-yl)-1-oxo-2,3-dihydro-1H-isoindol-5-yl]methyl}-1-[(1r,4r)-4-{[4-(aminomethyl)phenyl]methoxy}cyclohexyl]urea (7.6 mg, 0.014 mmol, 56% yield) as a white solid. LCMS (ESI, m/z): 534 $[M+H]^+$. $^1$H NMR (400 MHz, Methanol-$d_4$) δ 8.50 (s, 1H), 7.75 (d, J=7.9 Hz, 1H), 7.49 (s, 1H), 7.47-7.37 (m, 1H), 7.42 (s, 4H), 5.14 (dd, J=13.3, 5.2 Hz, 1H), 4.57 (s, 2H), 4.55-4.39 (m, 4H), 4.09 (s, 2H), 3.44-3.35 (m, 1H), 2.91 (ddd, J=17.6, 13.5, 5.4 Hz, 1H), 2.78 (ddd, J=17.5, 4.7, 2.4 Hz, 1H), 2.49 (qd, J=13.2, 4.6 Hz, 1H), 2.21-2.08 (m, 1H), 2.07 (s, 2H), 1.97 (d, J=12.7 Hz, 2H), 1.47-1.39 (m, 1H), 1.37 (d, J=10.6 Hz, 1H), 1.31-1.16 (m, 2H).

Evaluation of the Activity of the Compounds

Standard physiological, pharmacological and biochemical procedures are available for testing the compounds to identify those that possess the desired anti-proliferative activity.

Such assays include, for example, biochemical assays such as binding assays, radioactivity incorporation assays, as well as a variety of cell based assays.

Biology

Targeted protein degradation represents a new paradigm in drug discovery, in which small molecules can be used to induce novel protein-protein interactions and enable destruction of target proteins that drive disease. Induction of protein degradation as a therapeutic strategy has been clinically validated by the class of immunomodulatory drugs developed by Celgene which include lenalidomide and pomalidomide. Removal of disease-driving proteins translates to the therapeutic benefits derived from immunomodulatory drug treatment. Specifically, CELMoDs (including immunomodulatory drugs) have the capacity to induce recruitment followed by ubiquitination of substrate proteins to the CRL4CRBN E3 ubiquitin ligase, after which, ubiquitin tagged proteins are trafficked to and subsequently degraded by the 26S proteasome. GSPT1 (G1 to S Phase Transition protein 1) is a translation termination factor with intrinsic GTPase activity. GSPT1 in complex with eRF1 recognizes the mRNA stop codon and functions to terminate protein translation by catalyzing the cleavage of the nascent protein from the terminal tRNA as well as by releasing the ribosomal subunits from the stop site allowing reformation and translation initiation at a new start site. Thus, GSPT1 plays a key role in protein synthesis and cell proliferation. Targeted degradation of GSPT1 by CELMoDs elicits broad antitumor activity in AML and solid tumor cells (1, 2).

1. Matyskiela M E, Lu G, Ito T, Pagarigan B, Lu C C, Miller K, Fang W, Wang N Y, Nguyen D, Houston J, Carmel G, Tran T, Riley M, Nosaka L, Lander G C, Gaidarova S, Xu S, Ruchelman A L, Handa H, Carmichael J, Daniel T O, Cathers B E, Lopez-Girona A, Chamberlain P P. A novel cereblon modulator recruits GSPT1 to the CRL4 (CRBN) ubiquitin ligase. Nature. 2016 Jul. 14; 535(7611):252-7. doi: 10.1038/nature18611. Epub 2016 Jun. 22. PMID: 27338790.
2. Surka C, Jin L, Mbong N, Lu C C, Jang I S, Rychak E, Mendy D, Clayton T, Tindall E, Hsu C, Fontanillo C, Tran E, Contreras A, Ng S W K, Matyskiela M, Wang K, Chamberlain P, Cathers B, Carmichael J, Hansen J, Wang J C Y, Minden M D, Fan J, Pierce D W, Pourdehnad M, Rolfe M, Lopez-Girona A, Dick J E, Lu G. CC-90009, a novel cereblon E3 ligase modulator, targets acute myeloid leukemia blasts and leukemia stem cells. Blood. 2021 Feb. 4; 137(5):661-677. doi: 10.1182/blood.2020008676. PMID: 33197925; PMCID: PMC8215192.

Cell Assays

GSPT1 DiscoverX Degradation Assay.

DF15 multiple myeloma cells expressing ePL-tagged GSPT1 were dispensed into a 384-well plate (Corning #3712) pre-spotted with compound. Compounds were dispensed by an acoustic dispenser (ATS Acoustic Transfer System from EDC Biosystems) into a 384-well in a 10 pt dose response curve using 3 fold dilutions starting at 10 uM and going down to 0.0005 uM in DMSO. A DMSO control is added to the assay. 25 μL of media (RPMI-1640+10% Heat Inactivated FBS+25 mM Hepes+1 mM Na Pyruvate+1×NEAA+0.1% Pluronic F-68+1× Pen Strep Glutamine) containing 5000 cells was dispensed per well. Assay plates were incubated at 37° C. with 5% CO2 for twenty hours. After incubation, 25 μl of the InCELL Hunter™ Detection Reagent Working Solution (DiscoverX, cat #96-0002, Fremont, CA) was added to each well and incubated at room temperature for 30 minutes protected from light. After 30 minutes, luminescence was read on a PHERAstar luminometer (Cary, NC).

To determine $EC_{50}$ values for GSPT1 degradation, a four parameter logistic model (Sigmoidal Dose-Response Model) (FIT=(A+((B−A)/1+((C/x)^D)))) wherein C is the inflection point ($EC_{50}$), D is the correlation coefficient, A and B are the low and high limits of the fit respectively) was used to determine the compound's $EC_{50}$ value, which represents the half maximum effective concentration. The minimum Y is reference to the Y constant. In the GSPT1 degradation assay, we use Ataluren® (luciferase inhibitor) as the control with a Y constant=0. The maximum limit is the Y max DMSO control. All percent of control GSPT1 degradation curves were processed and evaluated using Activity Base (IDBS).

TABLE 2

GSPT1 Degradation Data

| Example# | EC50 (nM) | Ymin |
|---|---|---|
| 1 | 0.82 | 3.00 |
| 2 | 1.63 | 4.34 |
| 3 | 2.54 | 7.30 |
| 4 | 1.03 | 6.80 |
| 5 | 7.93 | 3.00 |
| 6 | 0.51 | 3.00 |
| 7 | 0.94 | 4.00 |
| 8 | 1.77 | 4.00 |
| 9 | 2.83 | 3.50 |
| 10 | 2.58 | 4.00 |
| 11 | 1.53 | 6.71 |
| 12 | 1.05 | 5.39 |

TABLE 2-continued

GSPT1 Degradation Data

| Example# | EC50 (nM) | Ymin |
|---|---|---|
| 13 | 2.69 | 6.75 |
| 14 | 11.66 | 5.83 |
| 15 | 37.29 | 3.10 |
| 16 | 96.60 | 12.67 |
| 17 | 137.97 | 15.91 |
| 18 | 789.78 | 54.45 |
| 19 | 57.5 | 6.55 |
| 20 | 3.11 | 7.50 |
| 21 | 3.50 | 10.44 |
| 22 | 1.30 | 9.46 |
| 23 | 2.15 | 8.85 |
| 24 | 1.54 | 10.04 |
| 25 | 2.17 | 5.50 |
| 26 | 3.31 | 6.92 |
| 27 | 1.23 | 6.15 |
| 28 | 6.29 | 10.20 |
| 29 | 1.70 | 16.88 |
| 30 | 3.27 | 10.86 |
| 31 | 5.38 | 7.07 |
| 32 | 303.68 | 22.76 |
| 33 | 3470.44 | 60.95 |
| 34 | 8.30 | 7.47 |
| 35 | 11.39 | 17.59 |

The embodiments described above are intended to be merely exemplary, and those skilled in the art will recognize, or will be able to ascertain using no more than routine experimentation, numerous equivalents of specific compounds, materials, and procedures. All such equivalents are considered to be within the scope of the invention and are encompassed by the appended claims.

What is claimed is:

1. A compound having a Formula II:

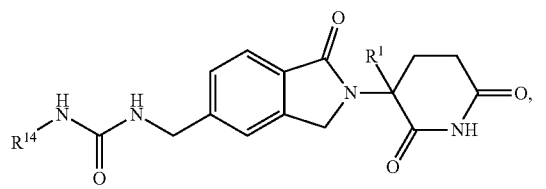

or a pharmaceutically acceptable salt, solvate, hydrate, co-crystal, clathrate, polymorph or tautomer thereof, a pharmaceutically acceptable salt of the polymorph or tautomer, a stereoisomer of any of the foregoing, or a mixture thereof, wherein:

$R^1$ is independently selected from hydrogen or methyl;

$R^{14}$ is independently selected from.

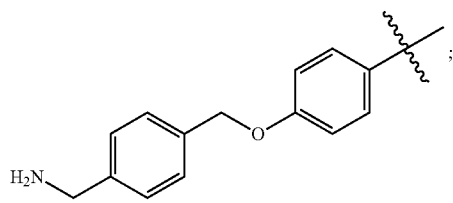

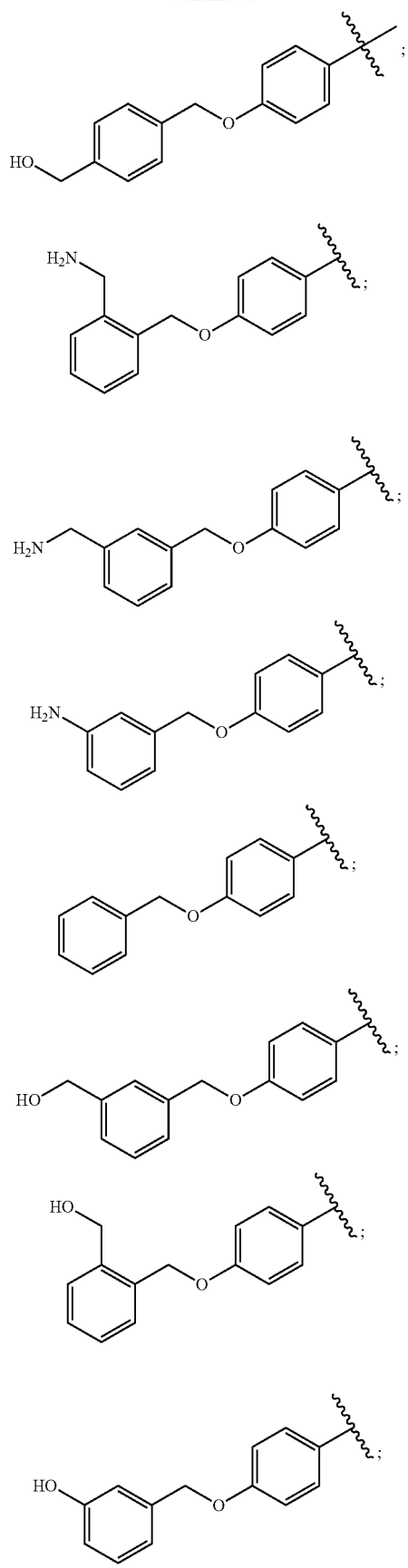

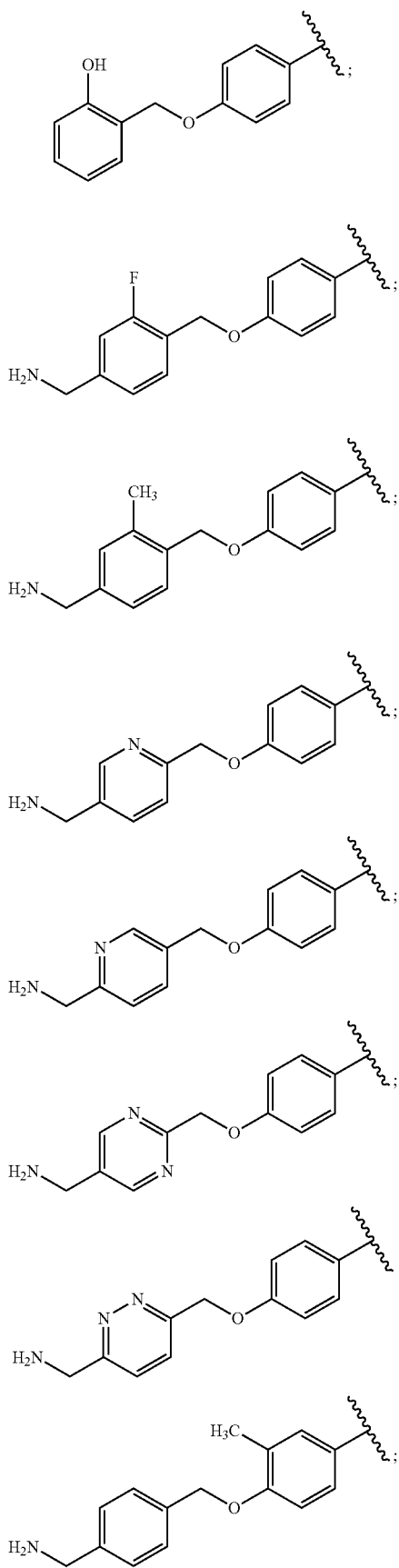
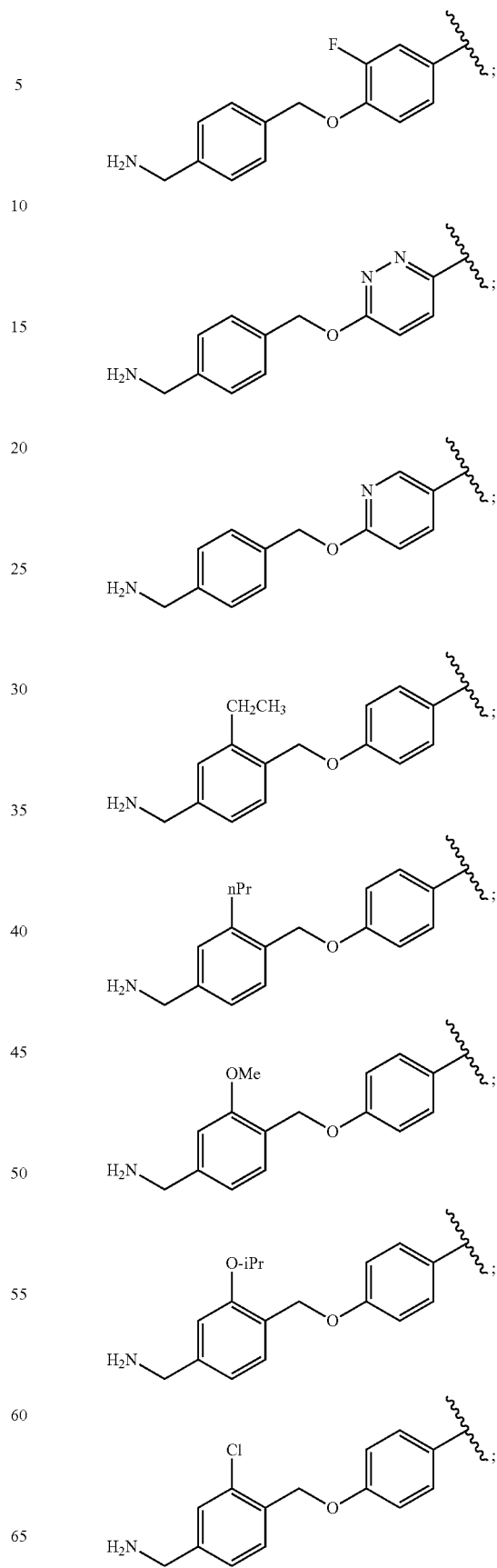

-continued

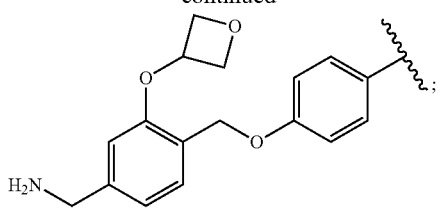

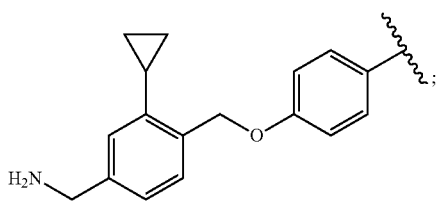

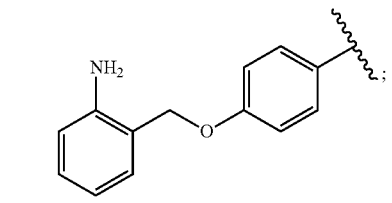

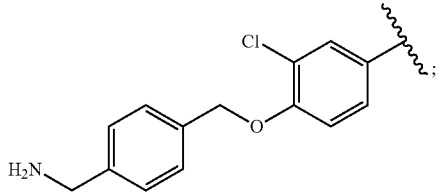

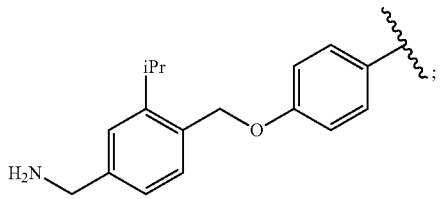

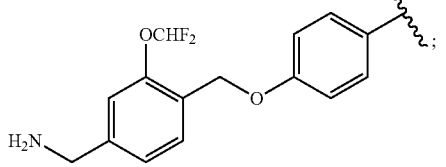

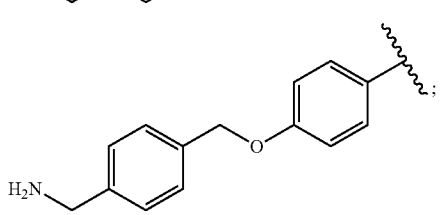

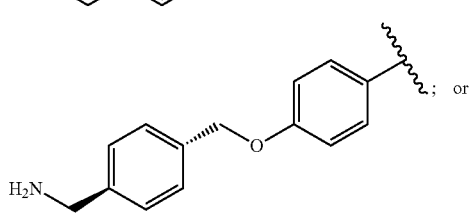

-continued

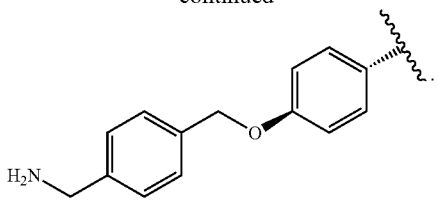

2. A compound, wherein the compound is selected from
1-((2-(2,6-dioxopiperidin-3-yl)-1-oxoisoindolin-5-yl)
methyl)-3-(4-((4-(hydroxymethyl)benzyl)oxy)phenyl)
urea,
1-[4-[[4-(aminomethyl)phenyl]methoxy]phenyl]-3-[[2-
(2,6-dioxo-3-piperidyl)-1-oxo-isoindolin-5-yl]methyl]
urea,
1-(4-((2-(aminomethyl)benzyl)oxy)phenyl)-3-((2-(2,6-
dioxopiperidin-3-yl)-1-oxoisoindolin-5-yl)methyl)
urea,
1-(4-((3-(aminomethyl)benzyl)oxy)phenyl)-3-((2-(2,6-
dioxopiperidin-3-yl)-1-oxoisoindolin-5-yl)methyl)
urea,
1-(4-((3-aminobenzyl)oxy)phenyl)-3-((2-(2,6-dioxopip-
eridin-3-yl)-1-oxoisoindolin-5-yl)methyl)urea,
1-[4-(benzyloxy)phenyl]-3-{[2-(2,6-dioxopiperidin-3-
yl)-1-oxo-2,3-dihydro-1H-isoindol-5-yl]methyl}urea,
1-((2-(2,6-dioxopiperidin-3-yl)-1-oxoisoindolin-5-yl)
methyl)-3-(4-((3-(hydroxymethyl)benzyl)oxy)phenyl)
urea,
1-((2-(2,6-dioxopiperidin-3-yl)-1-oxoisoindolin-5-yl)
methyl)-3-(4-((2-(hydroxymethyl)benzyl)oxy)phenyl)
urea,
1-((2-(2,6-dioxopiperidin-3-yl)-1-oxoisoindolin-5-yl)
methyl)-3-(4-((2-hydroxybenzyl)oxy)phenyl)urea,
1-((2-(2,6-dioxopiperidin-3-yl)-1-oxoisoindolin-5-yl)
methyl)-3-(4-((2-hydroxybenzyl)oxy)phenyl)urea,
1-(4-{[4-(aminomethyl)-2-fluorophenyl]
methoxy}phenyl)-3-{[2-(2,6-dioxopiperidin-3-yl)-1-
oxo-2,3-dihydro-1H-isoindol-5-yl]methyl}urea,
1-(4-{[4-(aminomethyl)-2-methylphenyl]
methoxy}phenyl)-3-{[2-(2,6-dioxopiperidin-3-yl)-1-
oxo-2,3-dihydro-1H-isoindol-5-yl]methyl}urea,
1-(4-{[5-(aminomethyl) pyridin-2-yl]methoxy}phenyl)-
3-{[2-(2,6-dioxopiperidin-3-yl)-1-oxo-2,3-dihydro-
1H-isoindol-5-yl]methyl}urea,
1-(4-{[6-(aminomethyl) pyridin-3-yl]methoxy}phenyl)-
3-{[2-(2,6-dioxopiperidin-3-yl)-1-oxo-2,3-dihydro-
1H-isoindol-5-yl]methyl}urea,
1-(4-{[5-(aminomethyl) pyrimidin-2-yl]
methoxy}phenyl)-3-{[2-(2,6-dioxopiperidin-3-yl)-1-
oxo-2,3-dihydro-1H-isoindol-5-yl]methyl}urea,
1-(4-{[6-(aminomethyl) pyridazin-3-yl]
methoxy}phenyl)-3-{[2-(2,6-dioxopiperidin-3-yl)-1-
oxo-2,3-dihydro-1H-isoindol-5-yl]methyl}urea,
1-(4-{[4-(aminomethyl)phenyl]methoxy}-3-methylphe-
nyl)-3-{[2-(2,6-dioxopiperidin-3-yl)-1-oxo-2,3-di-
hydro-1H-isoindol-5-yl]methyl}urea,
1-(4-{[4-(aminomethyl)phenyl]methoxy}-3-fluorophe-
nyl)-3-{[2-(2,6-dioxopiperidin-3-yl)-1-oxo-2,3-di-
hydro-1H-isoindol-5-yl]methyl}urea,
1-(6-{[4-(aminomethyl)phenyl]methoxy}pyridazin-3-
yl)-3-{[2-(2,6-dioxopiperidin-3-yl)-1-oxo-2,3-di-
hydro-1H-isoindol-5-yl]methyl}urea,
1-(6-{[4-(aminomethyl)phenyl]methoxy}pyridin-3-yl)-3-
{[2-(2,6-dioxopiperidin-3-yl)-1-oxo-2,3-dihydro-1H-
isoindol-5-yl]methyl}urea, 1-(4-{[4-(aminomethyl)-2-ethylphenyl]methoxy}phenyl)-3-{[2-(2,6-dioxopiperidin-3-yl)-1-oxo-2,3-dihydro-1H-isoindol-5-yl]methyl}urea, 1-(4-{[4-(aminomethyl)-2-n-propylphenyl]methoxy}phenyl)-3-{[2-(2,6-dioxopiperidin-3-yl)-1-oxo-2,3-dihydro-1H-isoindol-5-yl]methyl}urea, 1-(4-{[4-(aminomethyl)-2-methoxyphenyl]methoxy}phenyl)-3-{[2-(2,6-dioxopiperidin-3-yl)-1-oxo-2,3-dihydro-1H-isoindol-5-yl]methyl}urea, 1-(4-{[4-(aminomethyl)-2-(propan-2-yloxy)phenyl]methoxy}phenyl)-3-{[2-(2,6-dioxopiperidin-3-yl)-1-oxo-2,3-dihydro-1H-isoindol-5-yl]methyl}urea, 1-(4-{[4-(aminomethyl)-2-chlorophenyl]methoxy}phenyl)-3-{[2-(2,6-dioxopiperidin-3-yl)-1-oxo-2,3-dihydro-1H-isoindol-5-yl]methyl}urea, 1-(4-{[4-(aminomethyl)-2-(oxetan-3-yloxy)phenyl]methoxy}phenyl)-3-{[2-(2,6-dioxopiperidin-3-yl)-1-oxo-2,3-dihydro-1H-isoindol-5-yl]methyl}urea, 1-(4-{[4-(aminomethyl)-2-cyclopropylphenyl]methoxy}phenyl)-3-{[2-(2,6-dioxopiperidin-3-yl)-1-oxo-2,3-dihydro-1H-isoindol-5-yl]methyl}urea, 1-(4-((2-aminobenzyl)oxy)phenyl)-3-((2-(2,6-dioxopiperidin-3-yl)-1-oxoisoindolin-5-yl)methyl)urea, 1-(4-((4-(aminomethyl)benzyl)oxy)-3-chlorophenyl)-3-((2-(2,6-dioxopiperidin-3-yl)-1-oxoisoindolin-5-yl)methyl)urea, 1-(4-{[4-(aminomethyl)-2-i-propylphenyl]methoxy}phenyl)-3-{[2-(2,6-dioxopiperidin-3-yl)-1-oxo-2,3-dihydro-1H-isoindol-5-yl]methyl}urea, 1-(4-{[4-(aminomethyl)-2-diflouromethoxyphenyl]methoxy}phenyl)-3-{[2-(2,6-dioxopiperidin-3-yl)-1-oxo-2,3-dihydro-1H-isoindol-5-yl]methyl}urea, 1-(4-{[4-(aminomethyl)phenyl]methoxy}phenyl)-3-({2-[(3S)-3-methyl-2,6-dioxopiperidin-3-yl]-1-oxo-2,3-dihydro-1H-isoindol-5-yl}methyl)urea, 1-(4-{[4-(aminomethyl)phenyl]methoxy}phenyl)-3-({2-[(3R)-3-methyl-2,6-dioxopiperidin-3-yl]-1-oxo-2,3-dihydro-1H-isoindol-5-yl}methyl)urea, 3-{[2-(2,6-dioxopiperidin-3-yl)-1-oxo-2,3-dihydro-1H-isoindol-5-yl]methyl}-1-(4-{[(1r,4r)-4-(aminomethyl)cyclohexyl]methoxy}phenyl)urea or 3-{[2-(2,6-dioxopiperidin-3-yl)-1-oxo-2,3-dihydro-1H-isoindol-5-yl]methyl}-1-[(1r,4r)-4-{[4-(aminomethyl)phenyl]methoxy}cyclohexyl]urea, or a pharmaceutically acceptable salt, solvate, hydrate, co-crystal, clathrate, polymorph or tautomer thereof, a pharmaceutically acceptable salt of the polymorph or tautomer, a stereoisomer of any of the foregoing, or a mixture thereof.

* * * * *